US008182984B2

(12) United States Patent
Fang et al.

(10) Patent No.: US 8,182,984 B2
(45) Date of Patent: May 22, 2012

(54) RECOMBINANT NORTH AMERICAN TYPE 1 PORCINE REPRODUCTIVE AND RESPIRATORY SYNDROME VIRUS AND METHODS OF USE

(75) Inventors: Ying Fang, Brookings, SD (US); Eric A. Nelson, Volga, SD (US); Jane Hennings, Ar

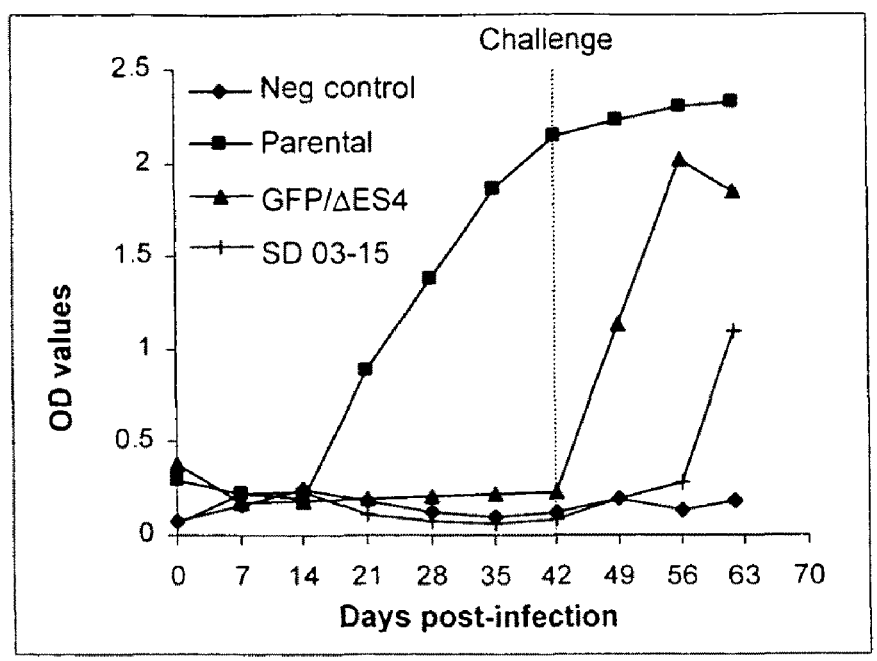
FIG. 15A. ES4 epitope-based ELISA.
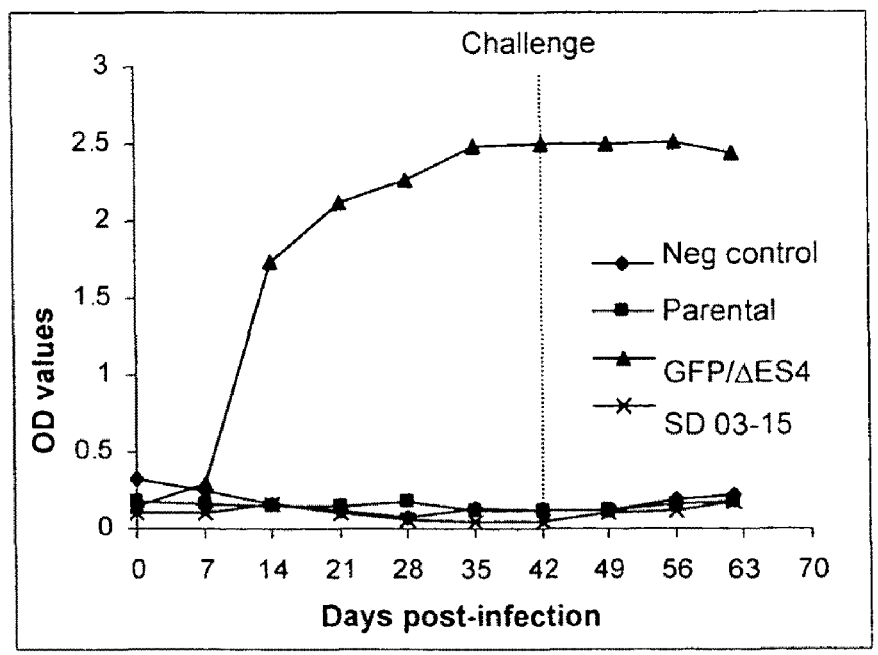
FIG. 15B. GFP antigen-based ELISA.

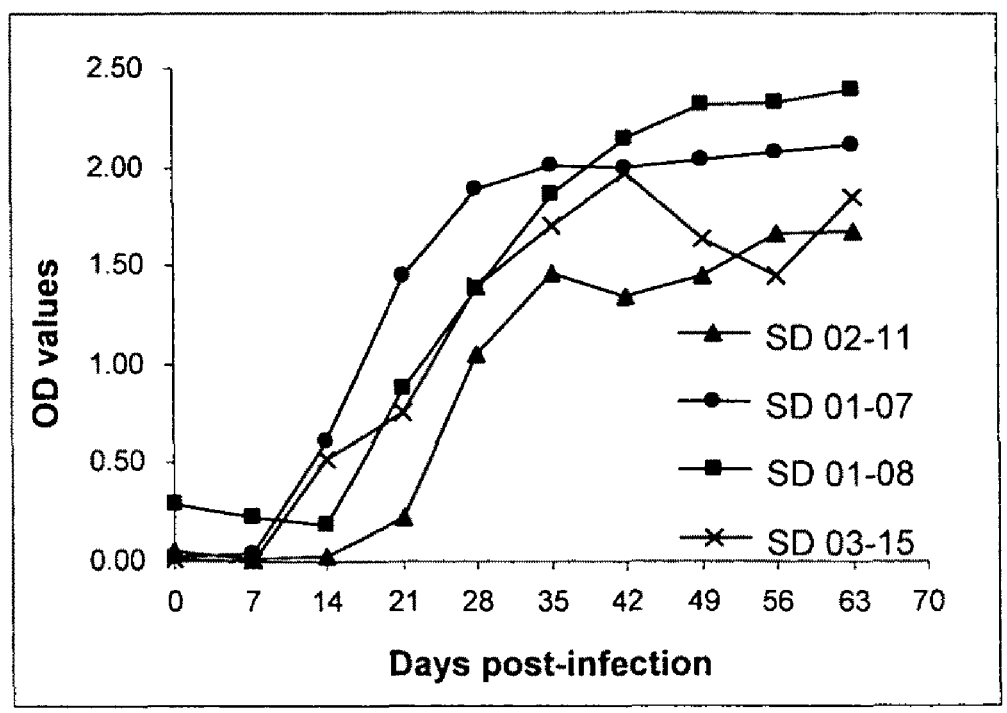
FIG. 15C. ES4 epitope-based ELISA.

ID NO: 43 or a sequence homologous thereto.
RECOMBINANT NORTH AMERICAN TYPE 1 PORCINE REPRODUCTIVE AND RESPIRATORY SYNDROME VIRUS AND METHODS OF USE This application claims the benefit of U.S. Provisional Application Ser. No. 60/946,080, filed Jun. 25, 2007.

TECHNICAL FIELD

This application relates to the field of molecular virology and more particularly to the construction of recombinant nucleic acids encoding Porcine Reproductive and Respiratory Syndrome Virus (PRRSV).

BACKGROUND

Porcine reproductive and respiratory syndrome (PRRS) is the most economically significant disease of swine worldwide. It is characterized by late term reproductive failure in sows and severe pneumonia in neonatal pigs. The PRRS virus (PRRSV) consists of two major genotypes, European genotype (Type 1) and North American genotype (Type 2), each formerly located on different continents. More recently, Type 1 PRRSV isolates (North American Type 1) have been identified in U.S. swineherds. This group of viruses possesses unique antigenic and genetic characteristics that are distinct from typical North American and European type PRRSV. A unique 51 by deletion has been identified in the immunodominant region of the Nsp2. The etiologic agent of PRRS is a small, enveloped virus containing a single positive-stranded RNA genome. PRRSV belongs to the family Arteriviridae, which includes equine arteritis virus (EAV), lactate dehydrogenase-elevating virus (LDV), and simian hemorrhagic fever virus (SHFV) (Snijder & Meulenberg, 1998). Nucleotide sequence comparisons showed that PRRSV can be divided into distinct European (Type 1) and North American (Type 2) genotypes (Allende et al., 1999; Nelson et al., 1999).

The PRRSV genome is about 15 kb in length and contains nine open reading frames. The 3' end of the genome encodes four membrane-associated glycoproteins (GP2a, GP3, GP4 and GP5; encoded by sg mRNAs 2-5), two unglycosylated membrane proteins (E and M; encoded by sg mRNAs 2 and 6) and a nucleocapsid protein (N; encoded by sg mRNA 7) (Bautista et al., 1996; Mardassi et al., 1996; Meng et al., 1996; Meulenberg & den Besten, 1996; Meulenberg et al., 1995; Mounir et al., 1995; Wu et al., 2001, 2005). The replicase-associated genes, ORF1a and ORF1b, situated at the 5' end of the genome, represent nearly 75% of the viral genome. The ORF1ab encoded polyprotein pp1ab is predicted to be cleaved at 12 sites to form 13 products: nsp1α, nsp1β, and nsp2 to nsp12 (Allende et al., 1999; den Boon et al., 1995; Nelsen et al., 1999; Snijder & Meulenberg, 1998).

Modified-live attenuated vaccines against PRRSV are currently available for reduction of clinical disease associated with PRRSV (Boehringer-Ingelheim Animal Health, Inc.). However, they cannot be distinguished serologically between pigs that have recovered from a natural infection and those that have been vaccinated. A genetically marked vaccine would allow the differentiation between vaccinated and naturally infected pigs, which is needed for PRRSV control and eradication programs.

SUMMARY

A recombinant porcine reproductive and respiratory syndrome virus (PRRSV) includes one or more mutations in open reading frame (ORF) 1a, the mutations being such that the recombinant PRRSV fails to produce at least one functional polypeptide corresponding to ORF1a. The mutation may be a deletion. A deletion may be in the nsp2 region, and may include epitope ES4. In one embodiment, the deletion includes amino acids 736-790 of ORF1a. The mutation may include an insertion of a heterologous DNA sequence. An insertion may be between amino acids 733 and 734 of ORF1a. The insertion may include green fluorescent protein (GFP).

A recombinant North American PRRS virus is encoded by an isolated polynucleotide molecule including a DNA sequence encoding an infectious RNA molecule encoding a North American PRRS virus, and the DNA sequence is SEQ ID NO: 43 or a sequence homologous thereto.

A vaccine includes a PRRSV mutant having a mutation in ORF1a, the mutation being such that said PRRSV mutant fails to produce a functional ORF1a polypeptide, and the vaccine includes a pharmaceutically acceptable carrier. The mutation may include a deletion in the nsp2 region, such as a deletion of amino acids 736-790 in the nsp2 region. The mutation may include an insertion of a heterologous DNA sequence. The insertion may be between amino acids 733 and 734 in the nsp2 region.

A kit includes a vaccine including a PRRSV mutant having a mutation in ORF1a, the mutation being such that said PRRSV mutant fails to produce a functional ORF1a polypeptide, the mutation including an insertion of a heterologous DNA sequence, and a pharmaceutically acceptable carrier. The kit further including one or more first polypeptides encoded by the heterologous DNA sequence, and one or more second polypeptides encoded by the functional ORF1a. The mutation in the PRRSV vaccine may be a deletion in the nsp2 region, such as in an ES4 epitope, and the one or more first polypeptides include GFP and the one or more second polypeptides include the ES4 epitope.

A method is provided for differentiating an animal vaccinated with a PRRSV marker vaccine from an animal naturally infected with PRRSV, where the PRRSV marker vaccine includes an insertion mutation and a deletion mutation. The method includes the steps of providing a first recombinant PRRSV protein including the insertion mutation, providing a second recombinant PRRSV protein including the deletion mutation, incubating a serum sample from the animal with the first and second recombinant PRRSV proteins, and detecting binding of antibodies in the sample with the first and second recombinant PRRSV proteins. Binding of antibodies in the sample with the first recombinant PRRSV protein is indicative of a vaccinated animal and binding of antibodies in the sample with the second recombinant PRRSV protein is indicative of a naturally infected animal. The first recombinant PRRSV protein may include a GFP insertion, and the second recombinant PRRSV protein may include an ES4 deletion.

BRIEF DESCRIPTION OF THE DRAWINGS

FIG. 13 is a graph depicting in vivo characteristics of the GFP/ΔES4 marker virus.

FIGS. 14A-14C are graphs depicting virological and immunological properties of the GFP/ΔES4 marker virus.

FIGS. 15A-15C depict GFP and ES4 epitope-based ELISA results.

DETAILED DESCRIPTION

Figure 1:
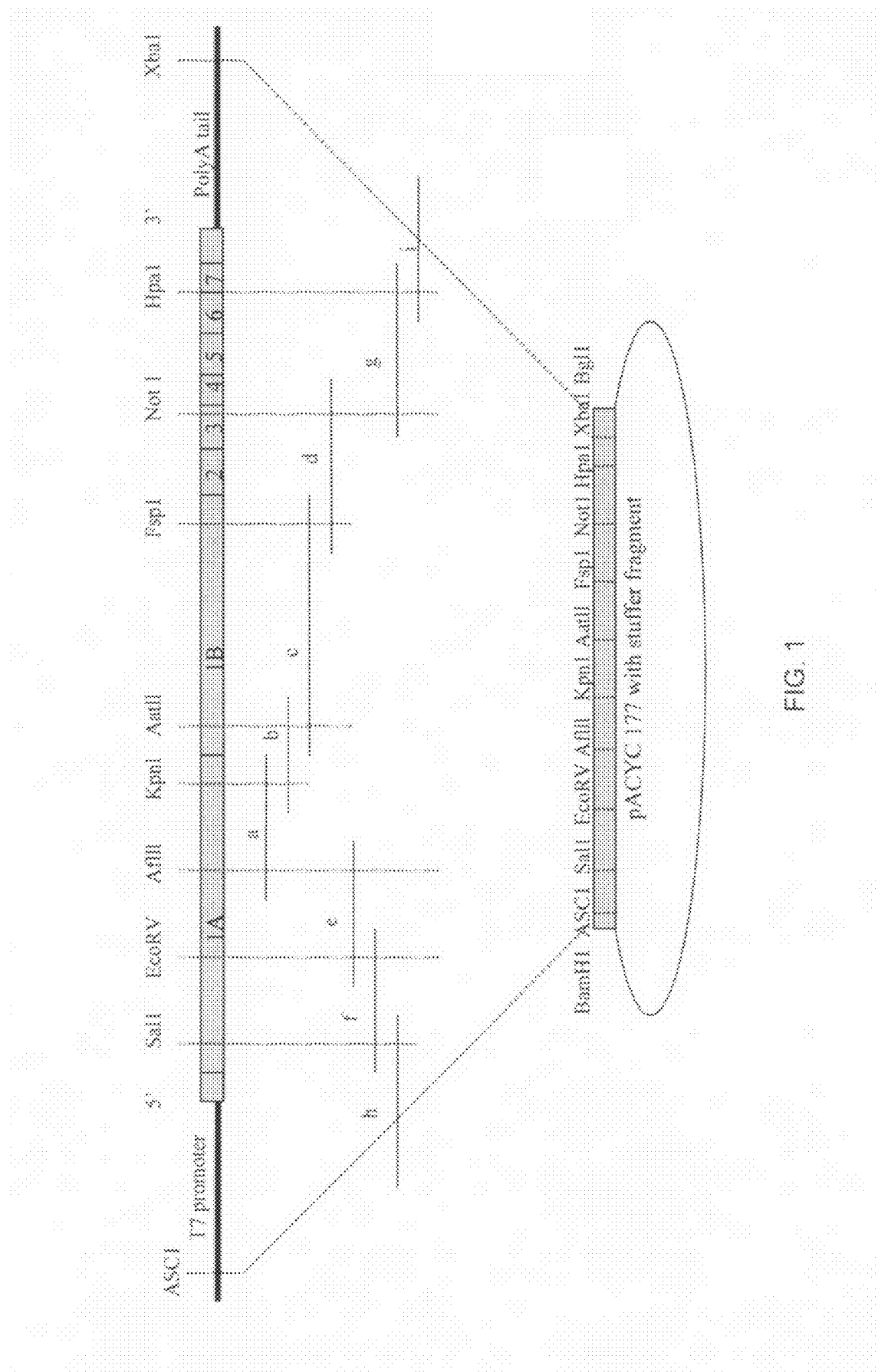
FIG. 1 is a schematic representation of the PRRSV genome and cloning strategy.

A full-length cDNA clone, SD01-08, of a North American Type 1 PRRSV isolate was developed. When compared to Lelystad virus, SD01-08 shares 94.1% identity at the nucleotide level (GenBank accession number DQ489311). An important distinction between SD01-08 and LV is the growth properties in PAMs and monkey kidney cells. Results reported by Meulenberg et al (15) showed that wild-type and cloned LV viruses grew well in PAMs, but to low levels in the MA-104 derived cell line, CL2621. Parental and cloned SD01-08 grew equally well on PAMs and MARC-145 cells, another MA-104 derived cell line. The titer of SD01-08 cloned viruses peaked at 48 hpi, while LV cloned viruses grow to lower titers and had not peaked even at 96 hpi. Therefore, the SD01-08 infectious clone replicates well in the continuous cell line. Another difference between LV and SD01-08 is in the level of virulence. In PAMs, the LV cloned virus reached high titers at $10^{7.1}$ to $10^{7.9}$ TCID$_{50}$/ml and peaked around 32 hpi. The SD01-08 cloned virus reached the same titer as its parental virus in PAMs, but their titers were both lower than that of LV, reaching only about $10^4$ TCID$_{50}$/ml and peaked later, around 72 hpi. This result suggests that SD01-08 cloned virus is less virulent than the LV cloned virus. This conclusion is supported by field observations and an experimental animal challenge study. SD01-08 did not cause significant clinical signs, and only mild pathological lesions observed in the experimental infected pigs. In contrast, LV was reported to cause significant respiratory problems in pigs and abortions in sows (34).

One of the major applications of the infectious clone is to use it as viral backbone for constructing genetically engineered vaccines. Current PRRSV vaccines in the U.S. mainly target the North American Type 2 isolates. The emergence of the North American Type 1 PRRSV requires that vaccines be effective for both genotypes of PRRSV. An essential requirement for any live virus vaccine is that it be low virulence, inducing no or at most very mild disease manifestations. The parental virus, SD01-08 was isolated from a group of pigs showing no clinical signs. Pathogenesis studies confirmed that SD01-08 possesses low virulence properties at the acute phase of the disease, which suggested that the pSD01-08 infectious clone is a potential low virulent strain and suitable for vaccine construction.

One of the key steps in vaccine development is to include markers for the diagnostic differentiation of vaccinated animals from those that are naturally infected with wild-type virus. Marker vaccines are important in programs aimed at controlling or eradicating virus infections in food animals, as well as in companion animals (Babiuk, 1999; Babiuk et al., 1999, 2002; van Oirschot, 2001). Herpesvirus marker vaccines were among the first proved to be effective in the field (Bosch et al., 1996; van Oirschot et al., 1996), followed by various genetically modified RNA viruses, such as classical swine fever virus (Widjojoatmodjo et al., 2000; van Gennip et al., 2002) and Rinderpest virus (Walsh et al., 2000). In EAV eradication programs, since horses are actively involved in international trade and traffic, a marker vaccine is required by some legislative authorities. Discrimination between vaccination and infection is becoming a ruling issue (Castillo-Olivares et al., 2003). Similarly, with a PRRSV elimination program, the international trade in pigs and pork will likely require a marker vaccine in the future. Furthermore, as the world is progressively moving toward elimination of PRRSV, serosurveillance is an essential tool to verify the disease status. The currently available conventional vaccines are unable to allow differentiation between wild-type infection and vaccination. Thus, serosurveillance is impossible in the face of ongoing vaccination or for several months after vaccination has ceased. Clearly, a marked vaccine would be of great benefit.

An infectious clone of North American Type 1 PRRSV, pSD01-08 was used to create a recombinant PRRSV. Compared to a European Lelystad virus (LV) infectious clone, pSD01-08 possesses several distinct biological properties: (1) the pSD01-08 infectious clone was derived from a parental strain isolated in the U.S. in 2001, which represents a North American Type 1 PRRSV; (2) the parental strain SD01-08 was isolated from a group of 8-week-old pigs showing no clinical signs; and (3) SD01-08 possesses a unique 51 by deletion in the immunodominant region of Nsp2 (Fang et al., 2004).

The nsp2 plays a role in the viral replication. The nsp2 contains a cysteine protease domain residing in the N-terminal. This domain induces nsp2/3 cleavage, and also functions as a co-factor with nsp4 serine protease to process the other cleavage products (Snijder et al., 1994, 1995; Wassenaar et al., 1997). Besides its function in viral replication, cysteine proteases of EAV and PRRSV nsp2 have been shown to belong to the ovarian tumor (OTU) protease superfamily. The OTU protease is capable of deconjugating both ubiquitin and ISG15 from cellular proteins, which inhibits Ub- and ISG15-dependent innate immune response (Frias-Staheli et al., 2007).

The development of the marker vaccine is based on the manipulation of cDNA infectious clones, from where a foreign antigen can be inserted (positive marker) or an immunogenic epitope can be deleted (negative marker). The antibody response to the foreign antigen or viral epitope can be used to differentiate vaccinated animals from naturally infected animals. The PRRSV nsp2 is an excellent candidate site for marker modification. The most important property of nsp2 related to marker engineering is the ability of nsp2 to tolerate large deletions and insertions. Nucleotide sequence insertions/deletions have been reported within the central region of the protein (Gao et al., 2004; Shen et al., 2000; Tian et al., 2007; Han et al., 2007). Another property related to marker engineering is the presence of several immunodominant epitopes in this region. Six linear B-cell epitope sites (ES) in the nsp2 region of a Danish Type 1 virus (ES2 to ES7) have been identified (Oleksiewicz et al., 2001). In Type 2 virus, the nsp2 has been found to contain the highest frequency of immunodominant epitopes when compared to structural proteins (de Lima et al., 2006).

Marker modifications in the nsp2 region of a US Type 1 PRRSV infectious clone were prepared. A positive marker, GFP, was inserted into the nsp2 region, but the GFP gene was not stable. Next, a highly immunogenic epitope, ES4, located in the nsp2 region (amino acid 736 to 790 of ORF1a) was deleted and replaced with the GFP gene (at amino acid 733/734 of ORF1a) using reverse genetics, to create a negative marker. The resulting recombinant virus' in vitro replication features and in vivo biological properties were characterized to determine its potential use as marker vaccine against PRRSV infection. The GFP antigen and ES4 peptide antigen-based ELISAs were tested to determine their sensitivity and specificity as companion diagnostic assays for the marker detection and differentiation.

I. Positive Marker GFP

Cells and viruses. A North American Type 1 PRRSV isolate, SD01-08, was originally isolated in 2001 from a group of 8-week-old pigs in the U.S., which were showing no clinical signs of PRRS. Baby hamster kidney cells (BHK-21 C13: American Type Culture Collection) were used for initial transfection for recovery of virus from in vitro transcribed RNA. MARC-145 cells were used for virus rescue and subsequent experiments (Fang et al., 2006). Porcine alveolar macrophages (PAM) cells were obtained by lung lavage of specific-pathogen-free piglets free of PRRSV.

RNA extraction, RT-PCR and sequencing: MARC-145 cells were infected with plaque purified viruses at an MOI of approximately 0.1. After three days, the culture supernatant was layered onto a 0.5 M sucrose cushion and centrifuged at 100,000×g for 14 h in a SW41 rotor (Beckman). RNA was extracted from the pellet using a QIAamp viral RNA kit (Qiagen). To obtain the full-length genome sequence of the parental virus, SD01-08, RT-PCR was performed using a series of primers (Ropp et al., 2004). Each RT-PCR product was directly sequenced at least two times from both directions to obtain the consensus sequences. To construct the infectious clone, nine overlapping fragments (FIG. 1) covering the full-length viral genome flanked by unique restriction enzyme sites were amplified by RT-PCR. The forward and reverse oligonucleotides for the RT-PCR amplification were designed initially based on the sequence of LV (GenBank accession number M96262; 18) and later modified to match SD01-08 sequence (Table 1). RT-PCR was performed (Fang et al., 2004). These RT-PCR amplified fragments were gel purified and cloned in the PCR-Blunt II-Topo vector (Invitrogen). Three clones of each fragment were sequenced and the clone containing the consensus sequence was used for infectious clone assembly.

TABLE 1

Primers used for RT-PCR amplification

| Primers | Sequences | Genome Position in SD01-08 |
|---|---|---|
| Fragment a | | |
| E4849F | 5' gca tgg ctc tta agg cag ac SEQ ID NO. 1 | 4849-4868 |
| E7227R | 5' cag ctt caa ggc agt tgt ca SEQ ID NO. 2 | 7208-7227 |
| Fragment b | | |
| E7139F | 5' tgt tgt gat cgg cgg tat ta SEQ ID NO. 3 | 7139-7158 |
| E8297R | 5' cgg cgc ggg cac aca ttt cgt caa ttt SEQ ID NO. 4 | 8271-8297 |
| Fragment c | | |
| E8090F | 5' tac gac cta tcc acc caa gg SEQ ID NO. 5 | 8090-8109 |
| E10275R | 5' gaa tct atg gtt atc gca gag c SEQ ID NO. 6 | 10254-10275 |
| Fragment d | | |
| E9946F | 5' cct cga tga ggc tgg ata tt SEQ ID NO. 7 | 9946-9965 |
| E12929R | 5' gca cca acc agg agg aaa aaa gc SEQ ID NO. 8 | 12907-12929 |
| Fragment e | | |
| E3173F | 5' cat tct tgc gtc cct caa at SEQ ID NO. 9 | 3173-3192 |
| E5352R | 5' cga cag tct ttc tgc cat caa tg SEQ ID NO. 10 | 5330-5352 |
| Fragment f | | |
| E2229F | 5' gct gct gtt gtc ctg tgt t SEQ ID NO. 11 | 2229-2247 |
| E3397R | 5' ccg tcg aag ggg gtg gca tcc SEQ ID NO. 12 | 3377-3397 |
| Fragment g | | |
| E12482F | 5' tca ttc gag ctg acc atc aa SEQ ID NO. 13 | 12482-12501 |
| E14651R | 5' ctt tat cat tgc acc cag caa SEQ ID NO. 14 | 14631-14651 |
| Fragment h | | |
| E1GF | 5' ggc gcg cct aat acg act cac tat aga tga tgt gta ggg tat SEQ ID NO. 15 | 1-16 |
| E2968R | 5' cgc ggg cgc ctg agt tcg aca aat t SEQ ID NO. 16 | 2944-2968 |
| Fragment i | | |
| E14059F | 5' caa cga tcc tac cgc cgc aca a SEQ ID NO. 17 | 14059-14080 |

TABLE 1-continued

Primers used for RT-PCR amplification

| Primers | Sequences | Genome Position in SD01-08 |
|---|---|---|
| 018 Poly AR | 5' ggc gat cgg gcg tct agg aat tct aga (T)₄₁ aat ttc ggt cac<br>SEQ ID NO. 18 | 15036-15047 |
| 018 3' R | 5' ggc gat cgg gcg tct agg aat tc<br>SEQ ID NO. 19 | After polyA |

Unique restriction enzyme site construction in ORF7

| E14059F | 5' caa cga tcc tac cgc cgc aca a<br>SEQ ID NO. 20 | 14059-14080 |
|---|---|---|
| YFp503R | 5' ggc ccc agt gct gca atg ata c<br>SEQ ID NO. 21 | After polyA |
| Sca1F * | 5' aga aga aaa aga aaa gta c tg ctc caa tgg g<br>SEQ ID NO. 22 | 14569-14599 |
| Sca1R * | 5' ccc cat tgg agc agt act ttt ctt ttt ctt<br>SEQ ID NO. 23 | 14571-14600 |

GFP insertion in Nsp2 region

| gfpF | 5' gct cag atg gtg agc aag ggc gag gag c<br>SEQ ID NO. 24 | |
|---|---|---|
| gfpR | 5' gag tct gaa gag gac ttg tac agc tcg tcc a<br>SEQ ID NO. 25 | |
| Nsp2F1 | 5' tgc tga ctt tct tgc tga tcc acc tcc t<br>SEQ ID NO. 26 | 1895-1922 |
| Nsp2R1 | 5' cct tgc tca cca tct gag cac tcc cg<br>SEQ ID NO. 27 | 2408-2420 |
| Nsp2F2 | 5' gct gta caa gtc ctc ttc aga ctc caa ga<br>SEQ ID NO. 28 | 2419-2439 |
| Nsp2R2 | 5' gcg gac cca gcc agg atc aga c<br>SEQ ID NO. 29 | 2732-2753 |

* The nucleotide mutated for creating Sca1 restriction enzyme site is in bold and italics.

The 5' and 3' ends of the genome sequences were determined using a GeneRACER kit (Invitrogen) following the manufacture's instructions. The fragment representing the 5' terminus of the viral genome was prepared using RT-PCR with primers, E1GF and E2968R (Table 1), which integrates a T7 RNA polymerase site immediately preceding the authentic 5' terminal nucleotides and an Asc1 restriction enzyme site. The fragment containing the 3' end sequence was constructed by reverse transcription of RNA with primer 018 polyA, which is flanking the 41 polyA residues and Xbal site. The reverse transcription reaction was followed by PCR with primers E14059F and 018 3'R (Table 1).

Construction of a full-length cDNA clone of a North American Type 1 PRRSV and determination of its infectivity. A full-length genomic cDNA clone of a North American Type 1 PRRSV, pSD01-08 was constructed using the strategy shown in FIG. 1. A low copy number plasmid pACYC177 (GenBank Accession #X06402) was modified by replacing the fragment between the BamH1 and Bgl1 sites with a stuffer fragment, which was prepared as a synthetic gene containing the restriction enzyme sites as shown in FIG. 1. Each of the viral fragments was excised from PCR-Blunt II-Topo using restriction enzymes and ligated into the pACYC177 plasmid, which was digested with the same restriction enzymes. After each ligation step, the pACYC177 construct was transformed into E. coli DH5α cells and grown overnight at 37° C. in the presence of Kanamycin. The completely assembled full-length cDNA clone was sequenced, and the full-length genome sequence was deposited in GenBank under the accession number DQ489311.

To create the Sca1 restriction enzyme site, the silent mutation (G to T mutation) at nucleotide 42 of ORF7 (nucleotide 14588 of SD01-08 genome) was generated using site directed mutagenesis. Site directed mutagenesis was achieved by an overlapping extension PCR technique (Ho et al., 1989; Jespersen et al., 1997) using primer pairs E14059F/Sca1R and Sca1F/YFp503R. The mutated product was confirmed by DNA sequencing analysis.

This construct contains a bacteriophage T7 RNA polymerase promoter at the 5' terminus of the viral genome, one additional guanosine residue introduced between the T7 promoter and the first nucleotide of the viral genome, the 15047 nucleotides full-length genome of SD 01-08 and a poly (A) tail of 41 residues incorporated at the 3' end of the genome. Compared to the genome sequence of the parental virus, the DNA sequence of pSD0'-08 contained six nucleotide differences (Table 2).

TABLE 2

Nucleotide differences between the parental SD 01-08 isolate and the full-length cDNA clone.

| Nucleotide position within SD01-08 genome | Nucleotide in parental virus | Nucleotide in cDNA clone | Amino acid change | Gene position |
|---|---|---|---|---|
| 1331 | T | C | Silent | Nsp1β |
| 6158 | T | C | Silent | Nsp5 |
| 8191 | A | G | Silent | Nsp9 |
| 9492 | C | T | P to L | Nsp10 |
| 11261 | T | C | Y to H | Nsp11 |
| 14588 | G | T | Silent | ORF7 |

Four of these differences were silent mutations. The mutation at nucleotide 14588 was introduced to create a unique Sca1 restriction enzyme site into ORF7 for differentiating the cloned virus from parental virus. Two of the nucleotide mutations resulted in amino acid changes, which included the substitution of a C to T at nucleotide 9492 (amino acid P to L) located at Nsp10, and a T to C at nucleotide 11261 (amino acid Y to H) located at Nsp11.

Figure 2:
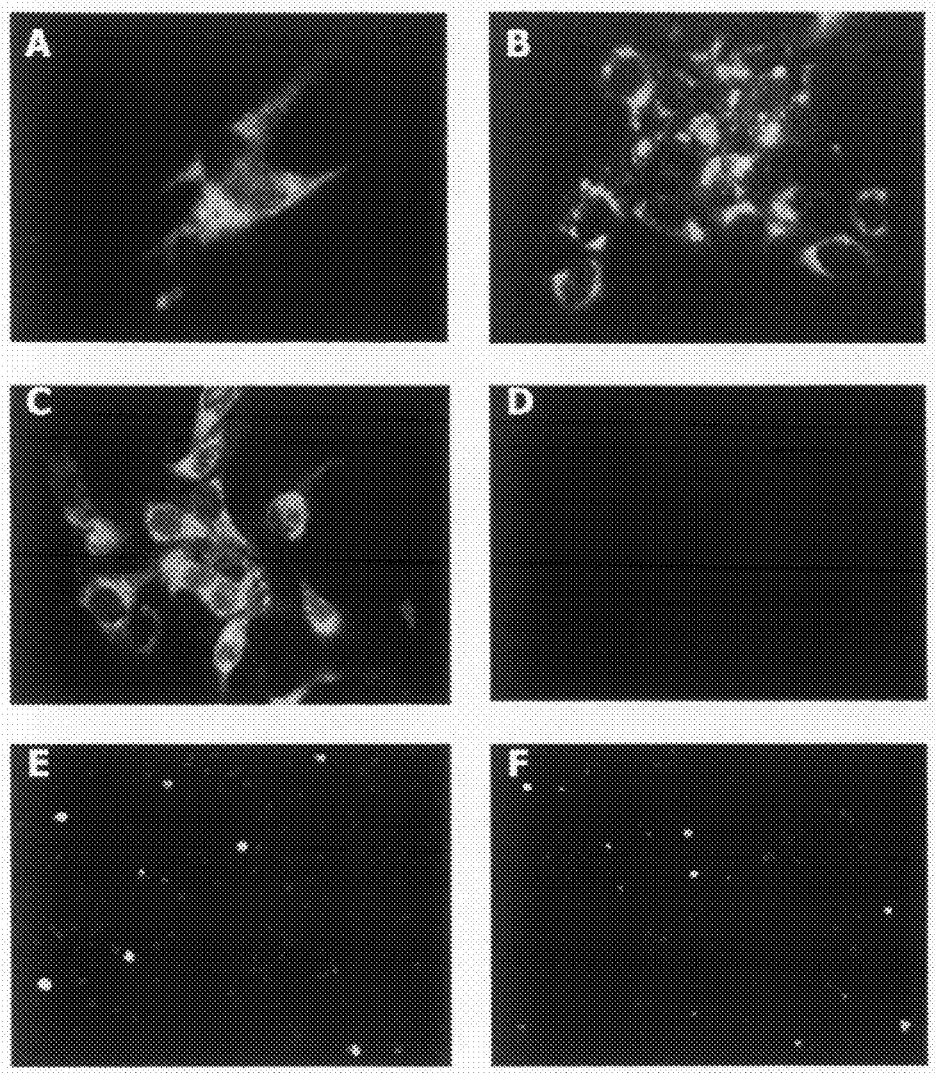
FIGS. 2A-2F depict results of immunofluorescence assays conducted to investigate the infectivity of infectious clone pSD01-08.

The plasmid pSD01-08 was linearized by restriction enzyme Xbal and used for in vitro transcription by T7 RNA polymerase to synthesize capped RNAs. The in vitro transcribed capped RNA was transfected into BHK-21 cells. At 48 hours post-transfection, cells were examined for the expression of N protein by fluorescent antibody staining with mAb SDOW17 (FIG. 2A). Results in FIG. 2A showed that about 5% of the transfected cells expressed the N protein. Supernatants from the transfected cells were passaged onto MARC-145 cells. After 72 hours, MARC-145 cells were stained using the SD01-08 specific, anti-Nsp2 mAb, ES3-4 58-46 (FIG. 2B), and anti-N mAb SDOW17 (FIG. 2C). A North American Type 2 PRRSV specific, anti-N mAb, MR39 (FIG. 2D), was incorporated as a negative control. The results showed that both Nsp2 and N proteins were detected in MARC-145 cells inoculated with supernatant from the pSD01-08 transfected BHK-21 cells. Upon further passage of the supernatant onto fresh MARC-145 cells (passage 2 on MARC-145 cells), cytopathic effects (CPE) were observed within 48 to 72 hours post infection (hpi). Titration of virus from passage 2 on MARC-145 cells showed an average titer of $3.6 \times 10^7$ FFU/ml. These results indicate that viable and infectious North American Type 1 PRRSV was rescued from the cells transfected with in vitro transcribed RNA.

GFP insertion: The pSD01-08-GFP clone was constructed by inserting the GFP gene sequence (Clontech) into the Nsp2 region (nucleotide 2420/2421) of the viral genome in the plasmid pSD01-08. The GFP gene was amplified from the pEGFP-N1 plasmid (Clontech) with forward primer gfpF and reverse primer gfpR. GFP was inserted by overlapping extension PCR technique (Ho et al.; 1989, Jesperson et al., 1997) using primer pairs of Nsp2F1/Nsp2R1 and Nsp2F2/Nsp2R2. The PCR product was digested with Rsrl1 and Acl1 restriction enzymes and ligated into the pSD01-08 plasmid, which was digested with the same restriction enzymes.

In vitro transcription and rescue of PRRSV: The plasmid, pSD 01-08 or pSD01-08-GFP was linearized with restriction enzyme XbaI. Capped RNA was transcribed with T7 RNA polymerase using the mMessage Machine kit (Ambion) and transfected to BHK-21 cells using DMRIE-C reagent (Invitrogen) following the manufacture's instructions. To rescue the virus, cell culture supernatant obtained 48 hours post-transfection was serially passaged on MARC-145 cells. Rescue of infectious virus was confirmed by indirect immunofluorescent assay (IFA) (Ropp et al., 2004). Monoclonal antibodies (MAbs) were developed for use in the IFA test, including MAb ES3-4 58-46, which specifically recognizes Nsp2 of SD01-08 (Fang et al., Conf. Res. Work. Anim, Dis., abstr. 78, 2004). MAb MR39 specifically recognizes the N protein of the North American Type 2 PRRSV and MAb SDOW17 recognizes the N protein of both genotypes of PRRSV (Nelson et al., 1993; Ropp et al, 2004). For rescue of GFP virus, the expression of GFP was also visualized directly under a fluorescent microscope.

Growth kinetics were examined by infecting MARC-145 cells with cloned virus and parental virus at a MOI of 0.1. Infected cells were collected at 0, 6, 12, 24, 36, 48, 60 and 72 hours post infection, and the virus titers were determined by IFA on MARC-145 cells and quantified as fluorescent focus unit per ml (FFU/ml). Plaque morphology between the cloned virus and parental virus was compared by plaque assay on MARC-145 cells. Confluent cell monolayers were infected with 0.1 MOI of viruses. After 2 hours, cell culture supernatant was removed and an agar overlay was applied. Plaques were detected after five days at 37° C., and stained by using 0.1% crystal violet.

In vitro characterization of cloned virus. The parental virus and cloned virus (passage 2 on MARC-145 cells) were titrated on porcine alveolar macrophages (PAMs). Immunofluorescent staining using anti-N mAb showed that both viruses replicated in PAMs (FIGS. 2E and 2F) and produced the similar virus yield ($2.1-2.8 \times 10^4$ FFU/ml) at 72 hpi.

Figure 3:
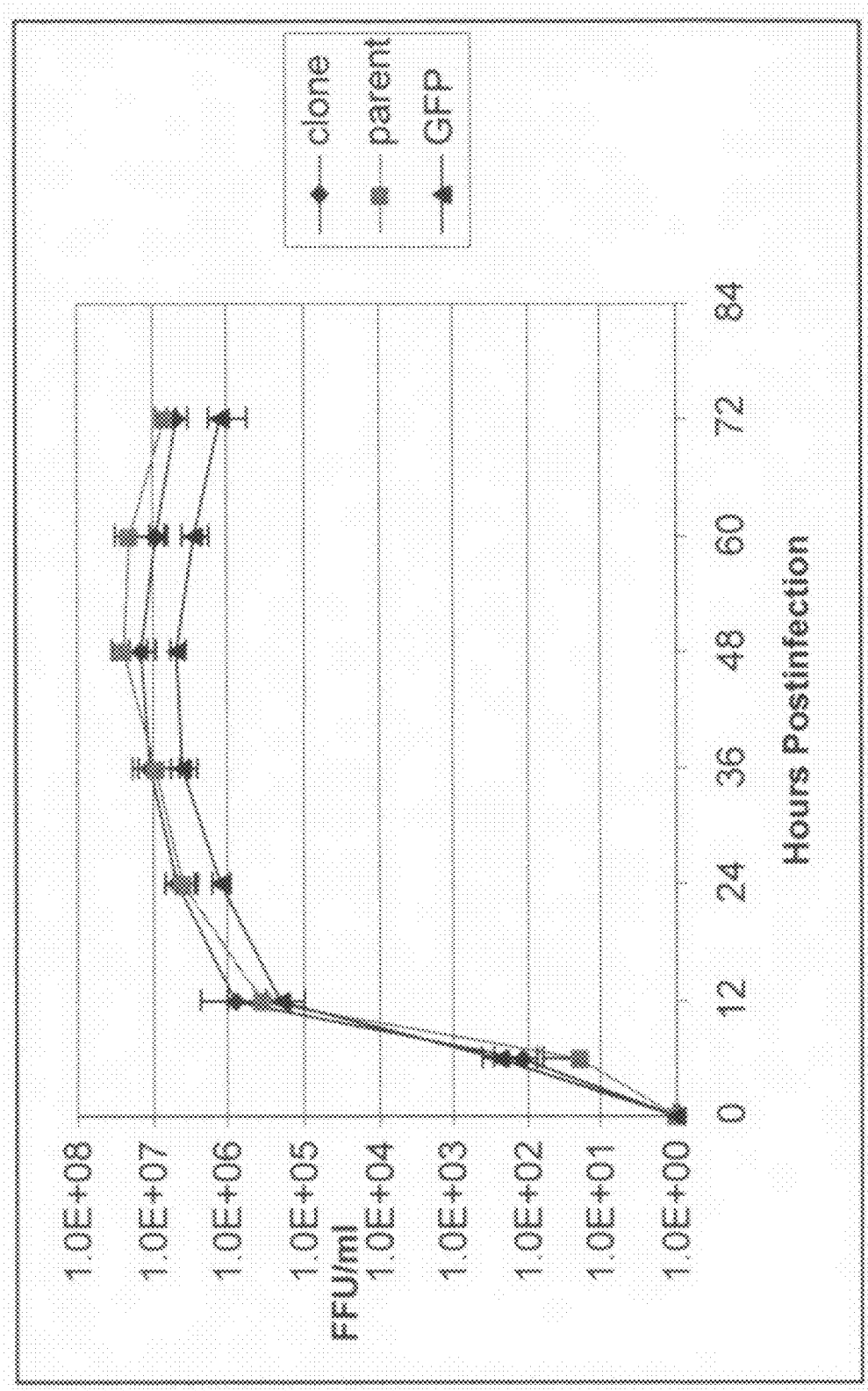
FIG. 3 is a graph showing growth kinetics of cloned virus, parental virus, and GFP-expressing virus.

To further compare the growth properties of the cloned and parental viruses, MARC-145 cells were infected with each of the viruses at a MOI of 0.1 and harvested at 6, 12, 24, 36, 48, 60, and 72 hpi. Growth curve results showed that cloned virus possessed similar growth kinetics with that of parental virus (FIG. 3). Titers peaked at 48 hpi for both viruses. The peak titer of the cloned virus was $1.39 \times 10^7$ FFU/ml, versus $2.34 \times 10^7$ FFU/ml for the parental virus. Plaque morphology of these viruses was also determined, the plaque size produced by cloned virus was similar to that of parental virus (data not shown). These results indicate that the cloned virus possesses in vitro properties similar to the parental wild-type virus.

Figure 4:
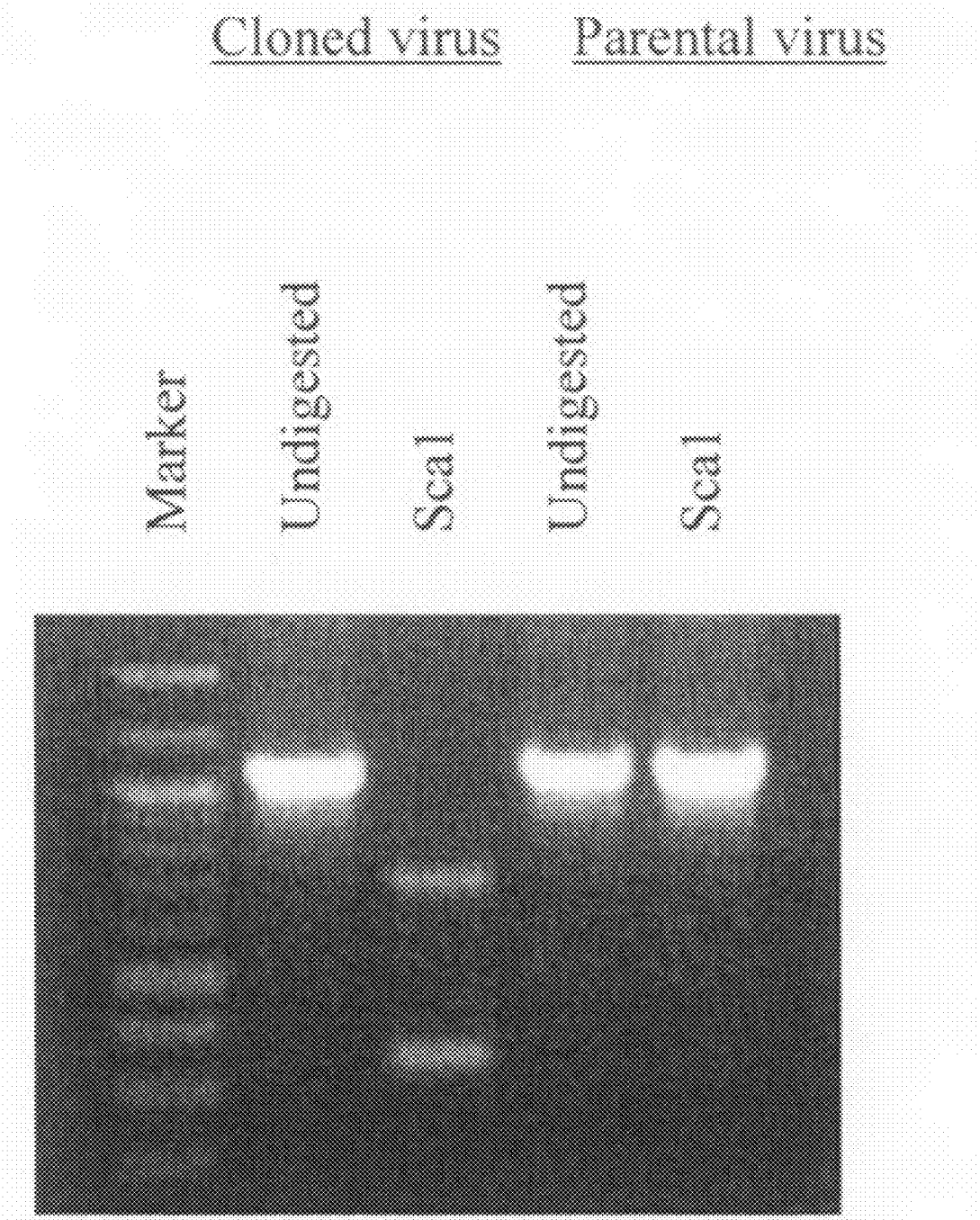
FIG. 4 depicts restriction endonuclease fragment patterns of the RT-PCR products of cloned and parental virus SD01-08.

To differentiate cloned virus from the parental virus, we engineered a Sca1 restriction enzyme site at nucleotide 42 of ORF7. As shown in FIG. 4, a 1054 by RT-PCR fragment derived from amplifying the nucleotides 13875 to 14928 was cleaved by Sca1 in the cloned virus. In contrast, the RT-PCR fragment derived from the parental virus was not cleaved by Sca1.

Pathogenic and immunological properties of cloned virus derived from pSD 01-08 in a pig model. An in vivo study of the replication properties of virus derived from the infectious clone using a nursery pig model was performed. Twenty-one 4 week-old, PRRSV naïve pigs from a certified PRRSV-negative herd were obtained and randomly divided into 4 groups housed separately in isolation facilities. After a 4 day acclimation period, pigs from each group (n=6 for cloned virus infected group; n=5 for the remaining groups) were inoculated intranasally with 1 ml $10^5$ TCID$_{50}$ of cloned virus (group 1) or parental virus (group 2). The third group of animals was inoculated with the current modified live virus (MLV) Ingelvac® PRRSV vaccine. The negative control group (group 4) animals were mock-challenged with MARC-145 cell culture supernatant.

Pigs were observed daily for clinical signs and body temperatures taken for the first 7 days after infection. Blood samples were obtained from all pigs on days 0, 7, 14, 21, 28, 35, and 42. Serum samples were stored at −80° C. for further tests. Two pigs from each group were euthanized at 21 days post inoculation (dpi) for post-mortem analysis of acute infection. The remaining three pigs from each group were euthanized at 42 dpi. Lung lesions of the study animals were evaluated using a previously developed system based on the approximate volume that each lobe contributes to the entire lung: the left and right apical lobes, the left and right cardiac lobes, and the intermediate lobe each contribute 10% of the total lung volume, the left and right caudal lobes each contributes 25%. These scores were then used to calculate the total lung lesion score based on the relative contribution of each lobe (Halbur et al., 1995).

For the detection of viral RNA and determination of viral load, serum samples from 0, 7, 14, 21, 28, 35, and 42 dpi were examined using a real-time, quantitative PCR (Tetracore VetAlert PRRS; Wasilk et al., 2004), which is routinely performed at the South Dakota Animal Disease Research and Diagnostic Laboratory (SDSU-ADRDL). All serum samples were evaluated for anti-PRRSV antibodies using the IDEXX HerdChek® PRRS 2XR ELISA and virus neutralization assay (VN). These tests are also routinely performed at SDSU-ADRDL under strict quality assurance guidelines.

Figure 5A:
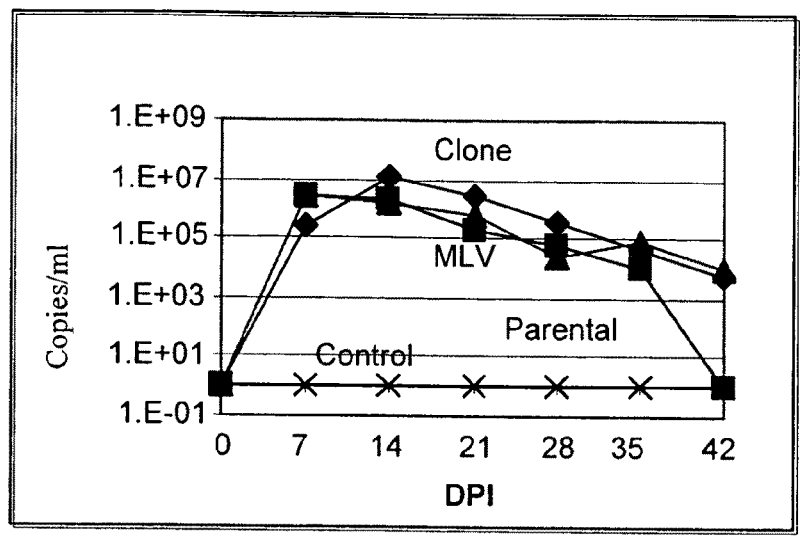
FIGS. 5A and 5B are graphs showing in vivo characterization of cloned virus.
Figure 5B:
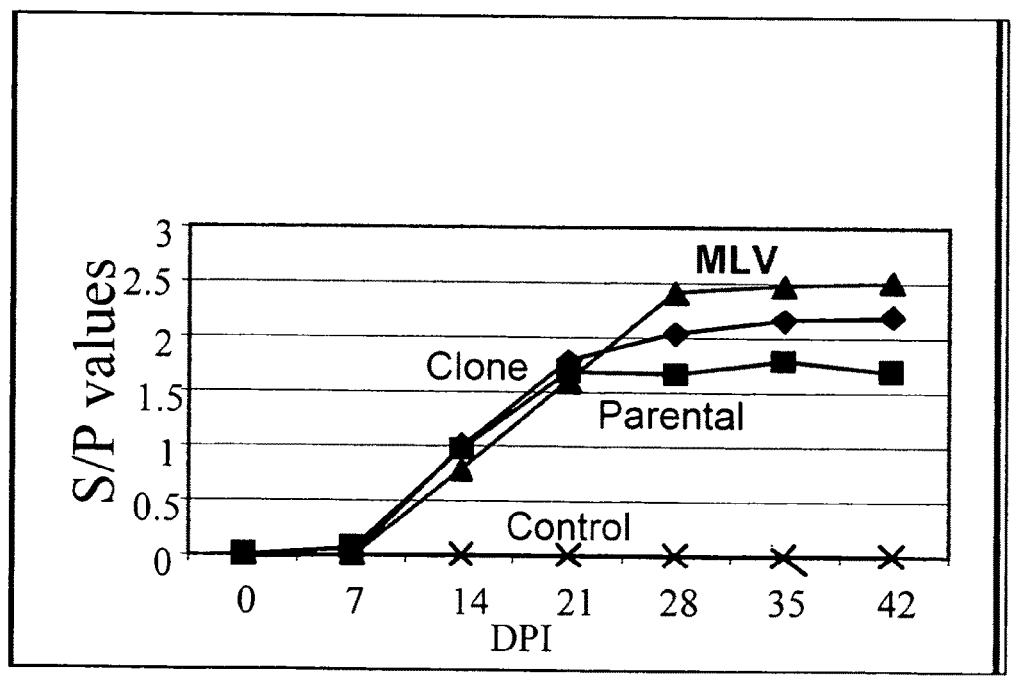

All pigs that received viruses became infected, which was evident by positive RT-PCR results for the presence of viral RNA in serum and by serology. Virus in serum peaked at about 14 days post-infection (dpi) (FIG. 5A; Table 3). At 14 dpi, 5 of 6 pigs in the cloned virus group, 4 of 5 pigs in the parental virus group, and all 5 pigs in the vaccine groups had seroconverted (FIG. 5B; Table 3). Four of the 6 pigs in the cloned virus challenged group had detectable neutralizing antibody titers at 21 dpi, while 1 of the 5 pigs in the parental challenged group developed neutralizing antibodies by 21 dpi. Two of the pigs from the MLV vaccine challenged group developed detectable neutralizing antibody titers at 42 dpi (Table 3).

TABLE 3

Summary of serological and PCR results in serum of inoculated pigs at different days post infection (dpi).

| | Parental virus | | | Cloned virus | | | MLV vaccine | | |
|---|---|---|---|---|---|---|---|---|---|
| dpi | PCR[a] | ELISA[b] | VN[c] | PCR[a] | ELISA[b] | VN[c] | PCR[a] | ELISA[b] | VN[c] |
| 0 | 0/5 | 0/5 | 0/5 | 0/6 | 0/6 | 0/6 | 0/5 | 0/5 | 0/5 |
| 7 | 4/5 | 1/5 | 0/5 | 5/6 | 0/6 | 0/6 | 5/5 | 0/5 | 0/5 |
| 14 | 4/5 | 4/5 | 0/5 | 6/6 | 5/6 | 0/6 | 5/5 | 5/5 | 0/5 |
| 21* | 5/5 | 5/5 | 1/5 | 6/6 | 5/6 | 4/6 | 5/5 | 5/5 | 0/5 |
| 28 | 2/3 | 3/3 | 2/3 | 4/4 | 4/4 | 2/4 | 3/3 | 3/3 | 0/3 |
| 35 | 1/3 | 3/3 | 2/3 | 2/4 | 4/4 | 2/4 | 3/3 | 3/3 | 0/3 |
| 42 | 0/3 | 3/3 | 3/3 | 1/4 | 4/4 | 2/4 | 2/3 | 3/3 | 2/3 |

[a]PCR: number of pigs with a PCR positive/total number of pigs in each group determined by the real time PCR;
[b]ELISA: number of seropositive pigs/total number of pigs in each group determined by IDEXX HerdChek ® PRRS 2XR ELISA;
[c]VN: number of pigs developing neutralizing antibody response/total number of pigs, determined by fluorescent focus neutralization assay. Results interpreted as 90% reduction of the viral infection.
*Two pigs euthanized at day 21 for analysis of acute infection.

All mock-infected pigs remained RT-PCR and PRRSV antibody negative throughout the study period. No significant clinical signs were observed in any of the infected pigs. Only mild pathological lung lesions characteristic of PRRSV, such as minor interstitial pneumonia, were observed in 3 of 6 pigs from the cloned virus group, 5 of 5 pigs from the parental virus group and 2 of 5 pigs from the vaccine group. The rest of the pigs did not show gross lung lesions (Table 4). Interestingly, in comparing to the pathological lesions among the pigs from different groups, the lesion scores appear slightly higher in pigs infected with parental virus.

TABLE 4

Percentage of lung with gross pneumonia lesions in infected pigs.

| | Gross lung lesion score (%)* | | | |
|---|---|---|---|---|
| Pig number | Cloned virus | Parental virus | MLV vaccine | Mock control |
| #1 | 0 | 0.6 | 0.7 | 0 |
| #2 | 1.0 | 0.5 | 0 | 0 |
| #3 | 0.9 | 10.5 | 0 | 0 |
| #4 | 0 | 2.1 | 0.3 | 0 |
| #5 | 0 | 3.25 | 0 | 0 |
| #6 | 1.5 | N/A | N/A | N/A |

*Gross lung pathology was assessed by using a gross pig lung lesion scoring system where each lobe of the lung was evaluated for % pneumonia, and the % pneumonia of each lobe was added for entire lung (10).

Figure 6:
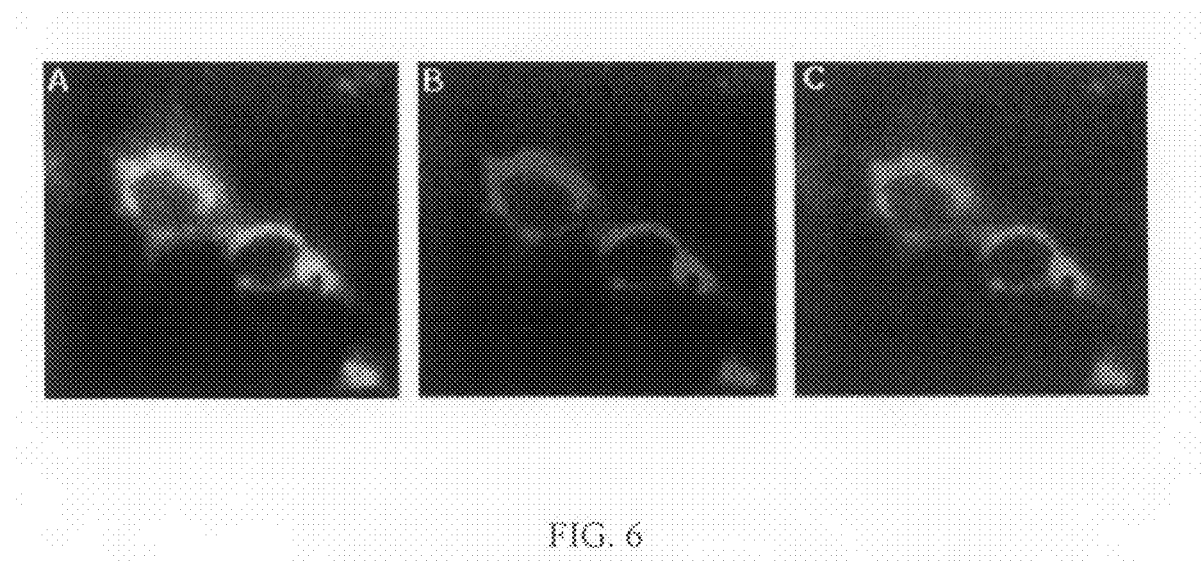
FIGS. 6A-6C depict the results of immunofluorescence assays conducted to investigate GFP-expressing PRRSV.
Figure 7:
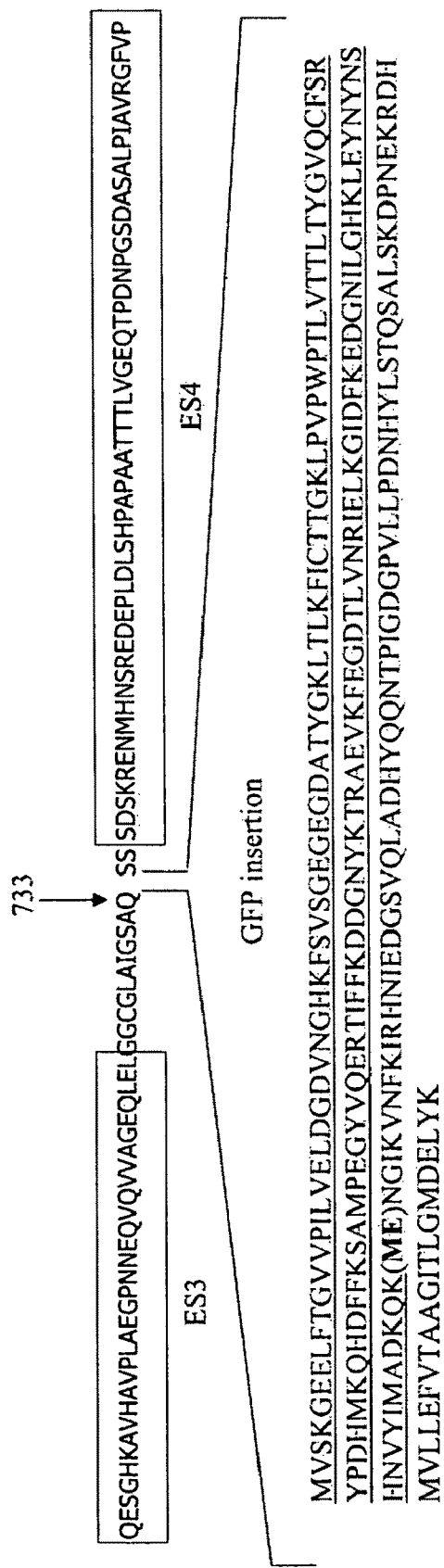
FIG. 7 is a schematic representation of the pSD01-08-GFP construct (SEQ ID NOS: 30 and 31).

Introduction of green fluorescent protein into the Nsp2 region of the infectious clone. We explored the potential of using this infectious clone for foreign gene expression. Previous studies showed that Nsp2 is an excellent candidate site for foreign gene insertion. The C-terminal region of Nsp2 for both Type 1 and Type 2 contains hypervariable domains, including amino acid insertions and deletions (7, 8, 27). One of the major differences between the SD01-08 and LV, the prototypic member of European Type 1 viruses, is the presence of a 17 amino acid deletion in the Nsp2, which is located between amino acids 734 to 750 in ORF1 of LV. We inserted a green fluorescent protein (GFP) into this unique deletion site of Nsp2 (at amino acids 733/734 of SD01-08 ORF1a, FIG. 7). The construct, pSD01-08-GFP was in vitro transcribed and transfected into BHK-21 cells. Live cells were examined directly under a fluorescence microscope after 48 hours post-transfection. The cell culture supernatant from transfected BHK cells was passaged onto MARC-145 cells, resulting in the appearance of GFP-expressing cells, which could be clearly visualized as early as 6 hours after infection (FIG. 6A). To confirm the expression of GFP-Nsp2 fusion protein, at 48 hours post-infection, cells were fixed and stained with an Nsp2 specific mAb ES3-4 58-46. ES3-4 58-46 was generated by immunizing mice with synthetic peptide made from ES3 epitope sequence, which is located immediately up-stream of the GFP insertion site (FIG. 7). A red fluorescent Cy3-conjugated goat anti-mouse IgG was used as secondary antibody. Confocal microscopy showed the perinuclear localization of both GFP and Nsp2, similar to Nsp2 localization of the parental virus (FIGS. 6B and 6C). To determine if the expression of GFP affected virus replication, the growth characteristics of the GFP virus were compared to the parental wild-type and cloned viruses. The replication cycle of the pSD01-08-GFP virus was similar to the other viruses, including peak viral titers at 48 hpi; however, the peak titer for the GFP virus infection was approximately 10 fold reduced (FIG. 3).

To investigate the stability of GFP expression over multiple rounds of virus replication, the GFP virus was serially passaged eight times on MARC-145 cells. By the seventh passage, there appeared a subpopulation of non-GFP expressing virus, which was counted as 15% of the total virus population. The loss of GFP was also analyzed by RT-PCR. Total cellular RNA was isolated from cells infected with the seventh passage of the GFP virus, and RNA was used as a template in a RT-PCR reaction with primers that amplified the GFP insertion region. The RT-PCR product was cloned and sequenced. The results revealed that the N-terminal amino acids 1-159 of GFP were deleted (FIG. 7). More interestingly, while the amino acids 1-159 were deleted, two amino acids, methionine (M) and glutamic acid (E) were inserted by the virus before the GFP amino acid 160 (FIG. 7). Therefore, the selection of viral genome encoding the deletion in the GFP gene accounted for the decline in the percentage of infected cells expressing GFP. Taken together, these results indicate that the Nsp2 region can tolerate the introduction of a foreign gene. However, inserting a foreign gene reduces the level of viral replication. The positive marker, GFP gene was thus not stable.

II. Negative Marker Virus GFP/ΔES4

Figure 8:
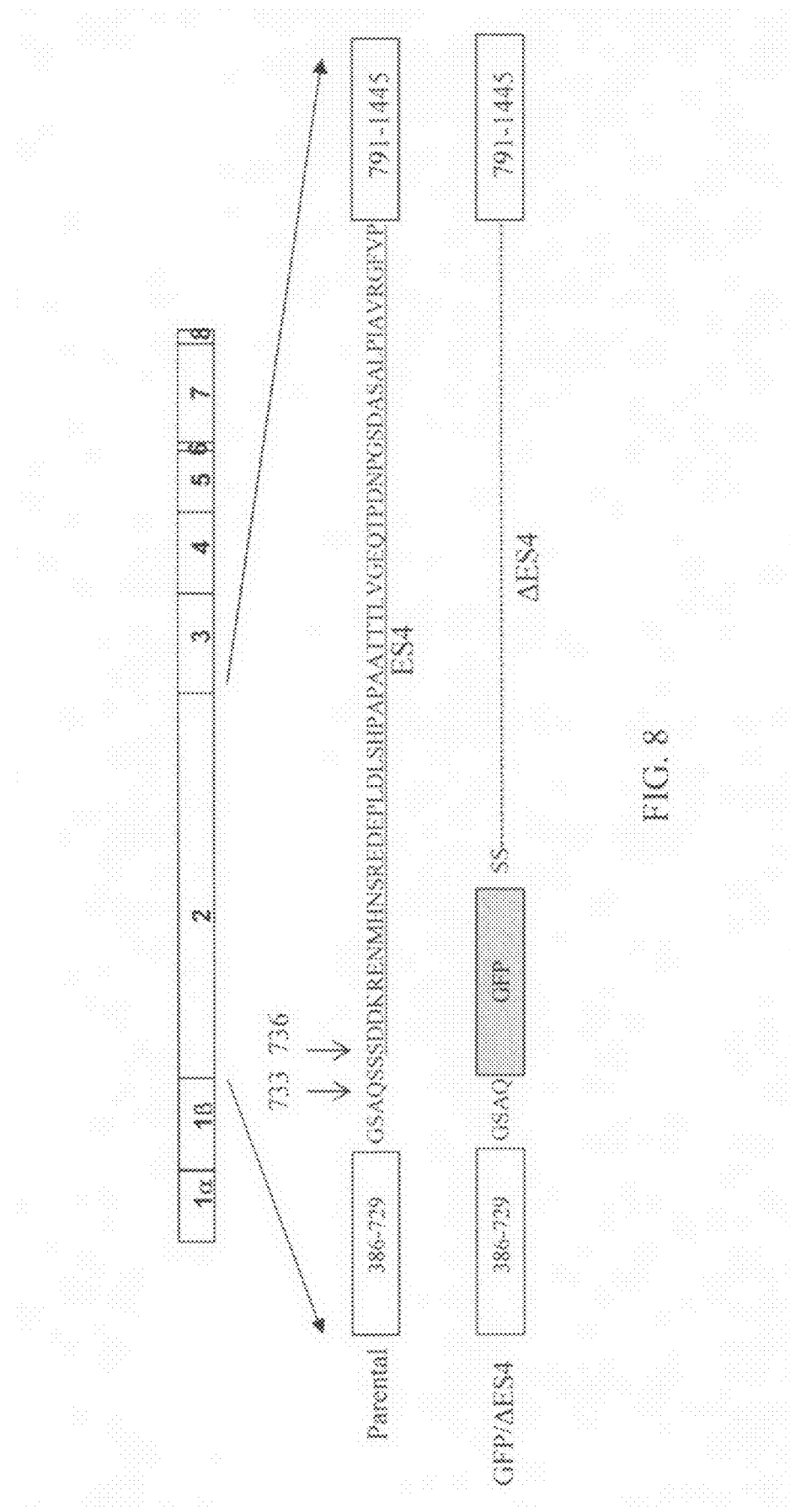
FIG. 8 is a schematic representation of the pSD01-08-GFP/ΔES4 construct (residues 40-100 and 40-45 of SEQ ID NO: 30).
Figure 9:
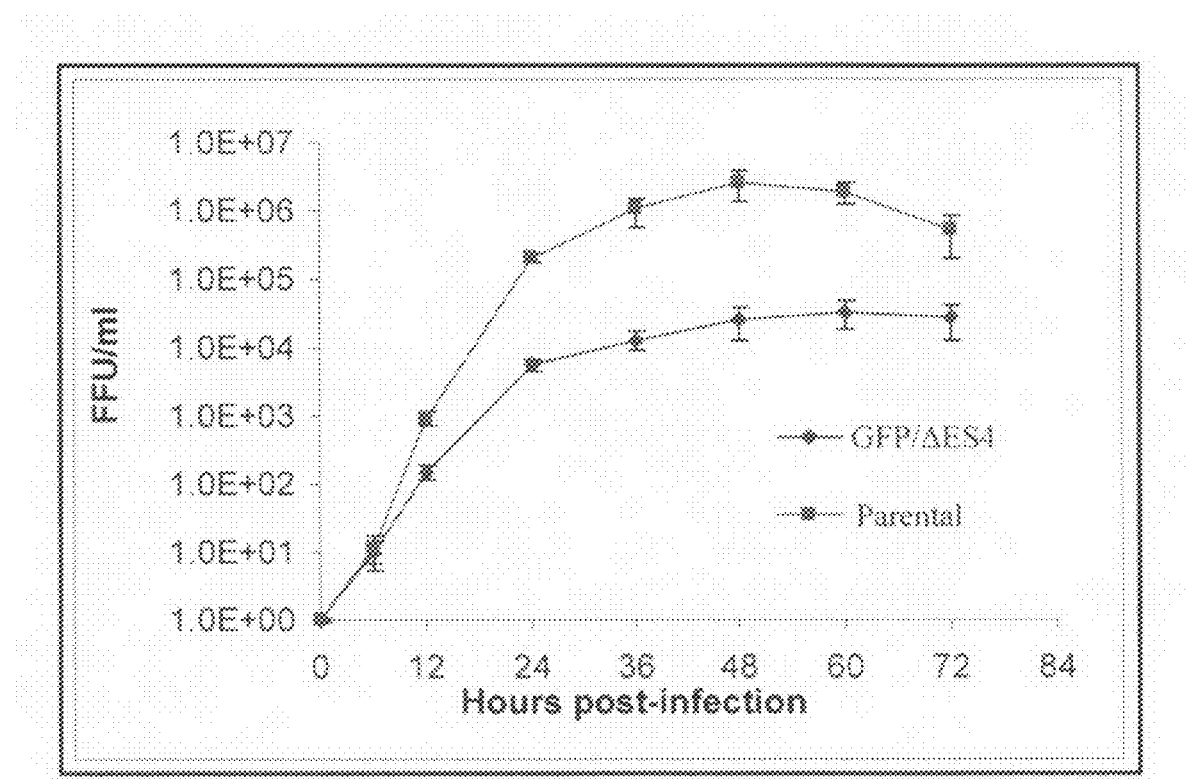
FIG. 9 is a graph showing growth kinetics of GFP/ΔES4 marker viruses.
Figure 10:
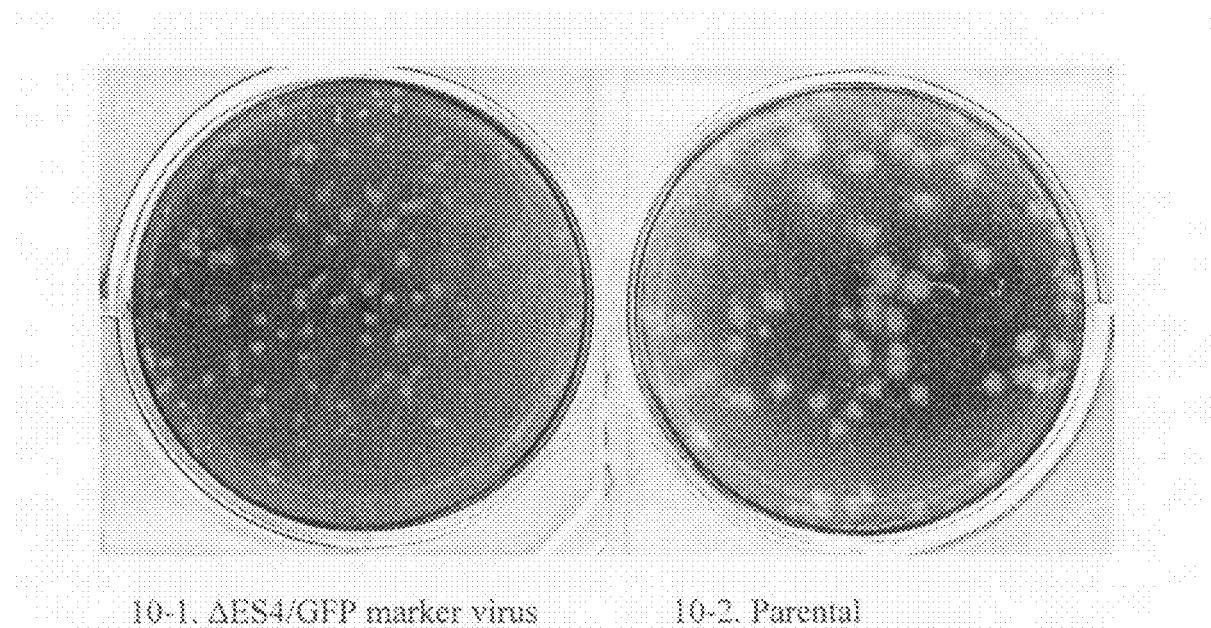
FIG. 10 depicts plaque morphology of GFP/ΔES4 marker viruses and parental viruses.

GFP/ΔES4 negative marker vaccine virus construction. In order to obtain a potential negative marker vaccine virus, the B-cell epitope, ES4, that is located downstream of the GFP (at nucleotide 2427 to 2591 of SD01-08 viral genome) was deleted by overlapping extension PCR techniques (Hayashi et al., 1994) using primer pairs ΔES4F/E3448R and E1895F/ΔES4R (Table 5). The PCR product was digested with Rsrll and EcoRV restriction enzymes and ligated into the pSD01-08-GFP plasmid, which was digested with the same restriction enzymes. The resulting plasmid construct is designated as pSD01-08-GFP/ΔES4 (FIG. 8).

TABLE 5

Primers used for ES4 epitope deletion and ELISA antigen expression.

| Primer name | Sequence* | Genome position in SD01-08® |
|---|---|---|
| ΔES4F | 5' caa gtc ctc tac agg gcc cat act c SEQ ID NO. 32 | 2421-2426 2592-2606 |
| ΔES4R | 5' ggc cct gta gag gac ttg tac agc tc SEQ ID NO. 33 | 2421-2426 2592-2599 |

TABLE 5-continued

Primers used for ES4 epitope deletion and ELISA antigen expression.

| Primer name | Sequence* | Genome position in SD01-08® |
|---|---|---|
| E1895F | 5' ctt gct gat cc acct cct cag g<br>SEQ ID NO. 34 | 1905-1926 |
| E3448R | 5' ccg tcg gag ggg gtg gca tcc<br>SEQ ID NO. 35 | 3377-3397 |
| Nsp2-2144F | 5' gtc tgt gtc ctt gga cga gtg<br>SEQ ID NO. 36 | 2144-2164 |
| Nsp2-2694R | 5' cca agc ggc caa gga tag atc<br>SEQ ID NO. 37 | 2694-2714 |
| pET-EGFP-F | 5' cg*g gat cc***a tgg tga gca agg gcg agg agc**<br>SEQ ID NO. 38 | — |
| pET-EGFP-R | 5' cct *aag ctt* cct tgt aca gct cgt cca tgc cg<br>SEQ ID NO. 39 | — |
| pET-ES4F1 | 5' gc *aga tct* tca gac tcc aag aga gaa<br>SEQ ID NO. 40 | 2427-2444 |
| pET-ES4F2 | 5' gc *aga tct* ggt ggt ggt ggt tcc tca gac tcc aag aga gaa<br>SEQ ID NO. 41 | 2427-2444 |
| pET-ES4R | 5' at ccc *aag ctt* gcg g*gg atc c*cg gga caa atc ctc g<br>SEQ ID NO. 42 | 2577-2591 |

*Nucleotides of GFP are bolded, restriction enzyme sites are italicized and underlined;
®Numbers correspond to nucleotide positions within the SD01-08 genome.

FIG. 8 is a schematic diagram of the pSD01-08-GFP/ΔES4 construct. The GFP was inserted between amino acids 733 and 734 of ORF1a, and the immunogenic B-cell epitope, ES4, located downstream of GFP (at amino acid 736 to 790) was deleted from SD01-08 virus. Direct transfection of this plasmid DNA into BHK-21 cells initiates a full cycle of virus replication. Cell culture supernatants from BHK-21 cells obtained 48 hours post-transfection were passaged onto MARC-145 cells, infectious progeny virus was recovered, and the resulting virus was designated as GFP/ΔES4 marker virus. The parental virus, SD01-08, was generated in parallel from the pSD01-08 cDNA clone. Passage two of the viruses from MARC-154 cells was used for in vitro and in vivo characterization.

Growth kinetics study showed that GFP/ΔES4 marker viruses replicated with slightly slower kinetics, reaching maximal titer several hours later than the parental virus, SD01-08. The peak viral titer of the marker virus ($3.34\times10^4$ FFU/ml) was approximately two logs lower titer than that of the parental virus ($2.56\times10^6$ FFU/ml) (FIG. 9). FIG. 9 depicts growth kinetics of GFP/ΔES4 marker viruses. MARC-145 cells were infected in parallel at MOI of 0.1 with the passage three of GFP/ΔES4 marker virus and parental virus. At 0, 6, 12, 24, 36, 48, 60, and 72 hours post infection, cells were harvested and the virus titers were determined by IFA on MARC-145 cells. The results were mean values from three replications of the experiment, and viral titers were expressed as fluorescence focus units per milliliter (FFU/ml). Plaque morphology between the marker virus and parental virus was compared by plaque assay on MARC-145 cells. Viral plaques formed by GFP/ΔES4 marker virus were drastically reduced in size, and most plaques were of pinpoint size (FIG. 10), suggesting a negative effect of the GFP insertion/ES4 deletion on the rate of cell-to-cell spread during infection. FIG. 10 shows plaque morphology of GFP/ΔES4 marker viruses (10-1) and parental viruses (10-2). Confluent cell culture monolayers were infected with viruses at a MOI of 0.1. After 2 hours infection, cell culture supernatant was removed and an agar overlay was applied. Plaques were detected after 5 days at 37° C. and stained by using 0.1% crystal violet.

In vitro stability of the GFP insertion or ES4 deletion in the recombinant viruses was followed for 10 serial passages (72 hours incubation for each passage) in MARC-145 cells. The GFP/ΔES4 region of the virus at passage 10 was sequenced. Surprisingly, unlike the previous SD01-08-GFP virus which experienced a deletion of the N-terminal 159 amino acids, the GFP in the GFP/ΔES4 marker virus remained intact as a full-length gene, and the ES4 deletion was still present. This result indicates that deletion of the ES4 epitope region improved the stability of the inserted foreign gene, GFP. A small population of the infected cells was identified that lost the GFP-associated fluorescence (FIG. 11). GFP expression in MARC-145 cells infected with passage 10 of the GFP/ΔES4 marker viruses is shown in 11-1. The same viral focus stained with AlexiFluor-labeled anti-nucleocapsid monoclonal antibody, SDOW17 (Nelson et al., 1993) is shown in 11-2. The population of viruses that lost GFP fluorescence is shown in the circle.

For the GFP/ΔES4 region, we performed three independent repeats of PCR and sequencing (both forward and reverse directions). Therefore, a total six sequences were obtained. In one of the sequences, a nucleotide C-289 to T-289 mutation was identified, which caused the amino acid mutation of arginine to cysteine at position 97 of the GFP, which may correspond to the small population of infected cells that lost the GFP-associated fluorescence (FIG. 12). No mutation was detected on the other five sequences. FIG. 12 depicts an electrophoregram of the wild-type GFP gene in comparison to the Arg-97 mutated GFP gene. The GFP insertion region was sequenced from cell culture passage 10 of the GFP/ΔES4 marker viruses. Amino acids are presented in a single letter code, and the bold letter indicates mutated amino acid from CGC (Arg) to TGC (Cys).

ES4 and GFP antigens expression. The ES4 antigen was expressed as tandem repeat ES4 epitopes using a modified method described previously (Sun et al., 2004). Briefly, three copies of the ES4 epitope (amino acid 736-790 of ORF1a of SD01-08), were constructed in protein expression vector, pET-28a(+)(Novagen). A flexible peptide linker, GGTGGTGGTGGTTCC (SEQ ID NO: 48), was added between the epitopes to help display the epitopes. There were two forward primers. Forward primer 1, pET-ES4F1 contained BglII restriction site, but without a linker sequence, whereas the forward primer 2, pET-ES4F2 contained not only a BglII restriction site, but also the linker sequence. The ES4 gene fragment was first amplified with the forward primer 1 and reverse primer, pET-ES4R. The PCR product was digested with BglII and HindIII, and then cloned into pET-28a that was digested with BamHI and HindIII. This clone was designated as pET-28a-ES4(+1). The second copy of ES4 was PCR amplified by forward primer 2 and reverse primer, pET-ES4R. The PCR product was digested with BglII and HindIII, and then cloned into pET-28a-ES4(+1) that was digested with BamHI and HindIII. The third copy of the ES4 was inserted using the same strategy as the second copy. The final construct was designated as pET-28a-ES4(+3). The GFP gene was amplified from the pEGFP-N1 plasmid (Clontech) with primer pair pET-EGFP-F/pET-EGFP-R. The PCR product was digested by BamHI and HindIII restriction enzymes and ligated to the pET-28a vector that was digested with the same enzymes. Recombinant proteins were expressed in E. coli BL21 (DE3) to produce a fusion protein with six histidine residues at the N-terminal. The proteins were purified by nickel-affinity chromatography and analyzed by SDS-PAGE as described in our previous publication (Ferrin et al., 2004).

In vivo characterization of GFP/ΔES4 marker virus. The in vivo characteristics of the GFP/ΔES4 marker virus were studied in a nursery pig disease model. Eighteen four-week-old pigs were purchased from a PRRSV-free herd. The animals were randomly separated into three groups (n=6/group) and housed under BL2 isolation conditions with an acclimation period of 7 days before starting experimental inoculations. Group 1 pigs were infected with GFP/ΔES4 marker virus, the group 2 pigs were infected with parental SD01-08 virus as the positive control, and group 3 pigs were mock-infected with the cell culture medium. Group 1 and group 2 pigs were inoculated through both intranasal and intramuscular sites with $1\times10^6$ 50% tissue culture infective doses (TCID$_{50}$) of the virus (1 ml at each site). On 42 days post infection (dpi), group 1 and group 2 pigs were challenged with a heterologous Type 1 strain, SD03-15 virus.

The SD03-15 is another US Type 1 strain, which was isolated from clinical samples submitted to our diagnostic laboratory in 2003. In field reports, pigs infected with SD03-15 were experiencing a pre-weaning mortality of 80-90% for a 3-week period. Decreased performance continued through the finisher phase. In the adult sow population, there was a mild abortion storm, compared to previous US PRRSV outbreaks. Our previous experimental animal study also demonstrated the pathogenic nature of this virus (Lawson et al., Proc. Conf. Res. Work. Anim. Dis., abstr. 99, 2005).

Figure 13:
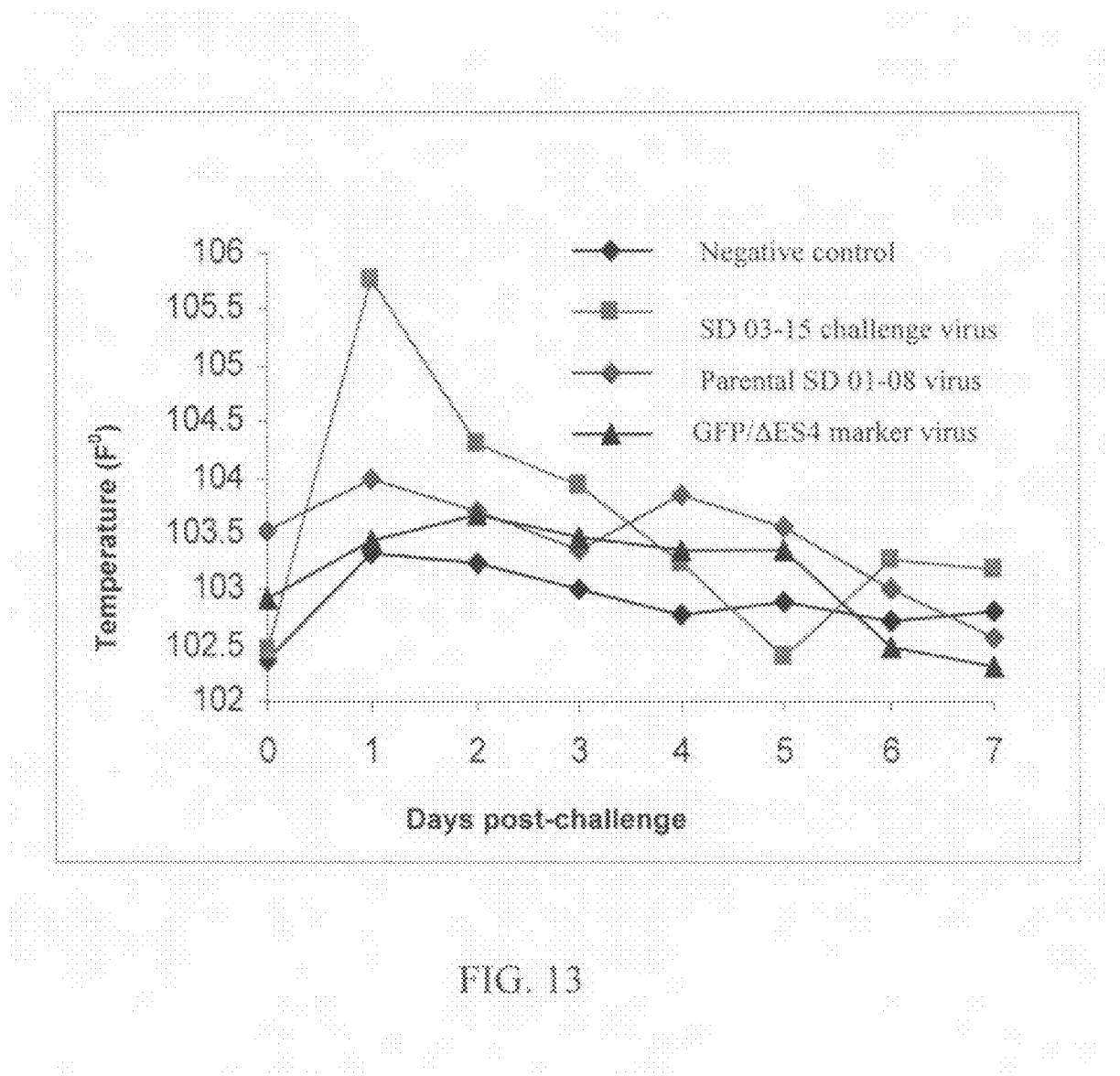

Three pigs from group 3 were challenged with SD03-15 virus, and the other three pigs remained as mock-infected controls. Pigs were observed daily for clinical signs and body temperatures for the first 7 days after infection and the first 7 days after challenge. Mean temperature responses between different challenge groups were compared. Rectal temperatures were taken one day before challenge, and 7 days after challenge. No temperature increase was detected in any pigs after initial infection and no clinical signs were observed. After challenge, rectal temperatures were elevated in those three challenged pigs from Group 3 (initially mock infected) at one and two days post challenge (FIG. 13). Clinical signs (coughing and nasal discharge) were also observed in these three pigs. The rest of the pigs remained asymptomatic. Blood samples were obtained once per week from all pigs. Pigs were euthanized at 21 days post challenge. Gross lung lesions of the study animal were evaluated using a previously developed system based on the approximate volume that each lobe contributes to the entire lung: the left and right apical lobes, the left and right cardiac lobes, and the intermediate lobe each contribute 10% of the total lung volume, and the left and right caudal lobes each contribute 25%. These scores were then used to calculate the total lung lesion score based on the relative contributions of each lobe (Halbur et al., 1995). At necropsy, gross pathologic lesions were not observed in Group 1, Group 2, and the three strict negative control pigs. In contrast, mild gross pathologic lung lesions characteristic of PRRSV were observed in those three pigs from Group 3 that were initially mock infected and then challenged with SD03-15.

Figure 14A:
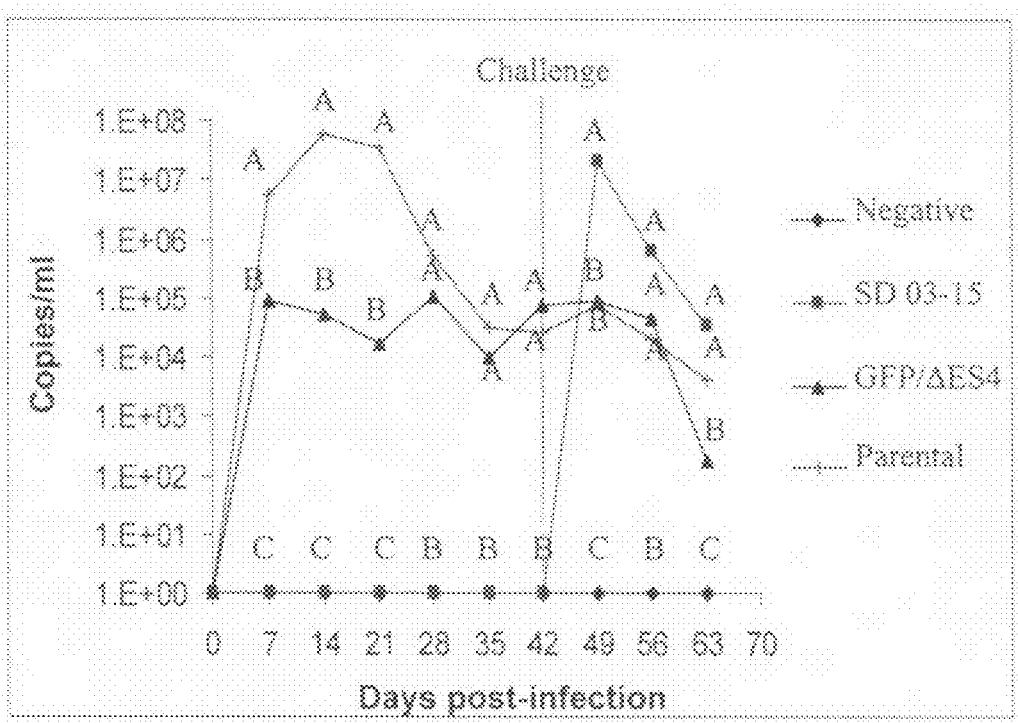

Virological and immunological properties. In vivo virological and immunological properties of the marker virus were determined. Pigs were challenged at 42 dpi, shown as a vertical dotted line in FIGS. 14A-14C. The duration and height of viremia was determined by real-time PCR, and the result was interpreted as RNA copy numbers per ml. At each day post-infection, mean viral load with different capital letters (A, B or C) differ significantly (P<0.05). In comparison to Group 2 pigs infected with parental viruses (peak mean viral titer=$5.9\times10^7$ copies/ml), pigs that were infected with the GFP/ΔES4 marker virus had lower peak viral load (peak mean viral titer=$2.08\times10^5$ copies/ml, FIG. 14A). At day 7 post-challenge, the viral load was two to three logs lower for the pigs vaccinated than those pigs initially mock infected and then challenged with SD03-15 virus. By day 21 post-challenge, GFP/ΔES4 marker virus infected-group pigs had a 10-fold lower viral load in comparison to the parental group, and 3/5 pigs had eliminated the virus in the serum (FIG. 14A; Table 6).

TABLE 6

Viral load in serum measured by quantitative PCR at 21 days post-challenge with a genetically different strain, SD03-15.

| | Viral load in serum (copies/ml) | | | |
|---|---|---|---|---|
| Pig numbers | GFP/ΔES4 | Parental | Negative/challenged* | Negative |
| 1 | 0 | 2.7E+02 | N/A | 0 |
| 2 | 7.4E+02 | 0 | N/A | 0 |
| 3 | 0 | 1.2E+04 | N/A | 0 |
| 4 | N/A | 0 | 3.6E+04 | N/A |
| 5 | 0 | 2.6E+03 | 3.3E+04 | N/A |
| 6 | 1.7E+02 | 1.1E+04 | 3.6E+04 | N/A |
| Mean | 1.8E+02 | 4.3E+03 | 3.5E+04 | 0 |

*Three of the pigs in negative group challenged with the heterologous strain, SD 03-15 at 42 dpi.

By 14 dpi, all of the pigs in infected groups had seroconverted. PRRSV-specific serum antibodies were measured by an IDEXX HerdChek® PRRSV ELISA 2XR kit. S/P ratios of greater than 0.4 are considered positive. The antibody response reached similar levels after 21 dpi (FIG. 14B).

Figures 14B, 14C:
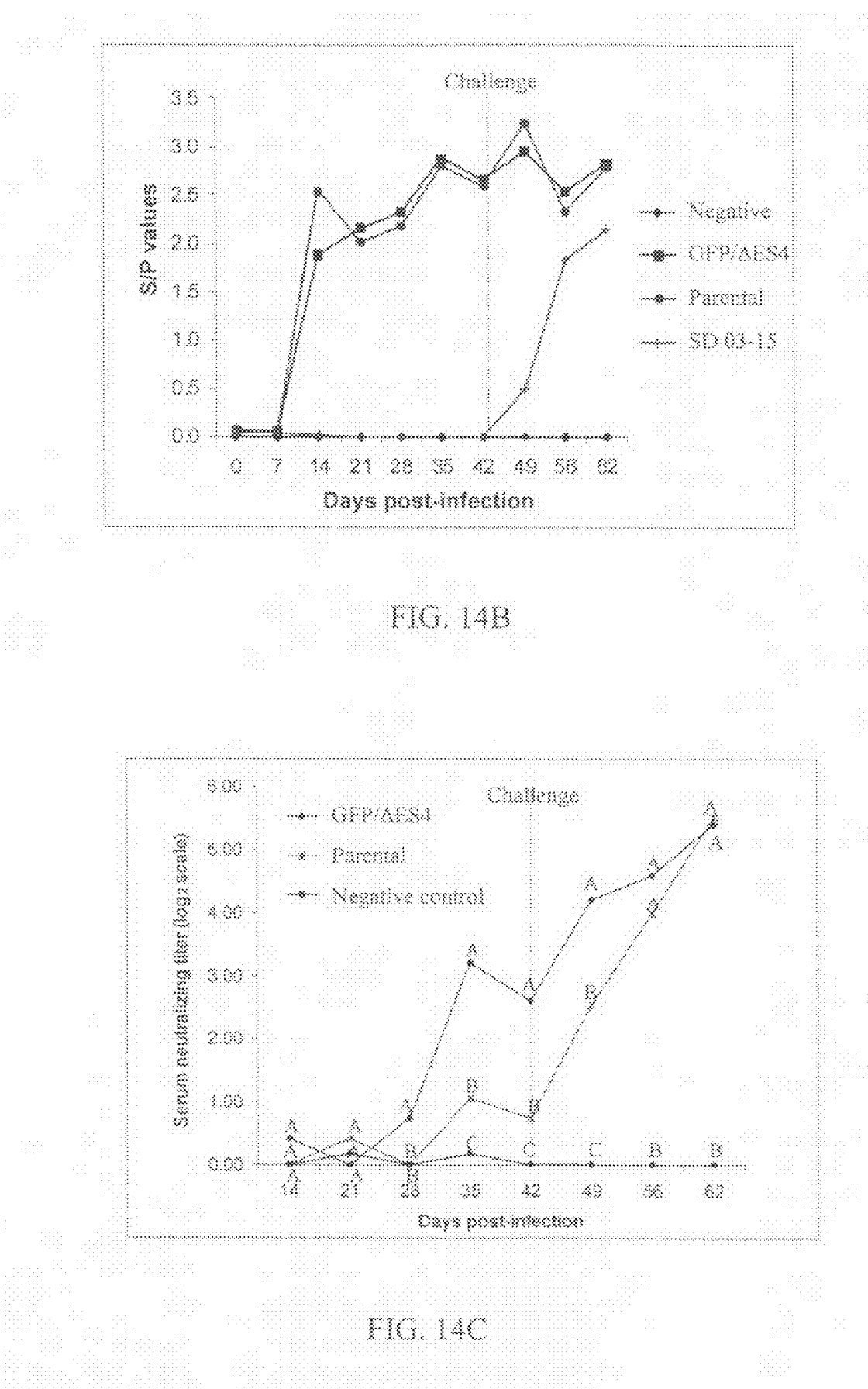

Viral neutralizing antibody response was determined by fluorescent focus neutralization assay (FIG. 14C). Results were interpreted as a 90% reduction of the viral infection, and the neutralizing antibody titers were presented as mean value (n=6) and expressed on a log$_2$ scale. The parental SD01-08 virus was used for the viral neutralizing assay. At each day post-infection, means with different capital letters (A, B or C) differ significantly (P<0.05). Further measurement of the serum neutralizing (SN) antibody levels showed that in pigs infected with the parental virus, SN antibodies were detected from one of the six pigs by 21 days post-infection, and 3/6 pigs developed detectable SN titer that reached an average geometric mean titer (GMT) of 2 by 35 days post-infection. In contrast, neutralizing antibody responses developed faster and higher in pigs infected with GFP/ΔES4 marker virus. SN antibodies were detected from one of the six pigs by 14 days post-infection, and SN titers were detected from all of the pigs in this group, which reached an average GMT of 9.2 by 35 days post-infection. After challenge with SD03-15, an increased effect was observed, with the GMT of 18.4 from the GFP/ΔES4 marker virus infected group compared to the GMT of 5.7 from the parental virus infected group at 49 dpi (one week after challenge). Both groups reached similar SN titers at 62 dpi (three weeks after challenge) (FIG. 14C). These data suggest that on the initial infection, pigs infected with GFP/ΔES4 marker virus generated higher neutralizing antibody titers than pigs infected with parental virus.

Virus isolation and sequencing. Serum samples from 7, 14, 21, and 28 dpi were used for virus isolation as described previously (Wasilk et al., 2004). The presence of virus was confirmed by IFA with PRRSV specific antibody, SDOW17 (Nelson et al., 1993). To determine the stability of the GFP insertion and ES4 epitope deletion, viral RNA was extracted from the serum-isolated virus using QIAamp Viral RNA mini kit (Qiagen) following the manufacture's instruction. The RT-PCR was performed using previously described methods (Fang et al., 2004). The RT-PCR amplified fragment was gel purified, and the sequence was determined at the Iowa State University sequencing facility (Ames, Iowa). Primer pair nsp2-2144F/nsp2-2694R (Table 5) was used for RT-PCR and sequencing, and amplifies the nucleotide region (2144 to 2694 of SD01-08 genome) containing the GFP insertion and ES4 deletion. The full length sequence of the GFP/ΔES4 marker virus is provided in SEQ ID NO. 43 (Table 7).

Figure 11:
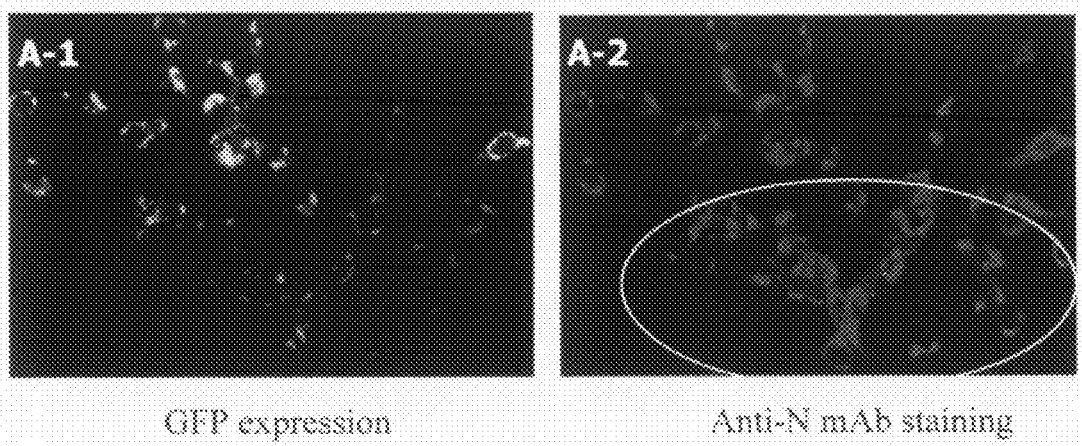
FIG. 11 depicts the stability of GFP expression.
Figure 12:
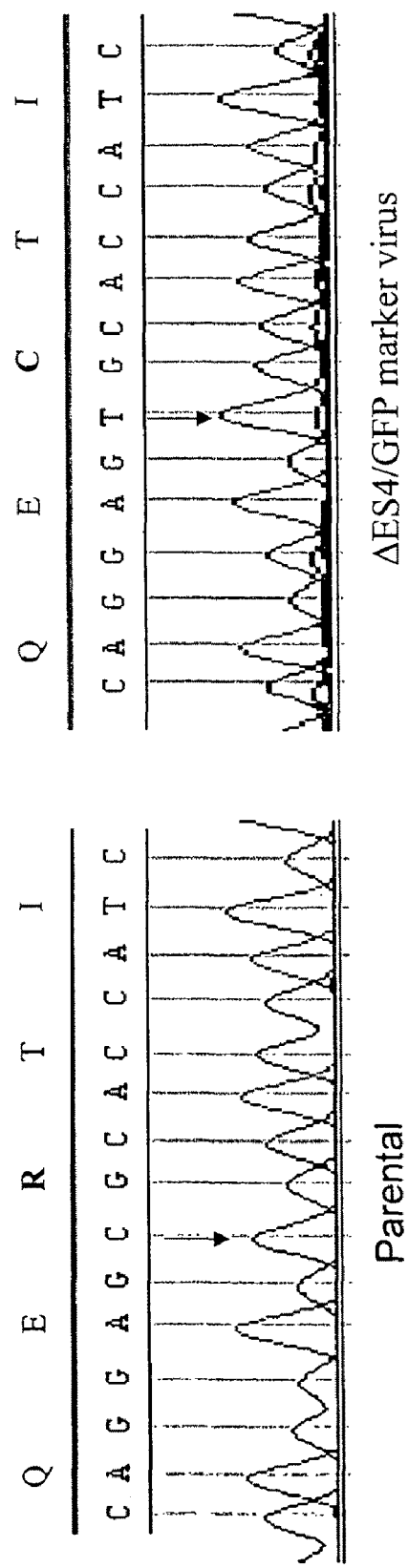
FIG. 12 depicts a comparison of the wild-type GFP gene (SEQ ID NOS: 44-45) to an Arg-97 mutated GFP gene (SEQ ID NOS: 46-47).

In vivo stability of the GFP/ΔES4 marker. To determine stability of the GFP/ΔES4 markers, serum samples from 7 to 28 dpi were used for virus isolation on MARC-145 cells. Viruses were recovered from the serum samples collected on 7, 14, and 21 dpi, and no virus was isolated from the serum samples collected from 28 dpi. In cell culture, we only observed a small population of infected cells showing weak GFP fluorescence with the viruses isolated from 7 and 14 dpi, no GFP fluoresence was observed in infected cells with the viruses isolated from 21 dpi. However, immunofluoresent staining using nucleocapsid protein specific monoclonal antibody, SDOW17 confirmed the presence of a large population of viruses, similar to that observed in the in vitro study (FIG. 11). The stability of the GFP insertion/ΔES4 deletion was determined by sequencing the corresponding regions. The results confirmed the presence of the ES4 deletion, and the GFP remained intact as a full-length gene. However, sequencing results revealed two point mutations that were located at nucleotide 144 (C to T) and nucleotide 289 (C to T) of the GFP. The nucleotide 144 mutation was silent, but the nucleotide 289 mutation caused amino acid mutation of arginine (R) to cysteine (C) at position 97 of the GFP, which is consistent with our in vitro sequencing analysis (FIG. 12). Interestingly, there was still a small population of the non-mutated GFP gene detected in the viruses isolated from 7 and 14 dpi. For each dpi, we have sequenced viruses isolated from three pigs, and sequencing was performed using both forward and reverse primers, resulting in a total of six sequences for each dpi. For the viruses isolated from 7 dpi, 1/6 sequences was found to have no mutation at position 97, and the other five sequences were determined to contain the R to C mutation. For the viruses isolated from 14 dpi, 2/6 sequences identified no mutations, and these two sequences were from two different pigs. The other four sequences were also identified to contain the R to C mutation. All the sequences generated from viruses of 21 dpi contained the R to C mutation. This data was consistent with a previous report (Kim et al., 2007) that the loss of GFP fluorescence is due to the R to C mutation. The presence of small population of the non-mutated GFP would account for the weakly fluorescing cells observed in the cell culture. These results suggest that the selection may have gradually occurred to generate the mutation in favor of improved viral replication.

GFP and ES4 epitope-based ELISA. ELISAs were performed using Immulon II HB 96-well microtiter plates (Thermo Labsystems, Franklin, Mass.). The recombinant protein was diluted in coating buffer (15 mM sodium carbonate-35 mM sodium bicarbonate, pH 9.6), and the plates were coated with 100 ul of the diluted antigen in columns 1, 3, 5, 7, 9, and 11. Columns 2, 4, 6, 8, 10, and 12 were treated with 100 ul of coating buffer as a background control. Plates were incubated at 37° C. for 1 hour, and then excess protein binding sites were blocked with 10% milk in PBST buffer (1×PBS with 0.05% Tween 20) at 4° C. overnight. The test sera were applied at 1:5 dilutions in PBST buffer with 5% milk. After 1 hour incubation at 37° C., plates were washed with PBST and horseradish peroxidase-conjugated goat anti-swine IgG (Kirkegaard & Perry Laboratories, Gaithersburg, Md.) was added to bind to any PRRSV serum antibodies that bound to the antigen on the plates. Plates were incubated at 37° C. for another hour, washed, and the peroxidase substrate ABTS (Kirkegaard & Perry Laboratories, Gaithersburg, Md.) was added for color development. The color development was quantified by reading at 405 nm with an EL800 microplate reader (BioTek Instruments Inc., Winooski, Vt.) controlled by XChek Software (IDEXX Laboratories).

A companion differential diagnostic assay was developed to differentiate animals that were vaccinated with the marker vaccine from those naturally infected with the field viruses. Because two markers, the GFP insertion (positive marker) and ES4 deletion (negative marker), were used, we developed both GFP and ES4 epitope-based ELISA assays for marker detection. Both GFP and ES4 epitopes were expressed as soluble recombinant proteins. We evaluated these two ELISA tests for detecting the specific antibodies. FIG. 15A shows results from the ES4 epitope-based ELISA, and FIG. 15B shows results from the GFP antigen-based ELISA. Pigs were challenged at day 42 post-infection shown as a dotted vertical line in FIG. 15A. As expected, the infection of Group 1 pigs with GFP/ΔES4 marker virus did not induce a detectable antibody response against the deleted ES4 epitope (FIG. 15A), but induced a strong antibody response against the GFP antigen, starting from 14 dpi and continuing for the duration of the study to 62 dpi (FIG. 15B). In contrast, the Group 2 pigs that were infected with parental virus, antibody specific to ES4 recombinant protein could be detected at 21 dpi, and also lasted to 62 dpi (FIG. 15A), while no specific antibody response was detected against GFP antigen (FIG. 15B). After challenged with 03-15, the Group 1 pigs showed a detectable antibody response to the ES4 epitope one week after challenge, since 03-15 virus contains the ES4 epitope (FIG. 15A). No specific antibody response was detected on both GFP and ES4 epitope-based ELISAs for the serum samples from the three strict negative control pigs (FIGS. 15A and 15B).

Serum samples from other Type 1 and Type 2 PRRSV infected animals. A basic requirement for the negative marker is that the antigenic region should be able to react with a broad array of field viruses. To ensure that the ES4 epitope can be reactive in various viral strains, we used serum samples from pigs infected with each of four representative strains of the US Type 1 virus, SD01-07, SD01-08, SD02-11, and SD03-15 (Lawson et al., Proc. Conf. Res. Work. Anim. Dis., abstr. 99, 2005). The SD01-07 and SD01-08 isolates were obtained from herds showing no clinical disease and SD02-11 and SD03-15 were from herds with substantial morbidity and mortality in young pigs. These four isolates also group into different branches of the phylogenetic tree developed for Type 1 PRRSV isolates of US origin (Fang et al., 2007). Serum samples from experimental pigs infected with Type 2 virus, VR2332 were obtained from the shared reagent resource of the PRRSV Cooperative Agriculture Project (CAP). As shown in FIG. 15C, the ES4 epitope reacted with anti-sera from all of the pigs infected with these four viral strains. The results are presented as mean values (n=6). The antibody response was detected by 14 dpi, and lasted more than 62 dpi. However, further testing of serum samples from a group of experimental pigs infected with Type 2 prototypic strain, VR2332 showed no reactivity with the ES4 epitope on the ELISA (data not shown). Therefore, another serological test will be required to differentiate animals infected with Type 1 viruses from those animals infected with Type 2 viruses.

III. Discussion

Two genetic markers in the nsp2 region of the PRRS virus have been constructed. The positive marker (GFP insertion) will allow detection of the animals that have been vaccinated, while the negative marker (ES4 epitope deletion) will allow detecting the presence of wild-type virus in the animals. In comparison to the MLV prepared by traditional multiple cell culture passage techniques, vaccines constructed using this type of precisely defined attenuating deletions/insertions and the use of reverse genetics technology reduces the potential risk of reversion to virulent wild-type viruses.

Marker vaccines are only useful if suitable tests (companion diagnostic tests) are available to monitor the vaccination levels and to follow the spatial course of the infection. The GFP antigen-based ELISA detected a high level of the anti-GFP response in the group of pigs infected with the marker virus. The ES4 epitope-based ELISA also detected a high level of antibody response in the group of pigs infected with the parental virus, but appeared to develop slower than that of the anti-GFP response. A high level, robust anti-GFP response can be detected by 14 dpi in marker virus infected pigs, while anti-ES4 antibody response was detected by 21 dpi and reached higher levels by 28 dpi in pigs infected with wild-type virus. The ES4 epitope possesses the highest hydrophilic values (Hopp & Woods, 1981) among the six B-cell epitopes identified on the nsp2 of Type 1 virus (Oleksiewicz et al., 2001). Analysis of the currently available nsp2 amino acid sequences of Type 1 PRRSV (Meulenberg et al., 1993; Fang et al., 2007) showed that this region possesses 63.6% to 100% amino acid sequence identity within the Type 1 genotype. Protein sequence analysis showed that the ES4 epitope region, AA736-AA790, actually contains seven small B-cell epitopes (PepTool, BioTools, Inc., Edmonton, Alberta, Canada). Epitope AA745-AA754 and AA768 AA780 are well conserved within the Type 1 genotype. Our ES4 ELISA data was consistent with the protein sequence analysis, showing that the ES4 epitope can react with sera samples from animals infected with four representative field strains of Type 1 PRRSV. However, ES4 epitope does not react with serum samples from animals infected with Type 2 isolates. In comparison of the identified B-cell epitopes on nsp2 region (Oleksiewicz et al., 2001; de Lima et al., 2006), none of the epitopes identified in the nsp2 region was conserved between Type 1 and Type 2 isolates. Therefore, another diagnostic assay is required to differentiate pigs vaccinated with the ES4 epitope deletion mutant from those pigs infected with Type 2 field strains.

The ES4 epitope in the nsp2 region appears to be non-essential for PRRSV replication but may play an important role in viral attenuation and pathogenesis in vivo. Insertion of the GFP alone did not substantially reduce the in vitro growth properties of the virus, however, when the ES4 epitope downstream of the GFP was deleted, viral titer was reduced at least two-logs in comparison to that of parental viruses. Plaque morphology also demonstrated negative effects of the markers in virus growth. In vivo characterization further demonstrated that the GFP/ΔES4 marker virus was attenuated with a lower level of viremia and higher level of neutralizing antibody response than that of wild-type virus. Protein sequence analysis has showed that the ES4 epitope region contains the highest hydrophilic value on the nsp2 (Hopp & Woods, 1981).

Surprisingly, the ES4 epitope deletion improved the stability of the GFP insertion in the nsp2. Another interesting observation is the loss of GFP fluorescence in vitro and in vivo although the GFP gene remained intact. Sequence analysis identified the Arg-97 to Cys mutation in the GFP. The Arg-97 to Cys mutation is exactly the same amino acid mutation identified on GFP that was inserted into the nsp2 region of a Type 2 virus (Kim et al., 2007). As indicated by Kim et al (2007) that Arg-97 plays a key role in the chromophore formation of GFP, which suggests that the chromophore formation may affect nsp2 function. In addition, since Cys is the amino acid normally involved in forming the disulfide-bond in the protein, the additional disulfide-bond may be required in maintaining the correct conformation of nsp2 in order to function. Nevertheless, the GFP retains its immunogenicity in vivo, and functions as an excellent positive marker for differentiation between vaccinated and wild-type virus infected animals.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various embodiments and techniques. However, it should be understood that many variations and modifications may be made while remaining within the spirit and scope of the invention.

TABLE 7

| Full length sequence of the GFP/-ES4 marker virus (SEQ ID NO: 43). | | | | | |
|---|---|---|---|---|---|
| atgatgtgta | gggtatcccc | cctacataca | caacactttt | tgtgtttgtg | tactttggag | 60 |
| gcgtgggtac | agccccgccc | cacccccttgg | cccctgttct | agcccaacag | gtatccttct | 120 |
| ccctcggggc | gagtgcgccg | cctgctgctc | ccttgcagtg | ggaaggacct | cccgagtatt | 180 |
| tccggagagc | acctgcttta | cgggatctcc | acccttttaac | catgtctggg | acgttctccc | 240 |
| ggtgcatgtg | cacccccggct | gcccgggtat | tttggaacgc | cggccaagtc | ttttgcacac | 300 |
| ggtgtctcag | tgcgcggcct | cttctctctc | cggaacttca | ggacactgac | ctcggtgtag | 360 |
| ttggattgtt | ttacaagcct | aaggacaaga | ttcactggaa | agttcctatc | ggcattcctc | 420 |
| aggtggagtg | tactccatcc | gggtgctgct | ggctctcagc | cgtattccct | ttggcgcgca | 480 |

TABLE 7-continued

Full length sequence of the GFP/-ES4 marker virus (SEQ ID NO: 43).

| | |
|---|---|
| tgacttccgg taatcacaac ttcctccaac gacttgttaa ggttgctgat gttttgtatc | 540 |
| gcgatggttg cttggcgcct cgacacctcc gtgaactcca agtttacgag cgcggttgta | 600 |
| gctggtaccc aattacgggg cccgtacccg gaatgggttt gtttgcgaac tccatgcacg | 660 |
| tgtctgacca gccgttccct ggtgccaccc atgtgttgac taactcgcct ctgcctcagc | 720 |
| gggcgtgccg gcagccgttc tgtccatttg aggaagctca ttctgacgtt tacaggtgga | 780 |
| agaaatttgt gattttttacg gactcctctc ccaacggtcg atttcgcatg atgtggacgc | 840 |
| cggaatccga tgactcagcc gccctggagg tgctgccgcc cgagttagaa cgtcaggtcg | 900 |
| agatcctcac tcggagtttt cccgctcatc accctatcaa cctagctgac tgggagctca | 960 |
| ctgagtcccc tgagaacggt ttttctttcg gcacgtccca ttcttgcggc cacatcgtcc | 1020 |
| agaaccccaa cgtgtttgac ggcaagtgct ggctcacctg cttttttgggc caatcggctg | 1080 |
| aagtgtgcta ccacgaggaa catctagcta acgccctcgg ttaccaaacc aagtggggcg | 1140 |
| tgcatggtaa gtacctccaa cgcaggcttc aagtccgcgg catgcgtgct gtggtcgatc | 1200 |
| ctgacggccc tattcacgtt gaagcgctgt cttgctccca gtcttgggtc aggcacctga | 1260 |
| ctctgaataa tgatgtcacc ccaggattcg ttcgcctgac atccatccgc attgtgtcca | 1320 |
| acacagaacc caccgctttc cggatctttc ggtttggagc acataagtgg tatggcgctg | 1380 |
| ccggcaaacg ggctcgtgcc aaacgtgcca ccaaaagtgg gaaggattcg gccctcgctc | 1440 |
| ccaagattgc cccaccggtc cccacctgtg gaatcaccac ctactctcca ccgacagacg | 1500 |
| ggtcttgtgg ttggcacgtt cttgccgcca tagtgaatcg gatgataaac ggtgacttta | 1560 |
| cgtcccccct gcctcagtac aacagaccag aggatgattg ggcttctgat tatgatcttg | 1620 |
| ctcaggcgat tcaatgttta caactgcctg ccaccgtggt tcggaatcgc gcctgtccta | 1680 |
| acgccaagta cctcataaag ctaaacgggg ttcactggga agtagaggtg agatctggaa | 1740 |
| tggctcctcg ttcccttttct cgtgaatgtg tagttggcgt ttgctctgaa ggctgtgtcg | 1800 |
| caccgcctta tccagcggac gggcttccta aacgtgcact cgaggccttg gcgtctgcct | 1860 |
| acagactacc ctcagattgt gttagctctg gtattgctga cttttcttgct gatccacctc | 1920 |
| ctcaggaatt ctggactctc gacaaaaatgt tgacctcccc gtcaccggag cggtccggct | 1980 |
| tctccagctt gtataaatta ctcttagagg ttgttccgca aaaatgtggt gctacggaag | 2040 |
| gggctttcgt ctatgctgtt gagaggatgt taaaggactg tccgagcccc gaacaggcca | 2100 |
| tggcccttct ggcaaaaatt aaagttccat cctcaaaggc cccgtctgtg tccttggacg | 2160 |
| agtgttttcc tgcgggtgtt ccagccgact tcgagccagc atttcaggaa aggccccaaa | 2220 |
| gtcccggtgc tgctgtcgcc ctgtgttcac cggacgcaaa agggttcgag ggaacagcct | 2280 |
| cggaagaagc tcaagagagt ggccataagg ccgtccacgc tgtaccccctt gccgaaggtc | 2340 |
| ccaataatga acaggtacag gtggttgctg gtgagcagct agagctcggc ggttgtggtt | 2400 |
| tggcaatcgg gagtgctcag atggtgagca agggcgagga gctgttcacc ggggtggtgc | 2460 |
| ccatcctggt cgagctggac ggcgacgtaa acggccacaa gttcagcgtg tccggcgagg | 2520 |
| gcgagggcga tgccacctac ggcaagctga ccctgaagtt catctgcacc accggcaagc | 2580 |
| tgcccgtgcc ctggcccacc ctcgtgacca ccctgaccta cggcgtgcag tgcttcagcc | 2640 |
| gctaccccga ccacatgaag cagcacgact tcttcaagtc cgccatgccc gaaggctacg | 2700 |
| tccaggagcg caccatcttc ttcaaggacg acggcaacta caagacccgc gccgaggtga | 2760 |
| agttcgaggg cgacaccctg gtgaaccgca tcgagctgaa gggcatcgac ttcaaggagg | 2820 |

TABLE 7-continued

Full length sequence of the GFP/-ES4 marker virus (SEQ ID NO: 43).

| | | | | |
|---|---|---|---|---|
| acggcaacat | cctggggcac | aagctggagt | acaactacaa cagccacaac gtctatatca | 2880 |
| tggccgacaa | gcagaagaac | ggcatcaagg | tgaacttcaa gatccgccac aacatcgagg | 2940 |
| acggcagcgt | gcagctcgcc | gaccactacc | agcagaacac ccccatcggc gacggccccg | 3000 |
| tgctgctgcc | cgacaaccac | tacctgagca | cccagtccgc cctgagcaaa gaccccaacg | 3060 |
| agaagcgcga | tcacatggtc | ctgctggagt | tcgtgaccgc cgccgggatc actctcggca | 3120 |
| tggacgagct | gtacaagtcc | tctacagggc | ccatactccg tcatgttgag cactgcggca | 3180 |
| cagagtcagg | cgacagcagt | tcgcctttgg | atctgtcttt tgcgcaaacg ttggaccagc | 3240 |
| ctttagatct | atccttggcc | gcttggccgg | tgaaggccac cgcgtctgat cctggctggg | 3300 |
| tccgcggtag | gtgcgagcct | gtcttttaa | agcctcggaa agctttctct gatggcgatt | 3360 |
| cggcccttca | gttcggggag | ctttctgagt | ccagctctgt catcgagttt gaccagacaa | 3420 |
| aagatactct | ggtggctgac | gcccctgttg | acttgacgac ttcgaacgag gccctctctg | 3480 |
| cagtcgaccc | ttccgaattt | gtcgaactca | ggcgcccgcg tcattccgca caagccttaa | 3540 |
| ttgaccgagg | cggtccactt | gctgatgtcc | atgcgaaaat aaagaaccgg gtgtatgaac | 3600 |
| agtgcctcca | agcttgtgag | cctggtagtc | gtgcaacccc agccaccagg gagtggctcg | 3660 |
| acaaaatgtg | ggatagggtg | gacatgaaaa | cttggcgctg cacttcacag ttccaggccg | 3720 |
| gtcgcattct | tgcgtccctc | aaatttcttc | ctgacatgat tcaagacacg ccgcctcctg | 3780 |
| tccccaagaa | gaaccgagct | agtgacagtg | ccggtcagac cgtccctccg cctacggata | 3840 |
| tccagcaaga | ggatgccacc | ccctccgacg | ggttatccca tgcatcggat ttttctagtc | 3900 |
| gagtgagcac | gagctggagt | tggaaaggcc | ttatgctttc cggcacccgt ctcgcggggt | 3960 |
| ctgctggtca | gcgcctcatg | acatgggttt | ttgaagttta ctcccatctc ccagctttta | 4020 |
| tactcacact | tttctcgccg | cggggctcta | tggctccagg cgattggttg tttgcaggtg | 4080 |
| ttgtttact | tgctctcttg | ctctgtcgtt | cttacccaat actcggatgc cttcccttac | 4140 |
| tgggtgtctt | ctctggttct | ttgcggcgtg | ttcgtctggg tgttttggt tcttggatgg | 4200 |
| cttttgctgt | atttttattc | tcgactccat | ccaacccagt cggttcttct tgtgaccacg | 4260 |
| attcgccgga | atgtcatgct | gagcttttgg | ctcttgagca gcgccaactt tgggaacctg | 4320 |
| tgcgcggcct | tgtggttggc | ccctcaggtc | tcttatgtgt catccttggc aagttactcg | 4380 |
| gtgggtcacg | tcatctctgg | catgttatcc | tacgtttatg catgcttaca gatttggccc | 4440 |
| tttctcttgt | ttatgtggtg | tcccaagggc | gttgtcacaa gtgttgggga aagtgtataa | 4500 |
| ggacagctcc | tgctgaggtg | gctctcaatg | tatttccttt ctcgcgcgcc actcgcaact | 4560 |
| ctctcacatc | cttgtgtgat | cggttccaaa | ctcctaaagg agttgatccc gtgcacttgg | 4620 |
| caacgggttg | gcgcgggtgt | tggcgtggtg | agagtcccat ccatcaacca caccaaaagc | 4680 |
| ccatagctta | tgccaatttg | gatgaaaaga | aaatatctgc tcaaacggtg gttgctgtcc | 4740 |
| catacgaccc | cagtcaggct | atcaaatgtc | tgaaggttct gcaggcggga ggggctatcg | 4800 |
| tggaccagcc | tacgcctgaa | gttgttcgtg | tgtctgaaat cccctttca gccccatttt | 4860 |
| tcccaaaagt | tccagtcaac | ccagattgca | ggattgtggt ggattcagat acttttgtgg | 4920 |
| ctgcagtccc | ctgcggttac | tcgacagcac | aactggtcct aggccgggc aactttgcca | 4980 |
| agttgaatca | gaccccccctt | agggactctg | cctccaccaa aacgactggt ggggcctctt | 5040 |
| atactcttgc | tgtggctcaa | gtgtctgtgt | ggactcttgt tcatttcatc ctcggtcttt | 5100 |
| ggttcacatc | acctcaagtg | tgtggccgag | gaaccgctga cccatggtgt tcaaatccct | 5160 |

TABLE 7-continued

Full length sequence of the GFP/-ES4 marker virus (SEQ ID NO: 43).

```
tttcgtatcc tgcctacggc cctggagttg tgtgctcctc tcgactttgt gtgtctgccg    5220
atggggtcac cctgccattg ttctcagctg tggcacaact ctccggtaga gaggtaggga    5280
tttttatttt agtgcttgtt tccttgactg ccttggccca tcgcctggct cttaaggcag    5340
acatgttagt ggtcttttca gcttttgtg cttacgcctg gcccatgagc tcctggttaa     5400
tctgcttctt tcctatactc ttaaagtggg ttacccttca cccctcact atgctttggg     5460
tgcactcatt cttggtgttt tgtatgccag cagccggcat cctctcacta gggataactg    5520
gccttctctg ggcagttggc cgctttaccc aggttgccgg aattattaca ccttatgaca    5580
tccaccagta tacctctggg ccacgcggtg cagccgctgt agccacagcc cagaaggca    5640
cttatatggc cgccgtccgg agagctgctt taactggacg aactttgatc ttcacccgt     5700
ctgcggtcgg atcccttctt gaaggtgctt tcaggactca taaaccctgc cttaacaccg    5760
tgaatgttgt gggttcttcc cttggttctg gaggggtttt taccattgat ggcagaaaga    5820
ccgtcgtcac tgctgctcat gtgttgaacg gcgacacagc tagagttacc ggcgactctt    5880
acaaccgcat gcacactttt aagaccagtg gcgattatgc ctggtcccat gctgatgact    5940
ggcagggcgt tgcccctgtg gtcaaggttg cgaaggggta tcgcggtcgt gcctactggc    6000
aaacatcaac cggtgtcgaa cccggcgtca ttggggaagg gttcgccttc tgtttcacca    6060
actgtggcga ttcggggtca cccgtcatct cagaatctgg tgatctcatc ggaatccata    6120
ccggttcaaa caaactcggt tctggtcttg tgacgacccc tgaaggggaa acctgcgcca    6180
tcaaagaaac caagctctct gaccttccca gacattttgc gggcccgagc gtccctcttg    6240
gggacattaa attgagtccg gccatcgtcc ctgatgtaac atctattccg agtgacttgg    6300
ctacgctcct agcttccgtc cctgtaatgg aaggcggcct ctcgaccgtt caacttctgt    6360
gtgtcttttt ccttctctgg cgcatgatgg gccatgcctg gcacccatt gttgccgtgg     6420
gcttcttttt gctgaatgaa attcttccag cagttttggt ccgagccgtg ttttcctttg    6480
cactctttat tcttgcatgg gccaccccct ggtccgcaca ggtgttaatg attagactcc    6540
tcacggcatc cctcaaccgc aacaagttgt ctctggcgtt ctacgcactt gggggtgtcg    6600
tcggttggc cgctgaaatc ggggcttttg ccggcaggct gcctgaattg tctcaagctc     6660
tttcgacata ctgttctta cctagggtcc ttgccatggc cagttatgtt cccatcatca     6720
tcattggtgg actccatgcc ctcggtgtga ttctgtggtt gttcaaatac cggtgcctcc    6780
acaactagct ggttggtgat gggagtttct caagcgcttt cttcctacgg tattttgcag    6840
agggtaatct tagaaaaggt gtttcacagt cttgtggcat gagtaacgag tccctgacgg    6900
ctgctctagc ttgcaagttg tcgcaggctg accttgactt tttgtccagc ttaacgaact    6960
tcaagtgctt tgtatctgct tcaaacatga aaaatgctgc cggccagtat attgaagcag    7020
cgtatgccaa ggccctgcgc caagagttgg cctccctagt tcaggttgac aaaatgaaag    7080
gaattttgtc taagcttgag gccttttgctg aaacagccac tccgtccctt gacgcaggtg    7140
acgtggttgt tctgcttggg caacatcctc acggatccat cctcgatatt aatgtgggga    7200
ctgaaaggaa aactgtgtcc gtgcaagaga cccggagctt aggtggttcc aaattcagtg    7260
tttgcactgt cgtgtccaac acacccgtgg acgccttaac tggcatccca ctccagacac    7320
caacccctct ttttgagaat ggtccgcgtc accgtggtga ggaagacgat cttagagtcg    7380
agaggatgaa gaaacactgt gtgtccctcg gcttccacaa cattaatggc aaagtttact    7440
gcaaaatttg ggacaagtcc accggtgata cctttttatac cgatgattcc cggtacaccc    7500
```

TABLE 7-continued

Full length sequence of the GFP/-ES4 marker virus (SEQ ID NO: 43).

```
aagaccttgc attccaggac aggtcagccg actacagaga cagggattat gagggtgtgc   7560
aaaccgcccc ccaacagggc tttgatccaa agtctgaaac ccctattggc actgtggtga   7620
tcggcggtat cacgtataac aggtacctga tcaaaggtaa ggaggtcttg gttcccaagc   7680
ctgacaacgt ccttgaagct gccaagctgt cccttgagca agctctcgct gggatgggcc   7740
aaacttgcga ccttacagct gccgaggtgg aaaagttgag gcgcatcatt agccagctcc   7800
aaggtttgac cactgaacag gcttttaaact gttagccgcc agcggcttga cccgctgtgg   7860
ccgcggcggc ttagttgtaa ctgaaacagc ggtaaaaatc gtaaagtacc acagcagaac   7920
tttcacccta ggccctctgg acctgaaagt cacctccgag gctgaggtaa agaaatcaac   7980
tgagcagggc cacgctgttg tggcaaactt atgttctggt gtcatcttga tgagacctca   8040
cccaccgtcc cttgttgatg ttcttctgaa acccggactt gacacaaaac ccggcattca   8100
accagggcat ggggccggga atatgggcgt agacggctct acttgggatt ttgaaaccgc   8160
acccacaaag gcagaacttg agttgtccaa acaaataatt caagcatgtg aagttaggcg   8220
cggggacgcc ccgaacctcc aactccctta caagctctat cctgttagag gggatcctga   8280
gcggcatggg ggccgcctta tcaataccag gtttggagat ctatcttaca aaacccctca   8340
agacaccaag tccgcaatcc atgcggcttg ttgcctgcac cccaacgggg ccctgtgtc    8400
tgatggtaag tcaacactag gtaccaccct tcaacatggt ttcgaactttt atgtccccac  8460
tgtgccctat agtgtcatgg agtacctcga ttcacgccct gacacccctt tcatgtgcac   8520
taaacatggt acttccaagg ctgctgcaga agacctccaa aaatacgacc tatctactca   8580
aggatttgtc ctgcccgggg tcttacgcct tgtacgcaga ttcatctttg gccatattgg   8640
taaggcaccg ccattgttcc tcccgtcaac ctatcccgct aaaaattcta tggcagggat   8700
caatggccag aggttcccaa caaaggacgt ccagagcata cctgaaattg acgaaatgtg   8760
tgcccgcgcc gtcaaggaga attggcaaac tgtgacacct tgtaccctca agaaacagta   8820
ctgttccaag cccaaaacca ggaccatcct gggcaccaac aactttattg ccctggctca   8880
ccgatcggcg ctcagtggtg tcacccaggc attcatgaag aaggcttgga agtccccgat   8940
tgccttggga aaaacaaat tcaaggagct gcattgcact gtcgccggca ggtgtcttga    9000
agccgacttg gcctcctgtg accgcagcac ccccgccatt gtgaggtggt tcgtcgccaa   9060
cctcctgtat gaacttgcag gatgtgaaga gtacttgcct agctatgtgc ttaactgctg   9120
ccatgacctt gtggcaacac aggatggtgc cttcacaaaa cgcggtggcc tgtcgtccgg   9180
ggaccccgtc accagtgtgt ctaacaccgt atattcactg ataatctatg cccagcacat   9240
ggtgttgtcg gccttaaaaa tgggtcatga atcggtctc aagttcctcg aggaacagct    9300
caaattcgag gacctcctcg aaatccagcc tatgttggtc tattctgatg accttgtctt   9360
gtacgctgaa aggcccactt ttcctaatta tcactggtgg gtcgagcacc ttgacctaat   9420
gctgggtttc agaacggacc caaagaagac agtcataact gataaaccca gcttcctcgg   9480
ctgcagaatt gaggcggggc gacagctggt ccctaatcgc gaccgcatcc tggctgctct   9540
cgcatatcac atgaaggcgc agaacgcctc agagtattat gcgtctgctg ccgcaatcct   9600
gatggattca tgtgccttgca ttgatcatga ccctgagtgg tatgaggacc tcatctgcgg   9660
tatcgcccga tgcgccgcc aggatggtta tagtttccca ggcccggcat ttttcatgtc    9720
catgtgggaa aagctgagaa gtcacaatga agggaagaaa tttcgacact gcggcatctg   9780
cgacgccaaa gccgaccatg catccgcctg tgggcttgat ttgtgttttgt tccactcaca   9840
```

TABLE 7-continued

Full length sequence of the GFP/-ES4 marker virus (SEQ ID NO: 43).

```
ctttcatcaa cactgccccg tcactctgag ctgtggtcat catgccggtt caagggaatg    9900
ttcgcagtgt cagtcacctg ttggggctgg cagatctcct cctgatgccg tgctaaaaca    9960
aatcctgtac aaacctcctc gtacagtcat catgaaggtg ggtaacaaaa caacggccct   10020
cgatccgggg aggtaccagt cccgtcgagg tcttgttgca gtcaagaggg gtattgcagg   10080
caatgaagtt gatcttcctg atggggacta ccaagtagtg cctcttttac caacttgtaa   10140
agacataaac atggtaaagg tggcttgcaa tgtactactc agtaagttca tagtggggcc   10200
accaggttcc ggaaagacca cctggttact gagtcaagtc caggacgatg atgtcattta   10260
cacacccacc catcagacca tgtttgatat agtcagtgct ctcaaagttt gcaggtattc   10320
tattccagga gcctcaggac ttcctttccc accacctgcc aggtccgggc cgtgggttag   10380
gctcgtggcc agcgggcacg tccccggccg aacatcatac ctcgatgagg ctggatattg   10440
taatcatctg acattctca gactgctttc caaaacaccc ctcgtgtgtt tgggtgacct    10500
tcaacaactt caccctgtcg gctttgactc ctactgttat gtgtttgatc agatgcctca   10560
aaagcaactg accactattt atagatttgg ccctaacatc tgcgcagcca tccagccttg   10620
ttacagggag aagcttgaat ctaaggctag gaacaccagg gtggtcttta ccacctggcc   10680
tgtggccttt ggtcaggtgc tgacaccata ccataaagat cgcatcggct ctgcgataac   10740
catagactca tcccaggggg ccactttcga cattgtgaca ttgcatctac catcaccaaa   10800
gtccctaaat aaatcccgag cacttgtagc catcactcgg gcaagacacg ggttgttcat   10860
ttatgaccct cacaaccagc tccaggagtt tttcaacctg atccctgagc gcactgattg   10920
caaccttgtg ttcagccgtg gggatgatct ggtagttctt agtgcggaca atgcagtcac   10980
aactgtagcg aaggccctag ggacaggtcc atctcgattt cgagtatcag acccgaggtg   11040
caagtctctc ttagctgctt gttcggccag tctggagggg agctgtatgc cactaccaca   11100
agtggcacat aacctggggt tttacttctc cccagacagt ccagcatttg cacctctgcc   11160
aaaggagtta gcgccacatt ggccagtggt tactcaccag aacaatcggg cgtggcccga   11220
tcgacttgtc gctagtatgc gcccaattga tgcccgctac agcaagccaa tggtcggtgc   11280
agggtatgtg gtcgggccgt ccacctttct tggtactcct ggtgtagtgt catactacct   11340
cacgctatac atcaggggtg agccccaggc cttgccagag acactcgttt caacaggacg   11400
catagccact gactgccggg agtatctcga cgcggctgag gaagaggcag caaaagaact   11460
ccccacgca ttcattggcg atgtcaaagg taccacggtc ggggggtgtc accacatcac   11520
atcaaaatac ctacccagga ccctgcctaa ggactctgtt gctgtagttg gagtaagctc   11580
gcccggcagg gctgctaaag ccatgtgcac tctcactgat gtgtatctcc ccgaactccg   11640
gccatacctg caacctgaga cggcgtcgaa atgctggaaa ctcaaattag acttcaggga   11700
cgtccgacta atggtctgga aaggagccac cgcctatttc cagttggaag gacttacatg   11760
gtcagcgctg cctgactatg ccaggtttat tcagcttccc aaggacgccg ttgtgtacat   11820
tgatccgtgt ataggaccgg caacagccaa ccgcaaggtc gtgcgaacca cagactggcg   11880
ggccgacctg gcagtgacac cgtatgatta cggtgcccag aacattttga caacagcctg   11940
gttcgaggac ctcgggccgc agtggaagat ttgggggttg cagcccttca ggcgggcatt   12000
tggctttgaa aatactgagg attgggcaat ccttgcacgc cgtatgagtg acggcaaaga   12060
ctacactgac tacaactggg attgtgttcg agaacgccca cacgccatct acgggcgtgc   12120
tcgtgaccat acatatcatt ttgcccccgg cacggaattg caggtagagc tgggtaaacc   12180
```

TABLE 7-continued

Full length sequence of the GFP/-ES4 marker virus (SEQ ID NO: 43).

```
ccggctgccg cctggacgag agccgtaaac ttggagtgat gcaatggggt cactgtggag   12240
taaaatcagc cagctgttcg tggatgcctt cactgagttt cttgtcagtg tggttgatat   12300
tgtcattttc cttgccatac tgtttgggtt caccgtcgca ggatggttat tggtcttcct   12360
tctcagagtg gtttgctccg cgcttctccg ttcgcgctct gccattcact ctcccgaact   12420
atcgaaggtc ctatgaaagc ttgttgccca actgcaggcc ggatgtccca caatttgcat   12480
ttaagcaccc attgggtata ctttggcaca tgcgagtttc ccacctgatt gatgagatgg   12540
tctctcgccg catttaccag accatggaac attcaggtca agcggcctgg aaatatgtgg   12600
tcggtgaggc cactctcacg aagctatcaa agcttgatat agttactcat ttccaacatc   12660
tggccgcagt agaggcggat tcttgccgct ttctcagctc acgactcgtg atgctaaaaa   12720
atcttgccgt tggcaatgtg agcctacagt acaacaccac gttggatcgc gttgaactca   12780
ttttccccac gccaggtacg aggcccaagt tgaccgactt cagacaatgg ctcatcagtg   12840
tgcatgcttc cattttttcc tctgtggctt catctgttac cttgttcata gtgctttggc   12900
tgcgaattcc agctctacgc tatgttttg gtttccattg gcccacggca acacatcatt   12960
cgagctgacc atcaattata ccatatgcat gccctgtctt accagtcaag cagctcgcca   13020
aaggctcgag cccggtcgta acatgtggtg cagaataggg catgataggt gtgaggagcg   13080
tgaccatgat gagttgttaa tgtccatccc gtccgggtac gacaacctca aacttgaggg   13140
atattatgct tggctggctt ttttgtcctt ttcctacgcg gcccaattcc atccggagct   13200
gttcgggata gggaatgtgt cgcgcgtctt cgtggacaag cgacaccagt ttatttgtgc   13260
cgagcatggt ggactcaatt caaccttatc taccagcac aatatctccg cattatatgc   13320
ggtattatta caccaccaaa tagacggggg taattggttc catttggaat ggctgcggcc   13380 gctttttcc tcctggttgg tgctcaacat atcatggttt ctgaggcgtt cgcctgtaag   13440
ccctgtttct cgacgcatct atcagatatt aagaccaaca cgaccgcggc tgccggtttc   13500
atggtccttc agaacatcaa ttgttcccgg cctcacgagg cctcagcaac gcaaggtcaa   13560
gttccctcca gaaagtcgtc ccaatgccgt gaagccgtcg gtgttcccca atacatcacg   13620
ataacggcca acgtgaccga cgaatcatat ttgtacaacg cggacttgct gatgctttct   13680
gcgtgccttt tctacgcctc ggaaatgagc gagaaaggct ttaaagttat ctttgggaat   13740
gtctctggcg ttgttctgc ttgtgtcaat ttcacagatt atgtggccca tgtgacccaa   13800
catacccagc agcatcatct ggtgattaat cacatccggt tactgcactt cctgacacca   13860
tctgcaatga ggtgggctac aaccattgct tgtctgttcg ccattctctt ggcgatatga   13920
aatgttctca caaattgggg cattccttga ctccgcactc ttgcttctgg tggctttttt   13980
tgctgtgtac cggcttgtcc tggtcctttg ccgatggcaa cggcaacaac tcgacatacc   14040
aatacatata taatttgacg atatgcgagt tgaatgggac caattggctg tccggccatt   14100
ttgaatgggc agttgagacc tttgtgcttt acccggttgt cactcatatc ctctcactgg   14160
gttttctcac gacaagtcat ttttttgacg cgctcggtct cggcgctgta tccactgcag   14220
gatttgtcgg agggcggtat gtacttagca gcgtctacgg cgcttgtgct ttcgcagcgt   14280
tcgtatgctt cgtcatccgt gctgctaaaa attgcatggc ctgccgctat gcccgtaccc   14340
ggttcaccaa cttcattgtg gacgaccggg ggggagttca tagatggaag tctccaatag   14400
tggtagaaaa actgggcaaa gccgaaattg gcggcaacct tgtcaccatc aaacatgtcg   14460
tcctcgaagg ggttaaagct caaccccttga cgagaacttc ggccgagcaa tgggaggcct   14520
```

TABLE 7-continued

Full length sequence of the GFP/-ES4 marker virus (SEQ ID NO: 43).

```
agataatttt tgcaacgatc ctaccgccgc acaaaagatc gtgctagcct tcagcatcac  14580
atacacacct ataatgatat acgcccttaa ggtgtcacgc ggccgactcc tggggctgtt  14640
gcacatccta atatttctga actgttcctt tacattcgga tacatgacat atgtgcattt  14700
tcattctacc caccgtgtcg cacttaccct gggggctgtt gtcgcccttt tgtggggtgt  14760
ctacagcctc acagagtcat ggaagtttat cacttccaga tgcagattgt gttgcctcgg  14820
ccggcgatac attctggccc ctgcccatca cgtagaaagt gctgcaggtc tccattcaat  14880
ctcagcgtct ggtaaccgag catacgctgt gagaaagccc ggactaacat cagtgaacgg  14940
cactctagta ccaggacttc ggagcctcgt gctgggcggc aaacgagctg ttaaacgagg  15000
agtggttaac ctcgtcaagt atggccggta aaaatcagag ccagaagaaa aagaaaagta  15060
cggctccaat ggggaatggc cagccagtca atcaactgtg ccagttgctg ggtgcaatga  15120
taaagtccca gcgccagcaa cctaggggag gacaggctaa aaagaaaaag cctgagaagc  15180
cacattttcc cctggctgca gaagatgaca tccggcacca cctcacccaa actgaacgct  15240
ccctctgctt gcaatcgatc cagacggctt tcaatcaagg cgcaggaact gcgtcgcttt  15300
catccagcgg gaaggtcagt ttccaggttg agtttatgct gccggttgct catacagtgc  15360
gcctgattcg cgtgacttct acatccgcca gtcagggtgc aaattaattt gacagtcagg  15420
tgaatggccg cgattggcgt gtggcctctg agtcacctat tcaattaggg cgatcacatg  15480
ggggtcatac ttaatcaggc aggaaccatg tgaccgaaat t                      15521
```

REFERENCES

1. Allende, R., Lewis, T. L., Lu, Z., Rock, D. L., Kutish, G. F., Ali, A., Doster, A. R. & Osorio, F. A. (1999). North American and European porcine reproductive and respiratory syndrome viruses differ in non-structural protein coding regions. *J Gen Virol* 80, 307-315.
2. Babiuk, L., Lewis, J., Suradhat, S., Baca-Estrada, M., Foldvari, M. & Babiuk, S. (1999). Polynucleotide vaccines: potential for inducing immunity in animals. *J Biotechnol* 73, 131-140.
3. Babiuk, L. A. (1999). Broadening the approaches to developing more effective vaccines. *Vaccine* 17, 1587-1595.
4. Babiuk, L. A., Babiuk, S. L. & Baca-Estrada, M. E. (2002). Novel vaccine strategies. *Adv Virus Res* 58, 29-80.
5. Barrett, T., Parida, S., Mohapatra, M., Walsh, P., Das, S. & Baron, M. D. (2003). Development of new generation rinderpest vaccines. *Dev Biol* 114, 89-97.
6. Bautista, E. M., S. M. Goyal, I. J. Soon, H. S. Joo, and J. E. Collins. 1996. Structural polypeptides of the American (VR-2332) strain of porcine reproductive and respiratory syndrome virus. Arch. Virol. 141:1357-1365.
7. Benfield, D. A., E. Nelson, J. E. Collins, L. Harris, S. M. Goyal, D. Robison, W. T. Christianson, R. B. Morrison, D. Gorcyca, and D. Chladek. 1992. Characterization of swine infertility and respiratory syndrome (SIRS) virus (isolate ATCC VR-2332). J. Vet. Diagn. Invest. 4:127-133.
8. Bosch, J. C., Kaashoek, M. J., Kroese, A. H. & Van Oirschot, J. T. (1996). An attenuated bovine herpesvirus 1 marker vaccine induces a better protection than two inactivated marker vaccines. *Vet Microbiol* 52, 223-234.
9. Calvert, J. G., M. G. Sheppard, and S. K. W. Welch. 2003. Infectious cDNA clone of North American porcine reproductive and respiratory syndrome (PRRS) virus and use thereof. US Patent Application 20030157689.
10. Calvert, J. G., M. G. Sheppard, and S. K. W. Welch. 2002. Infectious cDNA clone of North American porcine reproductive and respiratory syndrome (PRRS) virus and use thereof. U.S. Pat. No. 6,500,662.
11. Castillo-Olivares, J., Wiering a, R. T., Bakonyi, A. A. F., de Vries, N. J., Poyner, D. & Rottier, P. J. M. (2003). Generation of a candidate live marker vaccine for equine arteritis virus by deletion of the major virus neutralization domain. *J Virol* 77, 8470-8480.
12. Collins, J. E., D. A. Benfield, W. T. Christianson, L. Harris, J. C. Hennings, D. P. Shaw, S. M. Goyal, D. Gorcyca, D. Chladek, S. McCullough, R. B. Morrison, and H. S. Joo. 1992. Isolation of swine infertility and respiratory syndrome virus (Isolate ATCC VR-2332) in North America and experimental reproduction of the disease in gnotobiotic pigs. J. Vet. Diag. Invest. 4:117-126.
13. den Boon, J. A., K. S. Faaberg, J. J. M. Meulenberg, A. L. M. Wassenaar, P. G. W. Plagemann, A. E. Gorbelenya, and E. J. Snijder. 1995. Processing and evolution of the N-Terminal region of the arterivirus replicase ORF1a protein: identification of two papainlike cysteine proteases. J. Virol. 69:4500-4505.
14. de Lima, M., Pattnaik, A. K., Flores, E. F. & Osorio, F. A. (2006). Mapping of B-cell linear epitopes on Nsp2 and structural proteins of a North American strain of porcine reproductive and respiratory syndrome virus. *Virology* 353, 410-421.
15. Fang, Y., D.-Y. Kim, S. Ropp, P. Steen, J. Christopher-Hennings, E. A. Nelson, and R. R. Rowland. 2004. Heterogeneity in Nsp2 of European-like porcine reproductive and respiratory syndrome viruses isolated in the United States. Virus Res. 100:229-235.

16. Fang, Y., Rowland, R. R. R., Roof, M., Lunney, J. K., Christopher-Hennings, J. & Nelson, E. A. (2006). A full-length cDNA infectious clone of North American type 1 porcine reproductive and respiratory syndrome virus: expression of green fluorescent protein in the nsp2 region. *J Virol* 80, 11447-11455.

17. Fang, Y., Schneider, P., Zhang, W. P., Faaberg, K., Nelson, E. A. & Rowland, R. R. R. (2007). Diversity and evolution of a newly emerged North American Type 1 porcine arterivirus. *Arch Virol* 152, 1009-1017.

18. Ferrin, N. H., Fang, Y., Johnson, C. R., Murtaugh, M. P., Polson, D. D., Torremorell, M., et al. (2004). Validation of a Blocking ELISA for the detection of antibodies against porcine reproductive and respiratory syndrome virus. *Clin Diagn Lab* 1 mm 11, 503-514.

19. Fitzgerald, D. J., Bronson, E. D. & Anderson, J. N. (1996). Compositional similarities between the human immunodeficiency virus and surface antigens of pathogens. *AIDS Res Hum Retroviruses* 12, 99.

20. Floegel-Niesmann, G. (2003). Marker vaccines and companion diagnostic tests for classical swine fever. *Dev Biol* 114, 185-191.

21. Frias-Staheli, N., Glannakopoulos, N. V., Klkkert, M., Taylor, S. L., Bridgen, A., Paragas, J., Richt, J. A., Rowland, R. R. R., Schmaljohn, C. S., Lenschow, D. J., Snijder, E. J., Garcia-Sastre, A. & Virgin, H. W. (2007). Ovarian tumor domain-containing viral proteases evade ubiquitin- and ISG15-dependent innate immune responses. *Cell Host Microbe* 2, 404-416.

22. Gao, Z. Q., X. Guo, and H. C. Yang. 2004. Genomic characterization of two Chinese isolates of porcine respiratory and reproductive syndrome virus. Arch. Virol. 149:1341-1351.

23. Garrity, R. R., Rimmelzwaan, G., Minassian, A., Tsai, W. P., Lin, G., de Jong, J., Goudsmit, J. & Nara, P. (1997). Refocusing neutralizing antibody response by targeted dampening of an immunodominant epitope. *J Immunology* 159, 279-289.

24. Hall, B. F. & Joiner, K. A. (1991). Strategies of obligate intracellular parasites for evading host defenses. *Immunol Today* 12, A22.

25. Hayashi, N., Welschof, M., Zewe, M., Braunagel, M., Dübel, S., Breitling, F. & Little, M. (1994). Simultaneous mutagenesis of antibody CDR regions by overlap extension and PCR. *Biotechniques* 17, 310, 312, 314-315.

26. Halbur, P. G., P. S. Paul, M. L. Frey, J. Landgraf, K. Eernisse, X.-J. Meng, M. A. Lum, J. J. Andrews, and J. A. Rathje. 1995. Comparison of the pathogenicity of two U.S. porcine reproductive and respiratory syndrome virus isolates with that of the Lelystad virus. Vet. Pathol. 32:648-660.

27. Han, J., Liu, G., Wang, Y. & Faaberg, K. S. (2007). Identification of nonessential regions of the nsp2 replicase protein of porcine reproductive and respiratory syndrome virus strain VR-2332 for replication in cell culture. *J Virol* 81, 9878-9890.

28. Ho, S. N., H. D. Hunt, R. M. Horton, J. K. Pullen, and L. R. Pease. 1989. Site-directed mutagenesis by overlap extension using the polymerase chain reaction. Gene. 77:51-59.

29. Hopp, T. P. & Woods, K. R. (1981). Prediction of protein antigenic determinants from amino acid sequences. *Proc Natl Acad Sci* 78, 3824-3828.

30. Jespersen, T., D. Mogens, and F. S. Pedersen. 1997. Efficient non-PCR-mediated overlap extension of PCR fragments by exonuclease "end polishing." Biotechniques 23:48-52.

31. Johnson, C. R., Yu, W. & Murtaugh, M. (2007). Cross-reactive antibody responses to nsp1 and nsp2 of Porcine reproductive and respiratory syndrome virus. *J Gen Virol* 88, 1184-1195.

32. Keffaber, K. K. 1989. Reproductive failure of unknown etiology. Am. Assoc. Swine Pract. Newsl. 1:1-9.

33. Kim, D. Y., Calvert, J. G., Chang, K. O., Horlen, K., Kerrigan, M., Rowland, R. R. R. (2007). Expression and stability of foreign tags inserted into nsp2 of porcine reproductive and respiratory syndrome virus (PRRSV). *Virus Research* 128, 106-114.

34. King, N. J. & Kesson, A. M. (2003). Interaction of flaviviruses with cells of the vertebrate host and decoy of the immune response. *Immunol Cell Biol* 81, 207-216.

35. Konig, P., Beer, M., Makoschey, B., Teifke, J. P., Polster, U., Giesow, K. & Keil, G. M. (2003). Recombinant virus-expressed bovine cytokines do not improve efficacy of a bovine herpesvirus 1 marker vaccine strain. *Vaccine* 22, 202-212.

36. Mardassi, H., B. Massive, and S. Dea. 1996. Intracellular synthesis, processing, and transport of proteins encoded by ORFs 5 to 7 of porcine reproductive and respiratory syndrome virus. Virology 221:98-112.

37. Marrack, P. & Kappler, J. (1994). Subversion of the immune system by pathogens. *Cell* 76, 323.

38. Mebatsion, T., Koolen, M. J. M., de Vaan, L. T. C., de Haas, N., Braber, M., Romer-Oberdorfer, A., van den Elzen, P. & van der Marel, P. (2002). Newcastle disease virus marker vaccine: an immunodominant epitope on the nucleoprotein gene of NDV can be deleted or replaced by a foreign epitope. *J Virol* 76, 10138-10146.

39. Meng, X. J., P. S. Paul, I. Morozov, and P. G. Halbur. 1996. A nested set of six or seven subgenomic mRNAs is formed in cells infected with different isolates of porcine reproductive and respiratory syndrome virus. J. Gen. Virol. 77:1265-1270.

40. Meulenberg, J. J., J. N. Bos-de Ruijter, R. Van de Graaf, G. Wensvoort, and M. Moormann. 1998. Infectious transcripts from cloned genomic-length cDNA of porcine reproductive and respiratory syndrome virus. J. Virol. 72:380-387.

41. Meulenberg, J. J., and A. Petersen-den Besten. 1996. Identification and characterization of a sixth structural protein of Lelystad virus: the glycoprotein GP2 encoded by ORF2 is incorporated in virus particles. Virology 225:44-51.

42. Meulenberg, J. J. M., A. Petersen-den Besten, E. P. de Kluyver, R. J. M. Moormann, W. M. M. Schaaper, and G. Wensvoort. 1995. Characterization of proteins encoded by ORFs 2 to 7 of Lelystad virus. Virology 206:155-163.

43. Meulenberg, J. J., M. M. Hulst, E. J. de Meijer, P. L. Moonen, A. den Besten, E. P. de Kluyver, G. Wensvoort, and R. J. Moormann. 1993. Lelystad virus, the causative agent of porcine epidemic abortion and respiratory syndrome (PEARS), is related to LDV and EAV. Virology 192:62-72.

44. Moradpour, D., M. J. Evans, R. Gosert, Z. Yuan, H. E. Blum, S. P. Goff, B. D. Lindenbach, and C. M. Rice. 2004. Insertion of green fluorescent protein into nonstructural protein 5A allows direct visualization of functional hepatitis C virus replication complexes. J. Virol. 78:7400-7409.

45. Mounir, S., H. Mardassi, and S. Dea. 1995. Identification and characterization of the porcine reproductive respiratory virus ORFs 7, 5 and 4 products. Adv. Exp. Med. Biol. 80:317-320.

46. Nara, P. L., Smit, L., Dunlop, N., Natch, W., Merges, M., Waters, D., Kelliher, J., Gallo, R. C., Fischinger, P. J. &

Goudsmit, J. (1990). Emergence of viruses resistant to neutralization by V3-specific antibodies in experimental human immunodeficiency virus type 1 IIIB infection of chimpanzees. *J Virol* 64, 3779-3791.

47. Nelson, E. A., J. Christopher-Hennings, T. Drew, G. Wensvoort, J. Collins, and D. A. Benfield. 1993. Differentiation of U.S. and European isolates of porcine reproductive and respiratory syndrome virus by monoclonal antibodies. J. Clin. Microbiol. 31:3184-3189.

48. Nelson, E. A., J. Christopher-Hennings, and D. A. Benfield. 1995. Structural proteins of porcine reproductive and respiratory syndrome virus (PRRSV). Adv. Exp. Med. Biol. 380:321-323.

49. Nelsen, C. J., Murtaugh, M. P. & Faaberg, K. S. (1999). Porcine reproductive and respiratory syndrome virus comparison: divergent evolution on two continents. *J Virol* 73, 270-280.

50. Neumann, E. 2005. Assessment of the economic impact of porcine reproductive and respiratory syndrome on swine production in the United States. JAVMA, 227:385-392.

51. Nielsen, H. S., G.-P. Liu, J. Nielsen, M. B. Oleksiewicz, A. Botner, T. Storgaard, and K. S. Faaberg. 2003. Generation of an infectious clone of VR-2332, a highly virulent North American-type isolate of porcine reproductive and respiratory syndrome virus. J. Virol. 77:3702-3711.

52. Oleksiewicz, M. B., A. Botner, P. Toft, P. Normann, and T. Storgaard. 2001. Epitope mapping porcine reproductive and respiratory syndrome virus by phage display: the nsp2 fragment of the replicase polyprotein contains a cluster of B-cell epitopes. J. Virol. 75:3277-3290.

53. Ropp, S. L., C. E. Mahlum Wees, Y. Fang, E. A. Nelson, K. D. Rossow, K. Bien, B. Arndt, S. Preszler, P. Steen, J. Christopher-Hennings, J. E. Collins, D. A. Benfield, and K. S. Faaberg. 2004. Characterization of emerging European-like PRRSV isolates in the United States. J. Virol. 78:3684-3703.

54. Shen, S., J. Kwang, W. Liu, and D. X. Lui. 2000. Determination of the complete nucleotide sequence of a vaccine strain of porcine reproductive and respiratory syndrome virus and identification of the nsp2 gene with a unique insertion. Arch. Virol. 145:871-883.

55. Snijder, E. J., and J. J. Meulenberg. 1998. The molecular biology of arteriviruses. J. Gen. Virol. 79:961-979.

56. Snijder, E. J., A. L. M. Wassenaar, and W. J. M. Spaan. 1994. Proteolytic processing of the replicase ORF1a protein of equine arteritis virus. J. Virol. 68:5755-5764.

57. Snijder, E. J., Wassenaar, A. L. M., Spaan, W. J. & Gorbalenya, A. E. (1995). The arterivirus Nsp2 protease. An unusual cysteine protease with primary structure similarities to both papain-like and chymotrypsin-like proteases. *J Biol Chem* 270, 16671-16676.

58. Sun, T., Lu, P. & Wang, X. (2004). Localization of infection-related epitopes on the non-structural protein 3ABC of foot-and-mouth disease virus and the application of tandem epitopes. *J Virol Methods* 119, 79-86.

59. Tian, K., Yu, X., Zhao, T., Feng, Y., Cao, Z., Wang, C., et al. (2007). Emergence of fatal PRRSV variants: unparalleled outbreaks of atypical PRRS in China and molecular dissection of the unique hallmark. *PLoS ONE* 2, 526.

60. Truong H. M., Z. Lu, G. Kutish, J. Galeota, F. A. Osorio, and A. K. Pattnaik. 2004. A highly pathogenic porcine reproductive and respiratory syndrome virus generated from an infectious cDNA clone retains the in vivo markers of virulence and transmissibility characteristics of the parental strain. Virology. 325:308-319.

61. van Dinten, L. C., A. L. Wassenaar, A. E. Gorbalenya, W. J. Spaan, and E. J. Snijder. 1996. Processing of the equine arteritis virus replicase ORF1b protein: identification of cleavage products containing the putative viral polymerase and helicase domains. J. Virol. 70:6625-6633.

62. van Gennip, H. G., Bouma, A., van Rijn, P. A., Widjojoatmodjo M. N. & Moormann, R. J. (2002). Experimental non-transmissible marker vaccines for classical swine fever (CSF) by trans-complementation of E(rns) or E2 of CSFV. *Vaccine* 20, 1544-1556.

63. van Oirschot, J. T. (2001). Present a future of veterinary viral vaccinology: a review. *Vet. Quart* 23, 100-108.

64. van Oirschot, J. T., Kaashoek, M. J., Rijsewijk, F. A. & Stegeman, J. A. (1996). The use of marker vaccines in eradication of herpesviruses. *J Biotechnol* 44, 75-81.

65. Vijayakrishanan, L., Kumar, V., Agrewala, J. N., Mishra, G. C. & Rao, K. V. (1994). Antigen-specific early primary humoral responses modulate immunodominance of B cell epitopes. *J Immunol*. 153, 1613-1625.

66. Walsh, E. P., Baron, M. D., Rennie, L., Anderson, J. & Barrett, T. (2000). Development of a genetically marked recombinant rinderpest vaccine expressing green fluorescent protein. *J Gen Virol* 81, 709-718.

67. Wasilk, A., J. Callahan, J. Christopher-Hennings, B. T. Gay, Y. Fang, M. Dammen, M. Torremorell, D. Polson, M. Mellencamp, E. A. Nelson and W. Nelson. 2004. Detection of U.S. and Lelystad/European-like porcine reproductive and respiratory syndrome virus and relative quantitation in boar semen and serum by real-time PCR. J. Clin. Micro. 42:4453-4461.

68. Wassenaar, A. L., W. J. Spaan, A. E. Gorbalenya, and E. J. Snijder. 1997. Alternative proteolytic processing of the arterivirus replicase ORF1a polyprotein: evidence that Nsp2 acts as a cofactor for the Nsp4 serine protease. J. Virol. 71:9313-9322.

69. Wensvoort, G., C. Terpstra, J. M. Pol., E. A. ter Laak, M. Bloemrad, E. P. deKluyer, C. Kragten, L. van Buiten, A. den Besten, F. Wagenaar, J. M. Broekhuijsen, P. L. J. M. Moonen, T. Zetstra, E. A. de Boer, H. J. Tibben, M. F. de Jong, P. van't Veld, G. J. R. Groenland, J. A. van Gennep, M. T. H. Voets, J. H. M. Verheijden, and J. Braamskamp. 1991. Mystery swine disease in the Netherlands: the isolation of Lelystad virus. Vet. Quarterly 13:121-130.

70. Widjojoatmodjo, M. N., van Gennip, H. G., Bouma, A., van Rijn, P. A., Moormann, R. J. (2000). Classical swine fever virus E(rns) deletion mutants: trans-complementation and potential use as non transmissible, modified, live-attenuated marker vaccines. *J Virol* 74, 2973-2980.

71. Wu, W. H., Fang, Y., Rowland, R. R. R., Lawson, S. R., Christopher-Hennings, J., Yoon, K. J. & Nelson, E. A. (2005). The 2b protein as a minor structural component of PRRSV. *Virus Res* 114, 177-181.

72. Wu, W. H., Y. Fang, R. Farwell, M. Steffen-Bien, R. R. Rowland, J. Christopher-Hennings, and E. A. Nelson. 2001. A 10-kDa structural protein of porcine reproductive and respiratory syndrome virus encoded by ORF 2b. Virology 287:183-191.

73. Zeman, D., R. Neiger, M. Yaeger, E. Nelson, D. Benfield, P. Leslie-Steen, J. Thomson, D. Miskimins, R. Daly, and M. Minehart. 1993. Laboratory investigation of PRRS virus infection in three swine herds. J. Vet. Diagn. Invest. 5:522-528.

74. Y. Fang, B. Neiger, T. Hawkins, J. Christopher-Hennings, R. Rowland, E. Nelson, Proc. Conf. Res. Work. Anim. Dis., abstr. 78, 2004

What is claimed is:

1. A method comprising differentiating a subject previously vaccinated against North American Type 1 PRRSV with a marker vaccine from a subject previously naturally infected with PRRSV, the method comprising:
   collecting a sample from a subject,
   determining a presence of amino acids 736-790 of ORF1a in non-structural protein 2 of North American Type 1 PRRSV in the sample via immunological assay; and
   determining a presence of a GFP marker inserted between amino acids 733 and 734 of ORF1a in non-structural protein 2 of North American Type 1 PRRSV in the sample via immunological assay, wherein the presence of the GFP marker in the sample and an absence of the amino acids 736-790 of ORF1a in non-structural protein 2 of a North American Type 1 PRRSV in the sample is indicative of a subject previously vaccinated against North American Type 1 PRRSV.

2. The method of claim 1, wherein the presence of a amino acids 736-790 of ORF1a in non-structural protein 2 of a North American Type 1 PRRSV is determined by incubating the sample with an antibody against the wild-type epitope of a North American Type 1 PRRSV.

3. The method of claim 1 wherein the marker vaccine comprises SEQ ID NO: 43.

* * * * *

SEQUENCE LISTING

<160> NUMBER OF SEQ ID NOS: 48

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
gcatggctct taaggcagac                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
cagcttcaag gcagttgtca                                               20

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
tgttgtgatc ggcggtatta                                               20

<210> SEQ ID NO 4
<211> LENGTH: 27
<212> TYPE: DNA
<213> ORGANISM: Artificial Sequence
<220> FEATURE:
<223> OTHER INFORMATION: Synthetic primer

<400> SEQUENCE: 4
cggcgcgggc acacatttcg tcaattt                                       27

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
tacgacctat ccacccaagg                                               20

<210> SEQ ID NO 6
<211> LENGTH: 22
<212> TYPE: DNA
<213> ORGANISM: Artificial Sequence
<220> FEATURE:
<223> OTHER INFORMATION: Synthetic primer

<400> SEQUENCE: 6
gaatctatgg ttatcgcaga gc                                            22

<210> SEQ ID NO 7
<211> LENGTH: 20
<212> TYPE: DNA

```
<213> ORGANISM: Artificial Sequence
<220> FEATURE:
<223> OTHER INFORMATION: Synthetic primer

<400> SEQUENCE: 7
cctcgatgag gctggatatt                                                    20

<210> SEQ ID NO 8
<211> LENGTH: 23
<212> TYPE: DNA
<213> ORGANISM: Artificial Sequence
<220> FEATURE:
<223> OTHER INFORMATION: Synthetic primer

<400> SEQUENCE: 8
gcaccaacca ggaggaaaaa agc                                                23

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
cattcttgcg tccctcaaat                                                    20

<210> SEQ ID NO 10
<211> LENGTH: 23
<212> TYPE: DNA
<213> ORGANISM: Artificial Sequence
<220> FEATURE:
<223> OTHER INFORMATION: Synthetic primer

<400> SEQUENCE: 10
cgacagtctt tctgccatca atg                                                23

<210> SEQ ID NO 11
<211> LENGTH: 19
<212> TYPE: DNA
<213> ORGANISM: Artificial Sequence
<220> FEATURE:
<223> OTHER INFORMATION: Synthetic primer

<400> SEQUENCE: 11
gctgctgttg tcctgtgtt                                                     19

<210> SEQ ID NO 12
<211> LENGTH: 21
<212> TYPE: DNA
<213> ORGANISM: Artificial Sequence
<220> FEATURE:
<223> OTHER INFORMATION: Synthetic primer

<400> SEQUENCE: 12
ccgtcgaagg gggtggcatc c                                                  21

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
tcattcgagc tgaccatcaa                                                    20
```

<210> SEQ ID NO 14
<211> LENGTH: 21
<212> TYPE: DNA
<213> ORGANISM: Artificial Sequence
<220> FEATURE:
<223> OTHER INFORMATION: Synthetic primer

<400> SEQUENCE: 14
ctttatcatt gcacccagca a                                           21

<210> SEQ ID NO 15
<211> LENGTH: 42
<212> TYPE: DNA
<213> ORGANISM: Artificial Sequence
<220> FEATURE:
<223> OTHER INFORMATION: Synthetic primer

<400> SEQUENCE: 15
ggcgcgccta atacgactca ctatagatga tgtgtagggt at                    42

<210> SEQ ID NO 16
<211> LENGTH: 25
<212> TYPE: DNA
<213> ORGANISM: Artificial Sequence
<220> FEATURE:
<223> OTHER INFORMATION: Synthetic primer

<400> SEQUENCE: 16
cgcgggcgcc tgagttcgac aaatt                                       25

<210> SEQ ID NO 17
<211> LENGTH: 22
<212> TYPE: DNA
<213> ORGANISM: Artificial Sequence
<220> FEATURE:
<223> OTHER INFORMATION: Synthetic primer

<400> SEQUENCE: 17
caacgatcct accgccgcac aa                                          22

<210> SEQ ID NO 18
<211> LENGTH: 79
<212> TYPE: DNA
<213> ORGANISM: Artificial Sequence
<220> FEATURE:
<223> OTHER INFORMATION: Synthetic primer

<400> SEQUENCE: 18
ggcgatcggg cgtctaggaa ttctagattt tttttttttt tttttttttt tttttttttt    60
ttttttttaa tttggtcac                                              79

<210> SEQ ID NO 19
<211> LENGTH: 23
<212> TYPE: DNA
<213> ORGANISM: Artificial Sequence
<220> FEATURE:
<223> OTHER INFORMATION: Synthetic primer

<400> SEQUENCE: 19
ggcgatcggg cgtctaggaa ttc                                         23

<210> SEQ ID NO 20
<211> LENGTH: 22
<212> TYPE: DNA
<213> ORGANISM: Artificial Sequence
<220> FEATURE:

<223> OTHER INFORMATION: Synthetic primer

<400> SEQUENCE: 20
caacgatcct accgccgcac aa					22

<210> SEQ ID NO 21
<211> LENGTH: 22
<212> TYPE: DNA
<213> ORGANISM: Artificial Sequence
<220> FEATURE:
<223> OTHER INFORMATION: Synthetic primer

<400> SEQUENCE: 21
ggccccagtg ctgcaatgat ac					22

<210> SEQ ID NO 22
<211> LENGTH: 31
<212> TYPE: DNA
<213> ORGANISM: Artificial Sequence
<220> FEATURE:
<223> OTHER INFORMATION: Synthetic primer

<400> SEQUENCE: 22
agaagaaaaa gaaaagtact gctccaatgg g				31

<210> SEQ ID NO 23
<211> LENGTH: 30
<212> TYPE: DNA
<213> ORGANISM: Artificial Sequence
<220> FEATURE:
<223> OTHER INFORMATION: Synthetic primer

<400> SEQUENCE: 23
ccccattgga gcagtacttt tcttttcctt				30

<210> SEQ ID NO 24
<211> LENGTH: 28
<212> TYPE: DNA
<213> ORGANISM: Artificial Sequence
<220> FEATURE:
<223> OTHER INFORMATION: Synthetic primer

<400> SEQUENCE: 24
gctcagatgg tgagcaaggg cgaggagc					28

<210> SEQ ID NO 25
<211> LENGTH: 31
<212> TYPE: DNA
<213> ORGANISM: Artificial Sequence
<220> FEATURE:
<223> OTHER INFORMATION: Synthetic primer

<400> SEQUENCE: 25
gagtctgaag aggacttgta cagctcgtcc a				31

<210> SEQ ID NO 26
<211> LENGTH: 28
<212> TYPE: DNA
<213> ORGANISM: Artificial Sequence
<220> FEATURE:
<223> OTHER INFORMATION: Synthetic primer

<400> SEQUENCE: 26
tgctgacttt cttgctgatc cacctcct					28

<210> SEQ ID NO 27

```
<211> LENGTH: 26
<212> TYPE: DNA
<213> ORGANISM: Artificial Sequence
<220> FEATURE:
<223> OTHER INFORMATION: Synthetic primer

<400> SEQUENCE: 27
ccttgctcac catctgagca ctcccg                                          26

<210> SEQ ID NO 28
<211> LENGTH: 29
<212> TYPE: DNA
<213> ORGANISM: Artificial Sequence
<220> FEATURE:
<223> OTHER INFORMATION: Synthetic primer

<400> SEQUENCE: 28
gctgtacaag tcctcttcag actccaaga                                       29

<210> SEQ ID NO 29
<211> LENGTH: 22
<212> TYPE: DNA
<213> ORGANISM: Artificial Sequence
<220> FEATURE:
<223> OTHER INFORMATION: Synthetic primer

<400> SEQUENCE: 29
gcggacccag ccaggatcag ac                                              22

<210> SEQ ID NO 30
<211> LENGTH: 100
<212> TYPE: PRT
<213> ORGANISM: Porcine reproductive and respiratory syndrome virus
      (PRRSV)
<220> FEATURE:
<221> NAME/KEY: misc_feature
<223> OTHER INFORMATION: 691 to 790 of ORF1a

<400> SEQUENCE: 30

Gln Glu Ser Gly His Lys Ala Val His Ala Val Pro Leu Ala Glu Gly
1               5                   10                  15

Pro Asn Asn Glu Gln Val Gln Val Val Ala Gly Glu Gln Leu Glu Leu
            20                  25                  30

Gly Gly Cys Gly Leu Ala Ile Gly Ser Ala Gln Ser Ser Ser Asp Ser
        35                  40                  45

Lys Arg Glu Asn Met His Asn Ser Arg Glu Asp Glu Pro Leu Asp Leu
    50                  55                  60

Ser His Pro Ala Pro Ala Ala Thr Thr Thr Leu Val Gly Glu Gln Thr
65                  70                  75                  80

Pro Asp Asn Pro Gly Ser Asp Ala Ser Ala Leu Pro Ile Ala Val Arg
                85                  90                  95

Gly Phe Val Pro
            100

<210> SEQ ID NO 31
<211> LENGTH: 241
<212> TYPE: PRT
<213> ORGANISM: Artificial Sequence
<220> FEATURE:
<223> OTHER INFORMATION: Synthetic GFP insert

<400> SEQUENCE: 31

Met Val Ser Lys Gly Glu Glu Leu Phe Thr Gly Val Val Pro Ile Leu
1               5                   10                  15
```

```
Val Glu Leu Asp Gly Asp Val Asn Gly His Lys Phe Ser Val Ser Gly
         20                  25                  30
Glu Gly Glu Gly Asp Ala Thr Tyr Gly Lys Leu Thr Leu Lys Phe Ile
             35                  40                  45
Cys Thr Thr Gly Lys Leu Pro Val Pro Trp Pro Thr Leu Val Thr Thr
 50                  55                  60
Leu Thr Tyr Gly Val Gln Cys Phe Ser Arg Tyr Pro Asp His Met Lys
 65                  70                  75                  80
Gln His Asp Phe Phe Lys Ser Ala Met Pro Glu Gly Tyr Val Gln Glu
                 85                  90                  95
Arg Thr Ile Phe Phe Lys Asp Asp Gly Asn Tyr Lys Thr Arg Ala Glu
            100                 105                 110
Val Lys Phe Glu Gly Asp Thr Leu Val Asn Arg Ile Glu Leu Lys Gly
        115                 120                 125
Ile Asp Phe Lys Glu Asp Gly Asn Ile Leu Gly His Lys Leu Glu Tyr
130                 135                 140
Asn Tyr Asn Ser His Asn Val Tyr Ile Met Ala Asp Lys Gln Lys Met
145                 150                 155                 160
Glu Asn Gly Ile Lys Val Asn Phe Lys Ile Arg His Asn Ile Glu Asp
                165                 170                 175
Gly Ser Val Gln Leu Ala Asp His Tyr Gln Gln Asn Thr Pro Ile Gly
            180                 185                 190
Asp Gly Pro Val Leu Leu Pro Asp Asn His Tyr Leu Ser Thr Gln Ser
        195                 200                 205
Ala Leu Ser Lys Asp Pro Asn Glu Lys Arg Asp His Met Val Leu Leu
210                 215                 220
Glu Phe Val Thr Ala Ala Gly Ile Thr Leu Gly Met Asp Glu Leu Tyr
225                 230                 235                 240
Lys

<210> SEQ ID NO 32
<211> LENGTH: 25
<212> TYPE: DNA
<213> ORGANISM: Artificial Sequence
<220> FEATURE:
<223> OTHER INFORMATION: Synthetic primer

<400> SEQUENCE: 32
caagtcctct acagggccca tactc                                         25

<210> SEQ ID NO 33
<211> LENGTH: 26
<212> TYPE: DNA
<213> ORGANISM: Artificial Sequence
<220> FEATURE:
<223> OTHER INFORMATION: Synthetic primer

<400> SEQUENCE: 33
ggccctgtag aggacttgta cagctc                                        26

<210> SEQ ID NO 34
<211> LENGTH: 22
<212> TYPE: DNA
<213> ORGANISM: Artificial Sequence
<220> FEATURE:
<223> OTHER INFORMATION: Synthetic primer

<400> SEQUENCE: 34
cttgctgatc cacctcctca gg                                            22
```

```
<210> SEQ ID NO 35
<211> LENGTH: 21
<212> TYPE: DNA
<213> ORGANISM: Artificial Sequence
<220> FEATURE:
<223> OTHER INFORMATION: Synthetic primer

<400> SEQUENCE: 35
ccgtcggagg gggtggcatc c                                         21

<210> SEQ ID NO 36
<211> LENGTH: 21
<212> TYPE: DNA
<213> ORGANISM: Artificial Sequence
<220> FEATURE:
<223> OTHER INFORMATION: Synthetic primer

<400> SEQUENCE: 36
gtctgtgtcc ttggacgagt g                                         21

<210> SEQ ID NO 37
<211> LENGTH: 21
<212> TYPE: DNA
<213> ORGANISM: Artificial Sequence
<220> FEATURE:
<223> OTHER INFORMATION: Synthetic primer

<400> SEQUENCE: 37
ccaagcggcc aaggatagat c                                         21

<210> SEQ ID NO 38
<211> LENGTH: 30
<212> TYPE: DNA
<213> ORGANISM: Artificial Sequence
<220> FEATURE:
<223> OTHER INFORMATION: Synthetic primer

<400> SEQUENCE: 38
cgggatccat ggtgagcaag ggcgaggagc                                30

<210> SEQ ID NO 39
<211> LENGTH: 32
<212> TYPE: DNA
<213> ORGANISM: Artificial Sequence
<220> FEATURE:
<223> OTHER INFORMATION: Synthetic primer

<400> SEQUENCE: 39
cctaagcttc cttgtacagc tcgtccatgc cg                             32

<210> SEQ ID NO 40
<211> LENGTH: 26
<212> TYPE: DNA
<213> ORGANISM: Artificial Sequence
<220> FEATURE:
<223> OTHER INFORMATION: Synthetic primer

<400> SEQUENCE: 40
gcagatcttc agactccaag agagaa                                    26

<210> SEQ ID NO 41
<211> LENGTH: 41
<212> TYPE: DNA
<213> ORGANISM: Artificial Sequence
<220> FEATURE:
<223> OTHER INFORMATION: Synthetic primer
```

```
<400> SEQUENCE: 41
gcagatctgg tggtggtggt tcctcagact ccaagagaga a                    41

<210> SEQ ID NO 42
<211> LENGTH: 36
<212> TYPE: DNA
<213> ORGANISM: Artificial Sequence
<220> FEATURE:
<223> OTHER INFORMATION: Synthetic primer

<400> SEQUENCE: 42
atcccaagct tgcggggatc ccgggacaaa tcctcg                          36

<210> SEQ ID NO 43
<211> LENGTH: 15521
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Chemically synthesized SD01-08 GFP/ES4 marker
      virus

<400> SEQUENCE: 43
atgatgtgta gggtatcccc cctacataca caacactttt tgtgtttgtg tactttggag    60
gcgtgggtac agccccgccc caccccttgg cccctgttct agcccaacag gtatccttct   120
ccctcggggc gagtgcgccg cctgctgctc ccttgcagtg gaaggacct cccgagtatt    180 tccggagagc acctgcttta cgggatctcc acccttaac catgtctggg acgttctccc   240
ggtgcatgtg cacccccggct gcccgggtat tttggaacgc cggccaagtc ttttgcacac   300
ggtgtctcag tgcgcggcct cttctctctc cggaacttca ggacactgac ctcggtgtag   360
ttggattgtt ttacaagcct aaggacaaga ttcactggaa agttcctatc ggcattcctc   420
aggtggagtg tactccatcc gggtgctgct ggctctcagc cgtattccct ttggcgcgca   480
tgacttccgg taatcacaac ttcctccaac gacttgttaa ggttgctgat gttttgtatc   540
gcgatggttg cttggcgcct cgacacctcc gtgaactcca gtttacgag cgcggttgta    600 gctggtaccc aattacgggg cccgtacccg gaatgggttt gtttgcgaac tccatgcacg   660
tgtctgacca gccgttccct ggtgccaccc atgtgttgac taactcgcct ctgcctcagc   720
gggcgtgccg gcagccgttc tgtccatttg aggaagctca ttctgacgtt tacaggtgga   780
agaaatttgt gatttttacg gactcctctc ccaacggtcg atttcgcatg atgtggacgc   840
cggaatccga tgactcagcc gccctggagg tgctgccgcc cgagttagaa cgtcaggtcg   900
agatcctcac tcggagtttt ccgctcatc accctatcaa cctagctgac tgggagctca   960
ctgagtcccc tgagaacggt ttttctttcg gcacgtccca ttcttgcggc cacatcgtcc  1020
agaaccccaa cgtgtttgac ggcaagtgct ggctcacctg ctttttgggc caatcggctg  1080
aagtgtgcta ccacgaggaa catctagcta acgccctcgg ttaccaaacc aagtggggcg  1140
tgcatggtaa gtacctccaa cgcaggcttc aagtccgcgg catgcgtgct gtggtcgatc  1200
ctgacggccc tattcacgtt gaagcgctgt cttgctccca gtcttgggtc aggcacctga  1260
ctctgaataa tgatgtcacc ccaggattcg ttcgcctgac atccatccgc attgtgtcca  1320
acacagaacc caccgctttc ggatctttc ggtttggagc acataagtgg tatggcgctg  1380
ccggcaaacg ggctcgtgcc aaacgtgcca ccaaaagtgg gaaggattcg gccctcgctc  1440
ccaagattgc cccaccggtc cccacctgtg gaatcaccac ctactctcca ccgacagacg  1500
```

| | |
|---|---|
| ggtcttgtgg ttggcacgtt cttgccgcca tagtgaatcg gatgataaac ggtgacttta | 1560 |
| cgtccccccct gcctcagtac aacagaccag aggatgattg ggcttctgat tatgatcttg | 1620 |
| ctcaggcgat tcaatgttta caactgcctg ccaccgtggt tcggaatcgc gcctgtccta | 1680 |
| acgccaagta cctcataaag ctaaacgggg ttcactggga agtagaggtg agatctggaa | 1740 |
| tggctcctcg ttccctttct cgtgaatgtg tagttggcgt ttgctctgaa ggctgtgtcg | 1800 |
| caccgcctta tccagcggac gggcttccta acgtgcact cgaggccttg gcgtctgcct | 1860 |
| acagactacc ctcagattgt gttagctctg gtattgctga ctttcttgct gatccacctc | 1920 |
| ctcaggaatt ctggactctc gacaaaatgt tgacctcccc gtcaccggag cggtccggct | 1980 |
| tctccagctt gtataaatta ctcttagagg ttgttccgca aaaatgtggt gctacggaag | 2040 |
| gggctttcgt ctatgctgtt gagaggatgt taaaggactg tccgagcccc gaacaggcca | 2100 |
| tggcccttct ggcaaaaatt aaagttccat cctcaaaggc cccgtctgtg tccttggacg | 2160 |
| agtgttttcc tgcgggtgtt ccagccgact tcgagccagc atttcaggaa aggcccccaaa | 2220 |
| gtcccggtgc tgctgtcgcc ctgtgttcac cggacgcaaa agggttcgag ggaacagcct | 2280 |
| cggaagaagc tcaagagagt ggccataagg ccgtccacgc tgtacccctt gccgaaggtc | 2340 |
| ccaataatga acaggtacag gtggttgctg gtgagcagct agagctcggc ggttgtggtt | 2400 |
| tggcaatcgg gagtgctcag atggtgagca agggcgagga gctgttcacc ggggtggtgc | 2460 |
| ccatcctggt cgagctggac ggcgacgtaa acggccacaa gttcagcgtg tccggcgagg | 2520 |
| gcgagggcga tgccacctac ggcaagctga ccctgaagtt catctgcacc accggcaagc | 2580 |
| tgcccgtgcc ctggcccacc ctcgtgacca ccctgaccta cggcgtgcag tgcttcagcc | 2640 |
| gctaccccga ccacatgaag cagcacgact tcttcaagtc cgccatgccc gaaggctacg | 2700 |
| tccaggagcg caccatcttc ttcaaggacg acggcaacta caagacccgc gccgaggtga | 2760 |
| agttcgaggg cgacaccctg gtgaaccgca tcgagctgaa gggcatcgac ttcaaggagg | 2820 |
| acggcaacat cctggggcac aagctggagt acaactacaa cagccacaac gtctatatca | 2880 |
| tggccgacaa gcagaagaac ggcatcaagg tgaacttcaa gatccgccac aacatcgagg | 2940 |
| acggcagcgt gcagctcgcc gaccactacc agcagaacac ccccatcggc gacggccccg | 3000 |
| tgctgctgcc cgacaaccac tacctgagca cccagtccgc cctgagcaaa gaccccaacg | 3060 |
| agaagcgcga tcacatggtc ctgctggagt tcgtgaccgc cgccgggatc actctcggca | 3120 |
| tggacgagct gtacaagtcc tctacagggc ccatactccg tcatgttgag cactgcggca | 3180 |
| cagagtcagg cgacagcagt tcgcctttgg atctgtcttt tgcgcaaacg ttggaccagc | 3240 |
| ctttagatct atccttggcc gcttggccgg tgaaggccac cgcgtctgat cctggctggg | 3300 |
| tccgcggtag gtgcgagcct gtcttttaa agcctcggaa agctttctct gatgcgatt | 3360 |
| cggcccttca gttcggggag ctttctgagt ccagctctgt catcgagttt gaccagacaa | 3420 |
| aagatactct ggtggctgac gcccctgttg acttgacgac ttcgaacgag gccctctctg | 3480 |
| cagtcgaccc ttccgaattt gtcgaactca ggcgcccgcg tcattccgca aagccttaa | 3540 |
| ttgaccgagg cggtccactt gctgatgtcc atgcgaaaat aaagaaccgg tgtatgaac | 3600 |
| agtgcctcca agcttgtgag cctggtagtc gtgcaacccc agccaccagg gagtggctcg | 3660 |
| acaaaatgtg ggataggtg gacatgaaaa cttggcgctg cacttcacag ttccaggccg | 3720 |
| gtcgcattct tgcgtccctc aaatttcttc ctgacatgat tcaagacacg ccgcctcctg | 3780 |
| tccccaagaa gaaccgagct agtgacagtg ccggtcagac cgtccctccg cctacggata | 3840 |
| tccagcaaga ggatgccacc ccctccgacg ggttatccca tgcatcggat ttttctagtc | 3900 |

```
gagtgagcac gagctggagt tggaaaggcc ttatgctttc cggcacccgt ctcgcggggt    3960
ctgctggtca gcgcctcatg acatgggttt ttgaagtttta ctccatctc ccagctttta    4020 tactcacact tttctcgccg cggggctcta tggctccagg cgattggttg tttgcaggtg    4080
ttgttttact tgctctcttg ctctgtcgtt cttacccaat actcggatgc cttcccttac    4140
tgggtgtctt ctctggttct ttgcggcgtg ttcgtctggg tgttttttggt tcttggatgg    4200 cttttgctgt atttttattc tcgactccat ccaacccagt cggttcttct tgtgaccacg    4260
attcgccgga atgtcatgct gagcttttgg ctcttgagca gcgccaactt tgggaacctg    4320
tgcgcggcct tgtggttggc ccctcaggtc tcttatgtgt catccttggc aagttactcg    4380
gtgggtcacg tcatctctgg catgttatcc tacgtttatg catgcttaca gatttggccc    4440
tttctcttgt ttatgtggtg tcccaagggc gttgtcacaa gtgttgggga aagtgtataa    4500
ggacagctcc tgctgaggtg gctctcaatg tatttccttt ctcgcgcgcc actcgcaact    4560
ctctcacatc cttgtgtgat cggttccaaa ctcctaaagg agttgatccc gtgcacttgg    4620 caacggggttg gcgcgggtgt tggcgtggtg agagtcccat ccatcaacca caccaaaagc    4680
ccatagctta tgccaatttg gatgaaaaga aaatatctgc tcaaacggtg gttgctgtcc    4740
catacgaccc cagtcaggct atcaaatgtc tgaaggttct gcaggcggga ggggctatcg    4800
tggaccagcc tacgcctgaa gttgttcgtg tgtctgaaat ccccttttca gccccatttt    4860
tcccaaaagt tccagtcaac ccagattgca ggattgtggt ggattcagat acttttgtgg    4920
ctgcagtccg ctgcggttac tcgacagcac aactggtcct aggccggggc aactttgcca    4980
agttgaatca gaccccccctt agggactctg cctccaccaa aacgactggt ggggcctctt    5040
atactcttgc tgtggctcaa gtgtctgtgt ggactcttgt tcatttcatc ctcggtcttt    5100
ggttcacatc acctcaagtg tgtggccgag gaaccgctga cccatggtgt tcaaatccct    5160
tttcgtatcc tgcctacggc cctggagttg tgtgctcctc tcgactttgt gtgtctgccg    5220
atggggtcac cctgccattg ttctcagctg tggcacaact ctccggtaga gaggtaggga    5280 ttttttatttt agtgcttgtt tccttgactg ccttggccca tcgcctggct cttaaggcag    5340
acatgttagt ggtcttttca gcttttttgtg cttacgcctg gcccatgagc tcctggttaa    5400
tctgcttctt tcctatactc ttaaagtggg ttacccttca cccctcact atgctttggg    5460 tgcactcatt cttggtgttt tgtatgccag cagccggcat cctctcacta gggataactg    5520
gccttctctg ggcagttggc cgcttttaccc aggttgccgg aattattaca ccttatgaca    5580
tccaccagta tacctctggg ccacgcggtg cagccgctgt agccacagcc ccagaaggca    5640
cttatatggc cgccgtccgg agagctgctt taactggacg aactttgatc ttcaccccgt    5700
ctgcggtcgg atcccttctt gaaggtgctt tcaggactca taaaccctgc cttaacaccg    5760
tgaatgttgt gggttcttcc cttggttctg gaggggtttt taccattgat ggcagaaaga    5820
ccgtcgtcac tgctgctcat gtgttgaacg gcgacacagc tagagttacc ggcgactctt    5880
acaaccgcat gcacactttt aagaccagtg gcgattatgc ctggtcccat gctgatgact    5940
ggcagggcgt tgcccctgtg gtcaaggttg cgaaggggta tcgcggtcgt gcctactggc    6000
aaacatcaac cggtgtcgaa cccggcgtca ttggggaagg gttcgccttc tgtttcacca    6060
actgtggcga ttcggggtca cccgtcatct cagaatctgg tgatctcatc ggaatccata    6120
ccggttcaaa caaactcggt tctggtcttg tgacgacccc tgaagggaa acctgcgcca    6180 tcaaagaaac caagctctct gacctttcca gacatttttgc gggcccgagc gtccctcttg    6240
gggacattaa attgagtccg gccatcgtcc ctgatgtaac atctattccg agtgacttgg    6300
```

```
catcgctcct agcttccgtc cctgtaatgg aaggcggcct ctcgaccgtt caacttctgt    6360
gtgtcttttt ccttctctgg cgcatgatgg gccatgcctg acacccatt gttgccgtgg     6420 gcttcttttt gctgaatgaa attcttccag cagttttggt ccgagccgtg ttttcctttg    6480
cactctttat tcttgcatgg gccaccccct ggtccgcaca ggtgttaatg attagactcc    6540
tcacggcatc cctcaaccgc aacaagttgt ctctggcgtt ctacgcactt ggggtgtcg    6600 tcggtttggc cgctgaaatc ggggcttttg ccggcaggct gcctgaattg tctcaagctc    6660
tttcgacata ctgtttctta cctagggtcc ttgccatggc cagttatgtt cccatcatca    6720
tcattggtgg actccatgcc ctcggtgtga ttctgtggtt gttcaaatac cggtgcctcc    6780
acaacatgct ggttggtgat gggagtttct caagcgcttt cttcctacgg tattttgcag    6840
agggtaatct tagaaaaggt gtttcacagt cttgtggcat gagtaacgag tccctgacgg    6900
ctgctctagc ttgcaagttg tcgcaggctg accttgactt tttgtccagc ttaacgaact    6960
tcaagtgctt tgtatctgct tcaaacatga aaaatgctgc cggccagtat attgaagcag    7020
cgtatgccaa ggccctgcgc caagagttgg cctccctagt tcaggttgac aaaatgaaag    7080
gaattttgtc taagcttgag gcctttgctg aaacagccac tccgtcsctt gacgcaggtg    7140
acgtggttgt tctgcttggg caacatcctc acggatccat cctcgatatt aatgtgggga    7200
ctgaaaggaa aactgtgtcc gtgcaagaga cccggagctt aggtggttcc aaattcagtg    7260
tttgcactgt cgtgtccaac acaccegtgg acgccttaac tggcatccca ctccagacac    7320 caaccectct ttttgagaat ggtccgcgtc accgtggtga ggaagacgat cttagagtcg    7380
agaggatgaa gaaacactgt gtgtccctcg gcttccacaa cattaatggc aaagtttact    7440
gcaaaatttg ggacaagtcc accggtgata cctttttatac cgatgattcc cggtacaccc    7500
aagaccttgc attccaggac aggtcagccg actacagaga cagggattat gagggtgtgc    7560
aaaccgcccc ccaacagggc tttgatccaa agtctgaaac ccctattggc actgtggtga    7620
tcggcggtat cacgtataac aggtacctga tcaaaggtaa ggaggtcttg gttcccaagc    7680
ctgacaactg ccttgaagct gccaagctgt cccttgagca agctctcgct gggatgggcc    7740
aaacttgcga ccttacagct gccgaggtgg aaaagttgag gcgcatcatt agccagctcc    7800
aaggtttgac cactgaacag gctttaaact gttagccgcc agcggcttga cccgctgtgg    7860
ccgcggcggc ttagttgtaa ctgaaacagc ggtaaaaatc gtaaagtacc acagcagaac    7920
tttcacccta ggccctctgg acctgaaagt cacctccgag gctgaggtaa agaaatcaac    7980
tgagcagggc cacgctgttg tggcaaactt atgttctggt gtcatcttga tgagacctca    8040
cccaccgtcc cttgttgatg ttcttctgaa acccggactt gacacaaaac ccggcattca    8100
accagggcat ggggccggga atatgggcgt agacggctct acttgggatt ttgaaaccgc    8160
acccacaaag gcagaacttg agttgtccaa acaaataatt caagcatgtg aagttaggcg    8220
cggggacgcc ccgaacctcc aactcccctta caagctctat cctgttagag gggatcctga    8280
gcggcatggg ggccgcctta tcaataccag gtttggagat ctatcttaca aaacccctca    8340
agacaccaag tccgcaatcc atgcggcttg ttgcctgcac cccaacgggg cccctgtgtc    8400
tgatggtaag tcaacactag gtaccaccct tcaacatggt ttcgaacttt atgtccccac    8460
tgtgccctat agtgtcatgg agtacctcga ttcacgccct gacacccctt tcatgtgcac    8520
taaacatggt acttccaagg ctgctgcaga agacctccaa aaatacgacc tatctactca    8580
aggatttgtc ctgccggggg tcttacgcct tgtacgcaga ttcatctttg gccatattgg    8640
taaggcaccg ccattgttcc tcccgtcaac ctatcccgct aaaaattcta tggcagggat    8700
```

```
caatggccag aggttcccaa caaaggacgt ccagagcata cctgaaattg acgaaatgtg   8760
tgcccgcgcc gtcaaggaga attggcaaac tgtgacacct tgtaccctca agaaacagta   8820
ctgttccaag cccaaaacca ggaccatcct gggcaccaac aactttattg ccctggctca   8880
ccgatcggcg ctcagtggtg tcacccaggc attcatgaag aaggcttgga agtcccgat    8940
tgccttggga aaaaacaaat tcaaggagct gcattgcact gtcgccggca ggtgtcttga   9000
agccgacttg gcctcctgtg accgcagcac ccccgccatt gtgaggtggt tcgtcgccaa   9060
cctcctgtat gaacttgcag gatgtgaaga gtacttgcct agctatgtgc ttaactgctg   9120
ccatgacctt gtggcaacac aggatggtgc cttcacaaaa cgcggtggcc tgtcgtccgg   9180
ggaccccgtc accagtgtgt ctaacaccgt atattcactg ataatctatg cccagcacat   9240
ggtgttgtcg gccttaaaaa tgggtcatga aatcggtctc aagttcctcg aggaacagct   9300
caaattcgag gacctcctcg aaatccagcc tatgttggtc tattctgatg accttgtctt   9360
gtacgctgaa aggcccactt ttcctaatta tcactggtgg tcgagcacc ttgacctaat    9420
gctgggtttc agaacggacc caaagaagac agtcataact gataaaccca gcttcctcgg   9480
ctgcagaatt gaggcgggc acagctggt ccctaatcgc gaccgcatcc tggctgctct     9540
cgcatatcac atgaaggcgc agaacgcctc agagtattat gcgtctgctg ccgcaatcct   9600
gatggattca tgtgcttgca ttgatcatga ccctgagtgg tatgaggacc tcatctgcgg   9660
tatcgcccga tgcgcccgcc aggatggtta tagtttccca ggcccggcat ttttcatgtc   9720
catgtgggaa aagctgagaa gtcacaatga agggaagaaa tttcgacact gcggcatctg   9780
cgacgccaaa gccgaccatg catccgcctg tgggcttgat ttgtgtttgt tccactcaca   9840
ctttcatcaa cactgccccg tcactctgag ctgtggtcat catgccggtt caagggaatg   9900
ttcgcagtgt cagtcacctg ttggggctgg cagatctcct cttgatgccg tgctaaaaca   9960
aatcctgtac aaacctcctc gtacagtcat catgaaggtg ggtaacaaaa caacggccct  10020
cgatccgggg aggtaccagt cccgtcgagg tcttgttgca gtcaagaggg gtattgcagg  10080
caatgaagtt gatcttcctg atggggacta ccaagtagtg cctcttttac caacttgtaa  10140
agacataaac atggtaaagg tggcttgcaa tgtactactc agtaagttca tagtggggcc  10200
accaggttcc ggaaagacca cctggttact gagtcaagtc caggacgatg atgtcattta  10260
cacacccacc catcagacca tgtttgatat agtcagtgct ctcaaagttt gcaggtattc  10320
tattccagga gcctcaggac ttcctttccc accacctgcc aggtccgggc cgtgggttag  10380
gctcgtggcc agcgggcacg tccccggccg aacatcatac ctcgatgagg ctggatattg  10440
taatcatctg gacattctca gactgctttc caaaacaccc ctcgtgtgtt gggtgacct   10500
tcaacaactt caccctgtcg gctttgactc ctactgttat gtgtttgatc agatgcctca  10560
aaagcaactg accactattt atagatttgg ccctaacatc tgcgcagcca tccagccttg  10620
ttacaggag aagcttgaat ctaaggctag gaacaccagg gtggtcttta ccacctggcc   10680
tgtggccttt ggtcaggtgc tgacaccata ccataaagat cgcatcggct ctgcgataac  10740
catagactca tcccagggg ccactttcga cattgtgaca ttgcatctac catcaccaaa   10800
gtccctaaat aaatcccgag cacttgtagc catcactcgg gcaagacacg ggttgttcat  10860
ttatgacccc cacaaccagc tccaggagtt tttcaacctg atccctgagc gcactgattg  10920
caaccttgtg ttcagccgtg gggatgatct ggtagttctt agtgcggaca atgcagtcac  10980
aactgtagcg aaggccctag ggacaggtcc atctcgattt cgagtatcag acccgaggtg  11040
caagtctctc ttagctgctt gttcggccag tctggagggg agctgtatgc cactaccaca  11100
```

```
agtggcacat aacctggggt tttacttctc cccagacagt ccagcatttg cacctctgcc    11160
aaaggagtta gcgccacatt ggccagtggt tactcaccag aacaatcggg cgtggcccga    11220
tcgacttgtc gctagtatgc gcccaattga tgcccgctac agcaagccaa tggtcggtgc    11280
agggtatgtg gtcgggccgt ccaccttcct tggtactcct ggtgtagtgt catactacct    11340
cacgctatac atcaggggtg agccccaggc cttgccagag acactcgttt caacaggacg    11400
catagccact gactgccggg agtatctcga cgcggctgag gaagaggcag caaagaact    11460 cccccacgca ttcattggcg atgtcaaagg taccacggtc gggggtgtc accacatcac     11520 atcaaaatac ctacccagga ccctgcctaa ggactctgtt gctgtagttg gagtaagctc    11580
gcccggcagg gctgctaaag ccatgtgcac tctcactgat gtgtatctcc ccgaactccg    11640
gccatacctg caacctgaga cggcgtcgaa atgctggaaa ctcaaattag acttcaggga    11700
cgtccgacta atggtctgga aaggagccac cgcctatttc cagttggaag gacttacatg    11760
gtcagcgctg cctgactatg ccaggtttat tcagcttccc aaggacgccg ttgtgtacat    11820
tgatccgtgt ataggaccgg caacagccaa ccgcaaggtc gtgcgaacca cagactggcg    11880
ggccgacctg gcagtgacac cgtatgatta cggtgcccag aacattttga caacagcctg    11940
gttcgaggac ctcgggccgc agtggaagat tttggggttg cagcccttca ggcgggcatt    12000 tggcttttgaa aatactgagg attgggcaat ccttgcacgc cgtatgagtg acggcaaaga    12060
ctacactgac tacaactggg attgtgttcg agaacgccca cacgccatct acgggcgtgc    12120
tcgtgaccat acatatcatt ttgccccgg cacggaattg caggtagagc tgggtaaacc    12180
ccggctgccg cctggacgag agccgtaaac ttggagtgat gcaatggggt cactgtggag    12240
taaaatcagc cagctgttcg tggatgcctt cactgagttt cttgtcagtg tggttgatat    12300
tgtcattttc cttgccatac tgtttgggtt caccgtcgca ggatggttat tggtctttct    12360
tctcagagtg gtttgctccg cgcttctccg ttcgcgctct gccattcact ctcccgaact    12420
atcgaaggtc ctatgaaagc ttgttgccca actgcaggcc ggatgtccca caatttgcat    12480
ttaagcaccc attgggtata cttttggcaca tgcgagtttc ccacctgatt gatgagatgg    12540
tctctcgccg catttaccag accatggaac attcaggtca agcggcctgg aaatatgtgg    12600
tcggtgaggc cactctcacg aagctatcaa agcttgatat agttactcat ttccaacatc    12660
tggccgcagt agaggcggat tcttgccgct ttctcagctc acgactcgtg atgctaaaaa    12720
atcttgccgt tggcaatgtg agcctacagt acaacaccac gttggatcgc gttgaactca    12780 tttttccccac gccaggtacg aggcccaagt tgaccgactt cagacaatgg ctcatcagtg    12840
tgcatgcttc cattttttcc tctgtggctt catctgttac cttgttcata gtgctttggc    12900
tgcgaattcc agctctacgc tatgttttg gtttccattg gcccacggca acacatcatt    12960
cgagctgacc atcaattata ccatatgcat gccctgtctt accagtcaag cagctcgcca    13020
aaggctcgag cccggtcgta acatgtggtg cagaatagg catgatagg tgtgaggagcg    13080 tgaccatgat gagttgttaa tgtccatccc gtccgggtac gacaacctca acttgagggg    13140
atattatgct tggctggctt ttttgtcctt ttcctacgcg gcccaattcc atccggagct    13200
gttcgggata gggaatgtgt cgcgcgtctt cgtggacaag cgacaccagt ttatttgtgc    13260
cgagcatggg ggactcaatt caaccttatc taccgagcac aatatctccg cattatatgc    13320
ggtatattat caccaccaaa tagacggggg taattggttc catttggaat ggctgcggcc    13380
gcttttttcc tcctggttgg tgctcaacat atcatggttt ctgaggcgtt cgcctgtaag    13440 ccctgttct cgacgcatct atcagatatt aagaccaaca cgaccgcggc tgccggtttc    13500
```

```
atggtccttc agaacatcaa ttgttcccgg cctcacgagg cctcagcaac gcaaggtcaa    13560
gttccctcca gaaagtcgtc ccaatgccgt gaagccgtcg tgttccccca atacatcacg    13620
ataacggcca acgtgaccga cgaatcatat ttgtacaacg cggacttgct gatgcttttct   13680
gcgtgccttt tctacgcctc ggaaatgagc gagaaaggct ttaaagttat ctttgggaat    13740
gtctctggcg ttgtttctgc ttgtgtcaat ttcacagatt atgtggccca tgtgacccaa    13800
catacccagc agcatcatct ggtgattaat cacatccggt tactgcactt cctgacacca    13860
tctgcaatga ggtgggctac aaccattgct tgtctgttcg ccattctctt ggcgatatga    13920
aatgttctca caaattgggg cattccttga ctccgcactc ttgcttctgg tggctttttt    13980
tgctgtgtac cggcttgtcc tggtcctttg ccgatggcaa cggcaacaac tcgacatacc    14040
aatacatata taatttgacg atatgcgagt tgaatgggac caattggctg tccggccatt    14100
ttgaatgggc agttgagacc tttgtgcttt acccggttgt cactcatatc ctctcactgg    14160
gttttctcac gacaagtcat tttttttgacg cgctcggtct cggcgctgta tccactgcag    14220
gatttgtcgg agggcggtat gtacttagca gcgtctacgg cgcttgtgct ttcgcagcgt    14280
tcgtatgctt cgtcatccgt gctgctaaaa attgcatggc ctgccgctat gcccgtaccc    14340
ggttcaccaa cttcattgtg gacgaccggg ggggagttca tagatggaag tctccaatag    14400
tggtagaaaa actgggcaaa gccgaaattg gcggcaacct tgtcaccatc aaacatgtcg    14460
tcctcgaagg ggttaaagct caaccttga cgagaacttc ggccgagcaa tgggaggcct    14520
agataatttt tgcaacgatc ctaccgccgc acaaagatc gtgctagcct tcagcatcac    14580
atacacacct ataatgatat acgcccttaa ggtgtcacgc ggccgactcc tggggctgtt    14640
gcacatccta atatttctga actgttcctt tacattcgga tacatgacat atgtgcattt    14700
tcattctacc caccgtgtcg cacttaccct gggggctgtt gtcgcccttt tgtggggtgt    14760
ctacagcctc acagagtcat ggaagtttat cacttccaga tgcagattgt gttgcctcgg    14820
ccggcgatac attctggccc ctgcccatca cgtagaaagt gctgcaggtc tccattcaat    14880
ctcagcgtct ggtaaccgag catacgctgt gagaaagccc ggactaacat cagtgaacgg    14940
cactctagta ccaggacttc ggagcctcgt gctgggcggc aaacgagctg ttaaacgagg    15000
agtggttaac ctcgtcaagt atggccggta aaatcagag ccagaagaaa aagaaaagta    15060
cggctccaat ggggaatggc cagccagtca atcaactgtg ccagttgctg ggtgcaatga    15120
taaagtccca gcgccagcaa cctaggggag gacaggctaa aaagaaaaag cctgagaagc    15180
cacatttttcc cctggctgca gaagatgaca tccggcacca cctcacccaa actgaacgct    15240
ccctctgctt gcaatcgatc cagacggctt tcaatcaagg cgcaggaact gcgtcgcttt    15300
catccagcgg gaaggtcagt ttccaggttg agtttatgct gccggttgct catacagtgc    15360
gcctgattcg cgtgacttct acatccgcca gtcagggtgc aaattaattt gacagtcagg    15420
tgaatgccccg cgattggcgt gtggcctctg agtcacctat tcaattaggg cgatcacatg    15480
ggggtcatac ttaatcaggc aggaaccatg tgaccgaaat t                        15521
```

<210> SEQ ID NO 44
<211> LENGTH: 15
<212> TYPE: DNA
<213> ORGANISM: Artificial Sequence
<220> FEATURE:
<223> OTHER INFORMATION: Synthetic fragment of GFP gene
<220> FEATURE:
<221> NAME/KEY: CDS
<222> LOCATION: (1)..(15)

<400> SEQUENCE: 44

```
cag gag cgc acc atc                                              15
Gln Glu Arg Thr Ile
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic Construct

<400> SEQUENCE: 45

Gln Glu Arg Thr Ile
1               5

<210> SEQ ID NO 46
<211> LENGTH: 15
<212> TYPE: DNA
<213> ORGANISM: Artificial Sequence
<220> FEATURE:
<223> OTHER INFORMATION: Synthetic mutated GFP gene fragment
<220> FEATURE:
<221> NAME/KEY: CDS
<222> LOCATION: (1)..(15)

<400> SEQUENCE: 46 cag gag tgc acc atc                                              15
Gln Glu Cys Thr Ile
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic Construct

<400> SEQUENCE: 47

Gln Glu Cys Thr Ile
1               5

<210> SEQ ID NO 48
<211> LENGTH: 15
<212> TYPE: DNA
<213> ORGANISM: Artificial Sequence
<220> FEATURE:
<223> OTHER INFORMATION: Synthetic linker sequence

<400> SEQUENCE: 48
ggtggtggtg gttcc                                                 15
```